United States Patent [19]

Brooks et al.

[11] Patent Number: 5,476,873
[45] Date of Patent: Dec. 19, 1995

[54] ACETYLENE DERIVATIVES HAVING LIPOXYGENASE INHIBITORY ACTIVITY

[75] Inventors: Dee W. Brooks, Libertyville; Andrew O. Stewart, Wildwood; Daniel J. Kerkman, Lake Villa; Pramila A. Bhatia, Mundelein; Anwer Basha, Lake Forest, all of Ill.; Jonathan G. Martin, Knoxville, Tenn.

[73] Assignee: Abbott Laboratories, Abbott Park, Ill.

[21] Appl. No.: 229,860

[22] Filed: Apr. 19, 1994

Related U.S. Application Data

[63] Continuation of Ser. No. 971,841, Jan. 22, 1993, abandoned, which is a continuation-in-part of Ser. No. 684,614, Apr. 12, 1991, abandoned, which is a continuation-in-part of Ser. No. 558,050, Jul. 25, 1990, abandoned.

[51] Int. Cl.⁶ .............. C07C 259/06; C07C 273/18; C07C 275/64; A61K 31/17
[52] U.S. Cl. .................................. 514/595; 564/52
[58] Field of Search ............................. 564/52; 514/595

[56] References Cited

U.S. PATENT DOCUMENTS

| | | | |
|---|---|---|---|
| 4,604,407 | 8/1986 | Haslanger et al. | 514/575 |
| 4,608,390 | 8/1986 | Summers, Jr. | 514/575 |
| 4,822,809 | 4/1989 | Summers et al. | 514/367 |
| 4,980,362 | 12/1990 | Carceller et al. | 514/336 |
| 5,037,853 | 8/1991 | Brooks et al. | 514/595 |

FOREIGN PATENT DOCUMENTS

| | | | |
|---|---|---|---|
| 0273451 | 7/1988 | European Pat. Off. | 514/575 |
| 0279263 | 8/1988 | European Pat. Off. | 549/32 |
| 0292699 | 11/1988 | European Pat. Off. | 549/29 |
| 0299761 | 1/1989 | European Pat. Off. | 560/312 |
| 0320628 | 6/1989 | European Pat. Off. | 546/332 |
| WO90/12008 | 10/1990 | WIPO | 546/284 |
| WO92/10469 | 6/1992 | WIPO | 564/52 |

*Primary Examiner*—Alan L. Rotman
*Attorney, Agent, or Firm*—Jerry F. Janssen

[57] ABSTRACT

Compounds of the structure

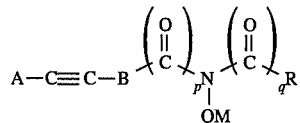

where p and q are zero or one, but cannot both be the same, M is a pharmaceutically acceptable cation or a metabolically cleavable group, B is a valence bond or a straight or branched alkylene group, R is alkyl, cycloalkyl or —NR¹R², where R¹ and R² are hydrogen, alkyl, cycloalkyl or alkanoyl, and A is optionally substituted carbocyclic aryl, furyl, benzo[b]furyl, thienyl, or benzo[b]thienyl are potent inhibitors of lipoxygenase enzymes and thus inhibit the biosynthesis of leukotrienes. These compounds are useful in the treatment or amelioration of allergic and inflammatory disease states.

7 Claims, No Drawings

ACETYLENE DERIVATIVES HAVING LIPOXYGENASE INHIBITORY ACTIVITY

CROSS-REFERENCE TO RELATED APPLICATIONS

This application is a continuation of U.S. patent application Ser. No. 07/971,841 filed Jan. 22, 1993, now abandoned, which is a continuation-in-part of application U.S. Ser. No. 684,614 filed Apr. 12, 1991 abandoned which is a continuation-in-part of U.S. Ser. No. 558,050 filed Jul. 25, 1990, abandoned.

TECHNICAL FIELD

This invention relates to compounds having activity to inhibit lipoxygenase enzymes, to a novel method of preparing such compounds, to pharmaceutical compositions comprising these compounds, and to a medical method of treatment. More particularly, this invention concerns certain substituted alkynyl ureas and hydroxamic acids which inhibit leukotriene biosynthesis, to a novel method of chemical synthesis of the compounds, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most meals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis, cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 4,738,986 to Kneen, et al. discloses and claims N-(3-phenoxycinnamyl)acetohydroxamic acid, its salts and related compounds having utility for inhibiting lipoxygenase and cyclooxygenase enzymes.

European Patent Application 0 299 761 to Salmon, et at. discloses and claims certain (substituted phenoxy)phenylalkenyl hydroxamic acids and their salts which are useful as agents for inhibitng lipoxygenase and cyclooxygenase activity.

SUMMARY OF THE INVENTION

In its principal embodiment, the present invention provides certain substituted alkynylene compounds which inhibit lipoxygenase enzyme activity and are useful in the treatment of allergic and inflammatory disease states in which leukotrienes play a role including including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The compounds of this invention have the structure

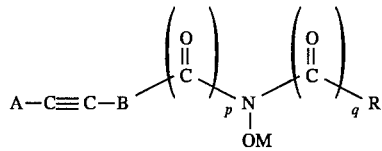

where B is a valence bond or is a straight or branched divalent alkylene group of from one to twelve carbon atoms. The group M represents hydrogen, a pharmaceutically acceptable cation, or a pharmaceutically acceptable metabolically cleavable group. The subscripts p and q are independently zero or one, with the proviso that p and q may not both be the same.

When p is one and q is zero, the compounds of the present invention comprise a class of hydroxamic acids where R is selected from the group consisting of hydrogen, straight or branched alkyl of from one to twelve carbon atoms, and cycloalkyl of from three to eight carbon atoms.

When p is zero and q is one, the compounds of the present invention comprise a class of N-hydroxy amide and urea compounds where R is selected from the group consisting of hydrogen, alkyl of from one to twelve carbon atoms, cycloalkyl of from three to eight carbon atoms, and —$NR^1R^2$ where $R^1$ is selected from the group consisting of hydrogen, alkyl of from one to six carbon atoms, hydroxyalkyl of from one to six carbon atoms, and alkoxyalkyl in which the alkoxy portion and the alkyl portion each contain, independently, from one to six carbon atoms. $R^2$ is selected from the group consisting of hydrogen, hydroxy, alkyl of from one to six carbon atoms, hydroxyalkyl of from one to six carbon atoms, alkoxyalkyl in which the alkoxy portion and the alkyl portion each contain, independently, from one to six carbon atoms, alkanoyl of from two to eight carbon atoms, alkyl(carbocyclic aryl) in which the alkyl portion contains from one to six carbon atoms, and optionally substituted (carbocyclic aryl).

The group A is selected from the group consisting of substituents (a) through (q) listed below: (a) alkyl of from five to twenty carbon atoms; (b) cycloalkyl of from three to eight carbon atoms; (c) optionally substituted carbocyclic aryl; (d) optionally substituted carbocyclic aryloxy; (e) optionally substituted (carbocyclic aryl)cycloalkyl in which the cycloalkyl portion may contain from three to eight carbon atoms; (f) optionally substituted (carbocyclic aryl)alkyl in which the alkyl portion may contain from one to six carbon atoms; (g) optionally substituted carbocyclic aryloxyalkyl in which the alkyl portion contains from one to six carbon atoms; (h) optionally substituted (carbocyclic aryl)alkoxyalkyl in which the alkoxyl and alkyl portions may independently contain from one to six carbon atoms; (i) optionally substituted carbocyclic arylthioalkyl in which the alkyl portion may contain from one to six carbon atoms; (j) optionally substituted carbocyclic arylaminoalkyl in which the alkyl portion may contain from one to six carbon atoms; (k) optionally substituted [N-(carbocyclic aryl)-N-alkylamino]alkyl in which the two alkyl portions may independently contain from one to six carbon atoms; (l) optionally substituted [N-(carbocyclic arylalkyl)amino]alkyl in which the two alkyl portions may independently contain from one to six carbon atoms; (m) optionally substituted [N-(carbocyclic arylalkyl)-N-alkylamino]alkyl in which the three alkyl portions may independently contain from one to six carbon atoms.

In all of the above-recited choices for A, the term "carbocyclic aryl" denotes phenyl or 1- or 2-naphthyl, and the optional substituents are selected from the group consisting of: (1) alkyl of from one to six carbon atoms, (2) haloalkyl of from one to six carbon atoms, (3) hydroxyalkyl of from one to six carbon atoms, (4) alkoxy of from one to twelve carbon atoms, (5) alkoxyalkoxyl in which the two alkoxy portions may each independently contain from one to six carbon atoms, (6) alkylthio of from one to six carbon atoms, (7) hydroxy, (8) halogen, (9) cyano, (10) amino, (11) alkylamino of from one to six carbon atoms, (12) dialkylamino in which the two alkyl groups may independently contain from one to six carbon atoms, (13) alkanoylamino of from two to eight carbon atoms, (14) N-alkanoyl-N-alkylamino in which the alkanoyl may contain from two to eight carbon atoms and the alkyl groups may contain from one to six carbon atoms, (15) alkylaminocarbonyl of from two to eight carbon atoms, (16) diallcylaminocarbonyl in which the two alkyl groups may independently contain from one to six carbon atoms, (17) carboxyl, (18) alkoxycarbonyl of from two to eight carbon atoms, (19) phenyl, optionally substituted with (19a) alkyl of from one to six carbon atoms, (19b) haloalkyl of from one to six carbon atoms, (19c) alkoxy of from one to six carbon atoms, (19d) hydroxy, or (19e) halogen; (20) phenoxy, optionally substituted with (20a) alkyl of from one to six carbon atoms, (20b) haloalkyl of from one to six carbon atoms, (20c) alkoxy of from one to six carbon atoms, (20d) hydroxy or (20e) halogen, (21) phenylthio, optionally substituted with (21a) alkyl of from one to six carbon atoms, (21b) haloalkyl of from one to six carbon atoms, (21c) alkoxy of from one to six carbon atoms, (21d) hydroxy or (21e) halogen; (22) 2- 3-, or 4-pyridyl, optionally substituted with (22a) alkyl of from one to six carbon atoms, (22b) haloalkyl of from one to six carbon atoms, (22c) alkoxy of from one to six carbon atoms, (22d) hydroxy or (22e) halogen; (23) 2-, 3-, or 4-pyrictinyloxy, optionally substituted with (23a) alkyl of from one to six carbon atoms, (23b) haloalkyl of from one to six carbon atoms, (23c) alkoxy of from one to six carbon atoms, (23d) hydroxy or (23e) halogen; (24) 2- or 3-furyl, optionally substituted with (24a) alkyl of from one to six carbon atoms, (24b) haloalkyl of from one to six carbon atoms, (24c) alkoxy of from one to six carbon atoms, (24d) hydroxy or (24e) halogen; (25) thienyloxy, optionally substituted with (25a) alkyl of from one to six carbon atoms, (25b) haloalkyl of from one to six carbon atoms, (25c) alkoxy of from one to six carbon atoms, (25d) hydroxy or (25e) halogen; (26) thiazolyloxy, optionally substituted with (26a) alkyl of from one to six carbon atoms, (26b) haloalkyl of from one to six carbon atoms, (26c) alkoxy of from one to six carbon atoms, (26d) hydroxy or (26e) halogen; (27) benzoxazolyloxy, optionally substituted with (27a) alkyl of from one to six carbon atoms, (27b) haloalkyl of from one to six carbon atoms, (27c) alkoxy of from one to six carbon atoms, (27d) hydroxy or (27e) halogen; (28) quinolinyloxy, optionally substituted with (28a) alkyl of from one to six carbon atoms, (28b) haloalkyl of from one to six carbon atoms, (28c) alkoxy of from one to six carbon atoms, (28d) hydroxy or (28e) halogen; (29) isoquinolinyloxy, optionally substituted with (29a) alkyl of from one to six carbon atoms, (29b) haloalkyl of from one to six carbon atoms, (29c) alkoxy of from one to six carbon atoms, (29d) hydroxy or (29e) halogen; (30) pyazinyloxy, optionally substituted with (30a) alkyl of from one to six carbon atoms, (30b) haloalkyl of from one to six carbon atoms, (30c) alkoxy of from one to six carbon atoms, (30d) hydroxy or (30e) halogen; (31) pyrimidinyloxy, optionally substituted with (31a) alkyl of from one to six carbon atoms, (31b) haloalkyl of from one to six carbon atoms, (31c) alkoxy of from one to six carbon atoms, (31d) hydroxy or (31e) halogen.

Continuing the definition of A, the group is additionally selected from (n) 2- or 3-furyl, optionally substituted with (n1) alkyl of from one to six carbon atoms, (n2) haloalkyl of from one to six carbon atoms, (n3) halogen, (n4) phenyl, optionally substituted with (n4a) alkyl of from one to six carbon atoms, (n4b) haloalkyl of from one to six carbon atoms, (n4c) alkoxy of from one to six carbon atoms, (n4d) hydroxy or (n4e) halogen, (n5) phenoxy, optionally substituted with (n5a) alkyl of from one to six carbon atoms, (n5b) haloalkyl of from one to six carbon atoms, (n5c) alkoxy of from one to six carbon atoms, (n5d) hydroxy or (n5e) halogen, (n6) phenylthio, optionally substituted with (n6a) alkyl of from one to six carbon atoms, (n6b) haloalkyl of from one to six carbon atoms, (n6c) alkoxy of from one to six carbon atoms, (n6d) hydroxy or (n6e) halogen, (n7) 2- 3-, or 4-pyridyl, optionally substituted with (n7a) alkyl of from one to six carbon atoms, (n7b) haloalkyl of from one to six carbon atoms, (n7c) alkoxy of from one to six carbon atoms, (n7d) hydroxy or (n7e) halogen, (n8) 2-, 3-, or 4-pyridyloxy, optionally substituted with (n8a) alkyl of from one to six carbon atoms, (n8b) haloalkyl of from one to six carbon atoms, (n8c) alkoxy of from one to six carbon atoms, (n8d) hydroxy or (n8e) halogen; (o) benzo[b]furyl, optionally substituted with (o1) alkyl of from one to six carbon atoms, (o2) haloalkyl of from one to six carbon atoms; (o3) alkoxyl of from one to six carbon atoms, (o4) hydroxy, or (o5) halogen; (p) 2-or 3-thienyl, optionally substituted with (p1) alkyl of from one to six carbon atoms, (p2) haloalkyl of from one to six carbon atoms, (p3) alkoxyl of from one to six carbon atoms, (p4) halogen, (p5) phenyl, optionally substituted with (p5a) alkyl of from one to six carbon atoms, (p5b) haloalkyl of from one to six carbon atoms, (p5c) alkoxy of from one to six carbon atoms, (p5d) hydroxy or (p5e)

halogen, (p6) phenoxy, optionally substituted with (p6a) alkyl of from one to six carbon atoms, (p6b) haloalkyl of from one to six carbon atoms, (p6c) alkoxy of from one to six carbon atoms, (p6d) methylenedioxy, (p6e) phenyl, (p6f) phenoxy, (p6g) hydroxy, (p6h) halogen, (p6i) cyano, (p6j) trifluoromethyl, (p7) thiophenoxy, optionally substituted with (p7a) alkyl of from one to six carbon atoms, (p7b) haloalkyl of from one to six carbon atoms, (p7c) alkoxy of from one to six carbon atoms, (p7d) hydroxy or (p7e) halogen, (p8) 1- or 2-naphthyloxy, optionally substituted with (p8a) alkyl of from one to six carbon atoms, (p8b) haloalkyl of from one to six carbon atoms, (p8c) alkoxy of from one to six carbon atoms, (p8d) hydroxy or (p8e) halogen, (p9) 2- 3-, or 4-pyridyl, optionally substituted with (p9a) alkyl of from one to six carbon atoms, (p9b) haloalkyl of from one to six carbon atoms, (p9c) alkoxy of from one to six carbon atoms, (p9d) hydroxy, (p9e) mercapto, or (p9f) halogen, (p10) 2-, 3-, or 4-pyridyloxy, optionally substituted with (p10a) alkyl of from one to six carbon atoms, (p10b) haloalkyl of from one to six carbon atoms, (p10c) alkoxy of from one to six carbon atoms, (p10d) hydroxy, (p10e) mercapto, or (p10f) halogen, (p11) 2- or 3-furyl, or (p12) 2- or 3-thienyl; (q) benzo[b]thienyl, optionally substituted with (q1) alkyl of from one to six carbon atoms, (q2) haloalkyl of from one to six carbon atoms; (q3) alkoxyl of from one to six carbon atoms, (q4) hydroxy, (q5) halogen; or (q6) phenoxy, optionally substituted with (q6a) alkyl of from one to six carbon atoms, (q6b) haloalkyl of from one to six carbon atoms, (q6c) alkoxyl of from one to six carbon atoms, (q6d) hydroxyl, or (q6e) halogen.

In another embodiment of the present invention, there are provided pharmaceutical compositions which comprise a therapeutically effective amount of compound as defined above in combination with a pharmaceutically acceptable carrier.

In a further embodiment, the present invention provides a method of inhibiting leukotriene biosynthesis in a host mammal in need of such treatment comprising administering to a mammal in need of such treatment a therapeutically effective amount of a compound as defined above.

In further embodiments of the present invention there are provided a novel synthetic intermediate and process for the preparation of lipoxygenase inhibiting compounds of the present invention of the formula

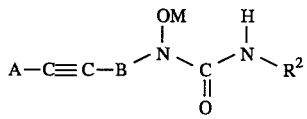

In particular, the intermediate comprises a bis-carboxyhydroxylamine reagent of the formula

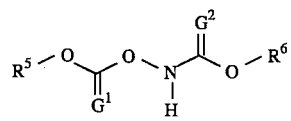

where $G^1$ and $G^2$ are sulfur or oxygen, $R^5$ is selected from phenyl, optionally substituted with alkyl of from one to six carbon atoms, alkoxy of from one to six carbon atoms, nitro or halogen; phenylalkyl in which the alkyl portion is of from one to six carbon atoms and the phenyl ring is optionally substituted with alkyl of from one to six carbon atoms, alkoxy of from one to six carbon atoms, nitro or halogen;

$C_1$–$C_8$ alkyl, 2,2,2-trichloroethyl, and 2,2,2-trifluoroethyl, and $R^6$ is phenyl, optionally substituted with alkyl of from one to six carbon atoms, alkoxy of from one to six carbon atoms, nitro or halogen. Preferred reactants are N,O-bis(carbophenoxy)-hydroxylamine ($R^5$=$R^6$=phenyl and $G^1$=$G^2$=O) referred to as CPHA, and N-(carbo-phenoxy)-O-(carbo-tert-butoxy)hydroxylamine, referred to as PTBHA.

The process comprises the steps of (a) reacting a starting alcohol of the structure A—C≡C—B—OH, where A and B are as defined above, with a mixture of triphenylphosphine, an azodicarboxylate diester, and the novel bis-carboxyhydroxylamine reagent described above to provide an intermediate acetylenic bis-adduct of the structure

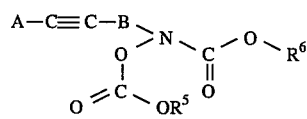

where A, B, $R^5$ and $R^6$ are as defined above, and (b) subsequently converting the product of step (a) by reaction with ammonia, ammonium hydroxide or an amine of the structure $R^2NH_2$ to an N-hydroxyurea of the fomula

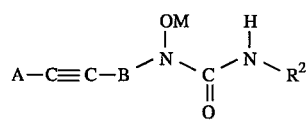

where A, B, M and $R^2$ are as defined above.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

"Alkylamino" and "dialkylamino" refer, respectively, to one or two alkyl groups, as defined above, attached to the parent molecular moiety through a nitrogen atom and are represented by methyl amino, dimethylamino, ethyl- and diethylamino, methylethylamino, and the like.

The term "cycloallcyl" denotes a monovalent group derived from a monocyclic or bicyclic sainted carbocyclic ring compound by the removal of a single hydrogen atom. Examples include cyclopropyl, cyclobutyl, cycopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocaren containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynyl" refers to a divalent group derived by the removal of two hydrogen atoms from a straight or branched chain acyclic hydrocarbon group containing a carbon-carbon triple bond.

The term "alkanoyl" represents an alkyl group, as deemed above, attached to the parent molecular moiety through a carbonyl group. Alkanoyl groups are exemplified by acetyl, propionyl, butanoyl and the like.

"Alkanoylamino" refers to an alkanoyl group, as defined above, attached to the parent molecular moiety through an amino group and is represented by such groups as acetylamino, propionylamino, and the like.

The term "N-alkanoyl-N-alkylamino" denotes a nitrogen atom attached to the parent molecular moiety which nitrogen atom bears an alkanoyl group and an alkyl group, as those terms are defined above. N-alkanoyl-N-alkylamino groups are exemplified by N-acetyl-N-methylamino, N-propionyl-N-ethylamino, and the like.

"Alkylaminocarbonyl" and "dialkylaminocarbonyl" represent, respectively, an alkylamino or dialkylamino group attached to the parent molecular moiety through a carbonyl group. Such groups include, for example methylaminocarbonyl, ethylaminocarbonyl, dimethylaminocarbonyl, diethylaminocarbonyl, methylethylaminocarbonyl, and the like.

The term "alkoxycarbonyl" represents an ester group; i.e. an alkoxy group, attached to the parent molecular moiety through a carbonyl group such as methoxycarbonyl, ethoxycarbonyl, and the like.

The term "carbocyclic aryl" denotes a monovalent carbocyclic ring group derived by the removal of a single hydrogen atom from a monocyclic or bicyclic fused or non-fused ring system obeying the "4n+2π electron" or Huckel aromaticity rule. Examples of carbocyclic aryl groups include phenyl, and 1- and 2-naphthyl, and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moiety through a sulfur atom and thence through an alklyene group and are typified by phenylthiomethyl, 1- and 2-naphthylthioethyl and the like.

The term "carbocyclic arylaminoalkyl" refers to a carbocyclic aryl group as defined above, attached to the parent molecular moiety through a —NH-alkylene- group and is exemplified by phenylaminomethyl, phenylaminoethyl, 1- and 2-naphthylaminomethyl and the like.

"[N-(carbocyclic aryl)-N-alkylamino]alkyl" refers to a group attached to the parent molecular moiety through an aminoalkyl group in which a carbocyclic aryl group, as defined above, and an alkyl group, as defined above, are attached to the nitrogen atom and includes such representative examples as (N-phenyl-N-methylamino)methyl, (N-phenyl-N-ethylamino)methyl, (N-(1-naphthyl)-N-propylamino)ethyl and the like.

"[N-(carbocyclic arylalkyl)amino]alkyl" denotes a carbocyclic arylalkyl group, as defined above, attached to the parent molecular moiety through an aminoalkyl group and is typified by [N-(phenylmethyl)amino]methyl, [N-(phenylethyl)amino]methyl, (1- and (2-naphthylmethylamino)methyl and the like.

"[N-(carbocyclic arylalkyl)-N-alkylamino]alkyl" refers to a group attached to the parent molecular moiety through an aminoalkyl group and having attached to the nitrogen atom thereof a carbocyclic arylalkyl group, as defined above, and an alkyl group. [N-(carbocyclic arylallcyl)-N-alkylamino] alkyl groups are represented by [N-phenylmethyl-N-methylamino]methyl, [N-phenylethyl-N-methylamino]propyl, [N-(1-naphthylmethyl)-N-ethylamino]methyl, and the like.

The term "metabolically cleavable group" denotes a group which is cleaved in vivo to yield the parent molecule of the structural formulae indicated above wherin M is hydrogen. Examples of metabolically clearable groups include —COR, —COOR, —CONRR and —CH$_2$OR radicals where R is selected independently at each occurrence from alkyl, trialkylsilyl, phenyldialkylsilyl, diphenylalkylsilyl, carbocyclic aryl or carbocyclic aryl substituted with one or more of $C_1$–$C_4$ alkyl, halogen, hydroxy or $C_1$–$C_4$ alkoxy. Specific examples of representative metabolically cleavable groups include acetyl, methoxycarbonyl, benzoyl, methoxymethyl and trimethylsilyl groups.

Preferred Embodiments

Preferred compounds of the present invention are N-hydroxy ureas and their salts having the structure

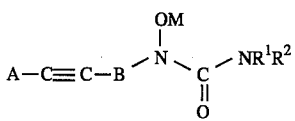

where the values of A, B, M, $R^1$ and $R^2$ are as defined above. Particular compounds falling within the scope of the present invention include, but are not limited to:

N-hydroxy-N-(4-cyclopropyl-3-butyn-2-yl)urea
N-hydroxy-N-(4-trans-(2-cyclopropyl)cyclopropyl-3-butyn-2-yl)urea
N-hydroxy-N-4-(1-trans-(4-methylphenoxy)phenyl) cycloprop-2-yl-3-butyn-2-yl)urea
N-hydroxy-N-3-(1-trans-(4-methylphenoxy)phenyl) cycloprop-2-yl-2-propynyl) urea
N-hydroxy-N-(4-cyclobutyl-3-butyn-2-yl)urea
N-hydroxy-N-(4-cyclopentyl-3-butyn-2-yl)urea
N-hydroxy-N-[4-(3-{2-phenylethynyl}phenyl)-3-butyn-2-yl]urea
N-hydroxy-N-[4-(3-{4-fluorophenoxy}-6-methoxyphenyl)-3-butyn-2-yl]urea
N-hydroxy-N-[4-(3-{4-fluorophenoxy}-4-methoxyphenyl)-3-butyn-2-yl]urea
N-hydroxy-N-4-(3-(1-phenylethoxy)phenyl)-3-butyn-2-yl)urea
N-hydroxy-N-4-(2-(4-chlorothiophenoxy)phenyl)-3-butyn-2-yl)urea
N-hydroxy-N-(4-cyclohexyl-3-butyn-2-yl)urea;
N-hydroxy-N-(4-cyclohexen-1-yl-3-butyn-2-yl)urea;
N-hydroxy-N-(3-phenyl-2-propynyl)urea;
N-hydroxy-N-(4-phenyl-3-butyn-2-yl)urea;
N-hydroxy-N-(5-phenyl-3-pentyn-2-yl)urea;
N-hydroxy-N-(6-phenyl-3-hexyn-2-yl)urea;
N-hydroxy-N-(7-phenyl-3-heptyn-2-yl)urea;
N-hydroxy-N-[4-(4-methylphenyl)-3-butyn-2-yl]urea;
N-hydroxy-N-[4-(4-ethylphenyl)-3-butyn-2-yl]urea;
N-hydroxy-N-[4-[4-(1-methylethyl)phenyl]-3-butyn-2-yl]urea;
N-hydroxy-N-[4-(4-methoxyphenyl )-3-butyn-2-yl]urea;
N-hydroxy-N-[4-(4-fluorophenyl)-3-butyn-2-yl]urea;
N-hydroxy-N-[4-(4-chlorophenyl )-3-butyn-2-yl]urea;
N-hydroxy-N-[4-(4-bromophenyl)-3-butyn-2-yl]urea;
N-hydroxy-N-[3-(3-phenoxyphenyl)-2-propynyl]urea;
N-hydroxy-N-[4-(3-phenoxyphenyl)-3-butyn-2-yl]urea;
N-hydroxy-N-[4-(4-phenoxyphenyl)-3-butyn-2-yl]urea;
N-hydroxy-N-[5-(3-phenoxyphenyl)-3-pentyn-2-yl]urea;
N-hydroxy-N-[3-(3-(4-methylphenoxy)phenyl)-2-propynyl]urea;
N-hydroxy-N-[4-(3-(4-methylphenoxy)phenyl)-3-butyn-2-yl]urea;
N-hydroxy-N-[3-(3-(4-methoxyphenoxy)phenyl)-2-propynyl]urea;
N-hydroxy-N-[4-(3-(4-methoxyphenoxy)phenyl)-3-butyn-2-yl]urea;
N-hydroxy-N-[4-(3-(4-methylthiophenoxy)phenyl)-3-butyn-2-yl]urea;
N-hydroxy-N-[3-(3-(4-fluorophenoxy)phenyl)-2-propynyl]urea;
N-hydroxy-N-[4-(3-(4-fluorophenoxy)phenyl)-3-butyn-2-yl]urea;
[+]-N-hydroxy-N-[4-(3-(4-fluorophenoxy)phenyl)-3-butyn-2-yl]urea;
[–]-N-hydroxy-N-[4-(3-(4-fluorophenoxy)phenyl)-3-butyn-2-yl]urea;
N-hydroxy-N-[4-(3-(4-chlorophenoxy)phenyl)-3-butyn-2-yl ]urea;
N-hydroxy-N-[4-(3-(4-fluoro-3-methylphenoxy)phenyl)-3-butyn-2-yl]urea;
N-hydroxy-N-[4-(3-(3-fluoro-4-methylphenoxy)phenyl)-3-butyn-2-yl]urea;
N-hydroxy-N-[4-(3-benzyloxyphenyl)-3-butyn-2-yl] urea;
N-hydroxy-N-[4-(4-benzyloxyphenyl)-3-butyn-2-yl] urea;
N-hydroxy-N-(4-phenoxy-2-butynyl)urea;
N-hydroxy-N-(5-phenoxy-3-pentyn-2-yl)urea;
N-hydroxy-N-[4-(3-phenoxyphenoxy )-2-butynyl]urea;
N-hydroxy-N-[4-(6-methoxynaphth-2-yl)-3-butyn-2-yl] urea;
N-hydroxy-N-(5-phenylthio-3-pentyn-2-yl)urea;
N-hydroxy-N-[5-((N-methyl-N-benzyl)amino)-3-pent-2-yl]urea.
N-hydroxy-N-[3-(3-(2-pyridinyloxy)phenyl)-2-propyn-1-yl]urea;
N-hydroxy-N-[3-(3-(3-pyridinyloxy)phenyl)-2-propyn-1-yl]urea;
N-hydroxy-N-[4-(3-(2-pyridinyloxy)phenoxy)-2-butynyl]urea;
N-hydroxy-N-[4-(3-(3-pyridinyloxy)phenoxy)-2-butynyl]urea;
N-hydroxy-N-[4-(3-(2-pyridinyloxy)phenyl)-3-butyn-2-yl]urea;
N-hydroxy-N-[4-(3-(2-pyridinyloxy)phenyl)-3-butyn-2-yl]-N'-methylurea;
N-hydroxy-N-[4-(3-(3-pyridinyloxy)phenyl)-3-butyn-2-yl]urea;
N-hydroxy-N-[4-(3-(4-pyridinyloxy)phenyl)-3-butyn-2-yl]urea;
N-hydroxy-N-[5-(3-(2-pyridinyloxy)phenyl)-4-pentyn-3-yl]urea;
N-hydroxy-N-[5-(3-(4-pyridinyloxy)phenoxy)-3-pentyn-2-yl]urea;
N-hydroxy-N-[5-(3-(3-pyridinyloxy)phenoxy)-3-pentyn-2-yl]urea;
N-hydroxy-N-[5-(3-(2-pyridinyloxy)phenoxy)-3-pentyn-2-yl]urea;
N-hydroxy-N-[6-(3-(2-pyridinyloxy)phenyl)-3-hexyn-2-yl]-urea;
N-hydroxy-N-[4-(3-(6-methoxypyridin-2-yloxy)phenyl)-3-butyn-2-yl]urea;
N-hydroxy-N-[4-(3-(6-methylpyridin-2-yloxy)phenyl)-3-butyn-2-yl]urea;
N-hydroxy-N-[4-(3-(6-chloropyridin-2-yloxy)phenyl)-3-butyn-2-yl]urea;
N-hydroxy-N-[4-(3-(2-thiazolyloxy)phenyl)-3-butyn-2-yl]urea;
N-hydroxy-N-[4-(3-{2-thienyloxy)phenyl)-3-butyn-2-yl] urea;

N-hydroxy-N-[4-(3-{3-thienyloxy)phenyl)-3-butyn-2-yl]urea;
N-hydroxy-N-[4-(3-{3-pyridyloxy}-6-methoxyphenyl)-3-butyn-2-yl]urea;
N-hydroxy-N-[4-(3-(2-2-pyridyloxy)phenyl)-3-butyn-2-yl]urea;
N-hydroxy-N-[3-(1-trans-(2-(3-pyridyloxyphenyl)cycloprop-2-yl-2-propynyl]urea;
N-hydroxy-N-[4-(3-{2-furyl}phenyl)-3-butyn-2-yl]urea;
N-hydroxy-N-[4-(3-{1-benzoxazolyoxy}phenyl)-3-butyn-2-yl]urea;
N-hydroxy-N-[4-(3-(4-isoquinonyloxy)phenyl)-3-butyn-2-yl]urea;
N-hydroxy-N-[4-(3-(2-quinonylmethoxy)phenyl)-3-butyn-2-yl]urea;
N-hydroxy-N-[4-(3-(2-quinonyloxy)phenyl)-3-butyn-2-yl]urea;
N-hydroxy-N-[4-(3-pyrazinyloxy)phenyl)-3-butyn-2-yl]urea;
N-hydroxy-N-[4-(3-(pyrimid-2-yloxy)phenyl)-3-butyn-2-yl]urea;
N-hydroxy-N-[4-(2-furyl)-3-butyn-2-yl]urea;
N-hydroxy-N-[4-(3-furyl )-3-butyn-2-yl]urea;
N-hydroxy-N-[4-(5-methoxyfur-2-yl)-3-butyn-2-yl]urea;
N-hydroxy-N-[4-(5-n-butoxyfur-2-yl)-3-butyn-2-yl]urea;
N-hydroxy-N-[4-(4-bromo-2-furyl)-3-butyn-2-yl]urea;
N-hydroxy-N-[4-(5-phenyl-2-furyl)-3-butyn-2-yl]urea;
N-hydroxy-N-[4-(5-phenoxy-2-furyl)-3-butyn-2-yl]urea;
N-hydroxy-N-[4-(5-(2-naphthoxy)-2-furyl)-3-butyn-2-yl]urea;
N-hydroxy-N-[4-(5-(4-methylphenoxy)-2-furyl)-3-butyn-2-yl]urea;
N-hydroxy-N-[4-(5-(4-n-butylphenoxy)-2-furyl)-3-butyn-2-yl]urea;
N-hydroxy-N-[4-(5-(4-t-butylphenoxy)-2-furyl)-3-butyn-2-yl]urea;
N-hydroxy-N-[4-(5-(2-methyl-4-fluorophenoxy)-2-furyl)-3-butyn-2-yl}urea;
N-hydroxy-N-{4-[5-(3-methyl-4-fluorophenoxy)-2-furyl]-3-butyn-2-yl}]urea;
N-hydroxy-N-[4-(5-(4-methoxyphenoxy)-2-furyl)-3-butyn-2-yl]urea;
N-hydroxy-N-[4-(5-(4-n-butoxyphenoxy)-2-furyl)-3-butyn-2-yl]urea;
N-hydroxy-N-[4-(5-(3,4-methylenedioxyphenoxy)-2-furyl)-3-butyn-2-yl]urea;
N-hydroxy-N-[4-(5-(4-phenylphenoxy)-2-furyl)-3-butyn-2-yl]urea;
N-hydroxy-N-[4-(5-(4-phenoxyphenoxy)-2-furyl)-3-butyn-2-yl]urea;
N-hydroxy-N-[4-(5-(3-phenoxyphenoxy)-2-furyl)-3-butyn-2-yl]urea;
N-hydroxy-N-[3-(5-(4-fluorophenoxy)-2-furyl)-2-propynyl]urea;
N-hydroxy-N-[4-(5-(2-fluorophenoxy)-2-furyl)-3-butyn-2-yl]urea;
N-hydroxy N-[4-(5-(3-fluorophenoxy)-2-furyl)-3-butyn-2-yl]urea;
N-hydroxy-N-[4-(2-(4-fluorophenoxy)-2-furyl)-3-butyn-2-yl]urea;
N-hydroxy-N-[4-(5-(4-fluorophenoxy)-2-furyl])3-butyn-2-methyl-2-yl]urea;
N-hydroxy-N-[4-(5-((4-fluorophenoxy)fur-2-yl)-2-furyl)-3-butyn-2-yl]urea;
N-hydroxy-N-[4-(5-(2,4-difluorophenoxy)-2-furyl)-3-butyn-2-yl]urea;
N-hydroxy-N-[4-(5-(2,6-difluorophenoxy)-2-furyl)-3-butyn-2-yl]urea;
N-hydroxy-N-[4-(5-(2,4-difluorophenoxy)-2-furyl)-3-butyn-2-yl]urea;
N-hydroxy-N-[4-(5-(4-trifluoromethylphenoxy)-2-furyl)-3-butyn-2-yl]urea;
N-hydroxy-N-[4-(5-(4-(4-fluorophenylmethyl)phenoxy)-2-furyl)-3-butyn-2-yl]urea;
N-hydroxy-N-{4-[5-(4-chlorophenoxy)-2-furyl]-3-butyn-2-yl }urea;
N-hydroxy-N-{4-[5-(2,4-dichlorophenoxy)-2-furyl]-3-butyn-2-yl}urea;
N-hydroxy-N-{4-[5-(2-chloro-3-hydroxyethyl-4-fluorophenoxy)-2-furyl]-3-butyn-2-yl }urea;
N-hydroxy-N-[4-(5-(4-bromophenoxy)-2-furyl)-3-butyn-2-yl]urea;
N-hydroxy-N-[4-(5-(4-cyanophenoxy)-2-furyl)-3-butyn-2-yl]urea;
N-hydroxy-N-[4-(2-thiophenoxy-2-furyl)-3-butyn-2-yl]urea;
N-hydroxy-N-[4-(3-thiophenoxy-2-furyl)-3-butyn-2-yl]urea;
N-hydroxy-N-[4-(5-thiophenoxy-2-furyl)-3-butyn-2-yl]urea;
N-hydroxy-N-[4-(5-(2-methylthiophenoxy)-2-furyl)-3-butyn-2-yl]urea;
N-hydroxy-N-[4-(5-{fur-2-yl)-2-furyl)-3-butyn-2-yl]urea;
N-hydroxy-N-[4-(5-(thien-2-yl)-2-furyl)-3-butyn-2-yl]urea;
N-hydroxy-N-[4-(5-(2-mercaptopyridyl)-2-furyl)-3-butyn-2-yl]urea;
N-hydroxy-N-[4-(5-(5-chloro-3-pyridyloxy)-2-furyl)-3-butyn-2-yl]urea;
N-hydroxy-N-[4-(5-(3-pyridyloxy)-2-furyl)-3-butyn-2-yl]urea;
N-hydroxy-N-4-(5-(6-methyl-3-pyridyloxy)-2-furyl)-3-butyn-2-yl]urea;
N-hydroxy-N-4-(benzo[b]fur-2-yl)-3-butyn-2-yl)urea;
N-hydroxy-N-[4-(5-(4-fluorophenoxy)benzo[b]fur-2-yl)-3-butyn-2-yl]urea;
N-hydroxy-N-[4-(7-(4-fluorophenoxy)benzo[b]fur-2-yl)-3-butyn-2-yl]urea;
N-hydroxy-N-[4-(5-methylthien-2-yl)-3-butyn-2-yl]urea;
N-hydroxy-N-[4-(5-burylthien-2-yl)-3-butyn-2-yl]urea;
N-hydroxy-N-[4-(5-methoxythien-2-yl)-3-butyn-2-yl]urea;
N-hydroxy-N-[4-(5-bromothien-2-yl)-3-butyn-2-yl]urea;
N-hydroxy-N-[4-(5-(4-methoxyphenoxy)thien-2-yl)-3-butyn-2-yl]urea;
N-hydroxy-N-[4-(5-phenoxy)thien-2-yl)-3-butyn-2-yl]urea;
N-hydroxy-N-[4-(5-thiophenoxy)thien-2-yl)-3-butyn-2-yl]urea;
N-hydroxy-N-[4-(4-(4-fluorophenoxy)thien-2-yl)-3-butyn-2-yl]urea;
N-hydroxy-N-[4-(5-(4-fluorothiophenoxy)thien-2-yl)-3-butyn-2-yl]urea;

N-hydroxy-N-[4-(5-(5-bromothien-2-yl)thien-2-yl)-3-butyn-2-yl]urea;

N-hydroxy-N-[4-(5-(thien-2-yl)thien-2-yl)-3-butyn-2-yl]urea; and

N-hydroxy-N-[4-(2-benzo[b]thien-2-yl)-3-butyn-2-yl]urea.

Additionally, the present invention contemplates compounds having the names above wherein the N-hydroxy hydrogen atom is replaced by a pharmaceutically acceptable cation, or a pharmaceutically acceptable metabolically cleavable group, as defined above.

Particularly preferred is the compound having the name N-hydroxy-N-{4-[5-(4-fluorophenoxy)-2-furyl]-3-butyn-2yl}urea, its enantiomers and mixtures thereof, and its pharmaceutically acceptable salts.

Certain compounds of this invention may exist in stereoisomeric forms by virtue of the presence of one or more chiral centers. The present invention contemplates all such stereoisomers, including R- and S-enantiomers, diastereomers, and mixtures thereof as falling within the scope of the invention. If a particular enantiomer is desired, it may be prepared by chiral synthesis or by derivatization with a chiral auxiliary where the resulting diastereomeric mixture is separated and the auxiliary group cleaved to provide the pure desired enantiomers. Alternatively, where the molecule contains a basic functional group such as amino or an acidic functional group such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

Certain compounds of the present invention may contain a basic functional group such as amino, alkylamino, or dialkylamino and are thus capable of forming salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, rosylate, citrate, maleate, fumarate, succinate, tartrate, naphthylate, mesylate, glucoheptonate, lactiobionate, laurylsulphonate salts and the like. (See, for example S. M. Berge, et at., "Pharmaceutical Salts," *J. Pharm. Sci.*, 66: 1–19 (1977) which is incorporated herein by reference.)

In other cases, the compounds may contain one or more acidic functional groups such as carboxyl and the like and are capable of forming salts with pharmaceutically acceptable bases. The term "pharmaceutically acceptable salts" in these instances refers to the relatively non-toxic, inorganic and organic base addition salts of compounds of the present invention. These salts can be likewise prepared in situ during the final isolation and purification of the compounds or by separately reacting the purified compound in its free acid form with a suitable base such as the hydroxide, carbonate or bicarbonate of a pharmaceutically acceptable metal cation or with ammonia, or an organic primary, secondary, or tertiary amine. Representative alkali or alkaline earth salts include the lithium; sodium, potassium, calcium, magnesium and aluminum salts and the like. Representative organic amines useful for the formation of base addition salts include ethylamine, diethylamine, ethylenediamine, ethanolnine, diethanolamine, piperazine, and the like. (See, for example S. M. Berge, et al., "Pharmaceutical Salts," *J. Pharm. Sci.*, 66: 1–19 (1977) which is incorporated herein by reference.)

Lipoxygenase Inhibition Determination

Assays to determine 5-lipoxygenase inhibitory activity of representative compounds of the present invention were performed in 200 mL incubations containing the 20,000×g supernatant from 1.5 million homogenized RBL-1 cells and various concentrations of the test compound. Reactions were initiated by addition of radiolabeled arachidonic acid and terminated by acidification and ether extraction. Reaction products were separated from nonconverted substrate by thin layer chromatography and measured by liquid scintillation spectroscopy. All incubations are performed in triplicate. Inhibition of 5-lipoxygenase activity was calculated as the ratio of the mount of product formed in the presence and absence of inhibitor. $IC_{50}$ values (concentration of compound producing 50% enzyme inhibition) were calculated by linear regression analysis of percentage inhibition versus log inhibitor concentration plots. (Dyer, R. D.; Haviv, F.; Hanel, A. M.; Bornemier, D. A.; Carter, G. W. Fed. Proc., *Fed. Am. Soc. Exp. Biol.* 1984, 43, 1462A). Results for compounds of the foregoing examples are indicated in Table 1.

TABLE 1

In Vitro Inhibitory Potencies of Compounds of this Invention Against 5-Lipoxygenase from RBL-1 20,000xg Supernatant

| Example | $IC_{50}$ ($10^{-6}$ M) |
| --- | --- |
| 1 | 2.4 |
| 3 | 0.1 |
| 4 | 0.4 |
| 5 | 3.6 |
| 6 | 0.2 |
| 7 | 0.13 |
| 8 | 1.9 |
| 9 | 1.2 |
| 11 | 0.7 |
| 12 | 0.3 |
| 13 | 0.3 |
| 14 | 1.7 |
| 15 | 3.3 |
| 16 | 0.1 |
| 17 | 0.8 |
| 18 | 0.5 |
| 19 | 0.4 |
| 20 | 1.1 |
| 21 | 2.1 |
| 22 | 0.4 |
| 23 | 0.5 |
| 24 | 0.3 |
| 25 | 0.4 |
| 26 | 0.9 |
| 27 | 0.7 |
| 28 | 1.4 |
| 29 | 0.8 |
| 30 | 2.1 |
| 31 | 6.2 |
| 32 | 5.9 |
| 33 | 0.5 |
| 34 | 7.0 |
| 35 | 0.4 |
| 36 | 0.6 |
| 37 | 2.0 |
| 39 | 0.6 |
| 40 | 0.5 |
| 41 | 3.5 |
| 42 | 0.5 |
| 43 | 0.3 |

TABLE 1-continued

In Vitro Inhibitory Potencies of Compounds of this Invention Against 5-Lipoxygenase from RBL-1 20,000xg Supernatant

| Example | $IC_{50}$ ($10^{-6}$ M) |
|---|---|
| 44 | 0.4 |
| 45 | 0.2 |
| 46 | 1.2 |
| 47 | 0.9 |
| 55 | 0.9 |
| 56 | 0.3 |
| 57 | 0.2 |
| 58 | 0.2 |
| 59 | 0.2 |
| 62 | 0.3 |
| 64 | 0.6 |
| 65 | 0.2 |
| 66 | 0.5 |
| 67 | 0.3 |
| 68 | 0.2 |

Inhibition of Leukotriene Biosynthesis

Inhibition of the biosynthesis of leuktrienes in vivo after oral administration of compound was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by garage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results are presented in Table 2.

TABLE 2

| Example | Percent Inhibition of Leukotrienes | | |
|---|---|---|---|
| | Oral Dose at 200 μmol/kg | Oral Dose at 100 μmol/kg | Oral Dose at 30 μmol/kg |
| 1 | 98 | | |
| 2 | 66 | | |
| 4 | 64 | | |
| 8 | 41 | | |
| 10 | 99 | | |
| 11 | 99 | | |
| 17 | 98 | | |
| 19 | | 82 | |
| 20 | | 89 | |
| 21 | | 90 | |
| 22 | | 86 | |
| 25 | | 69 | |
| 26 | | 78 | |
| 30 | | 95 | |
| 32 | | 97 | |
| 33 | | 99 | |
| 34 | | 96 | |
| 36 | | 99 | |
| 38 | | 100 | |
| 39 | | 96 | |
| 42 | | 66 | |
| 43 | | 98 | |
| 44 | | 99 | |
| 46 | | 98 | |
| 47 | | 99 | |
| 49 | | 98 | |
| 54 | | | 78 |
| 57 | | | 83 |
| 58 | | | 83 |
| 59 | | | 62 |
| 60 | | | 70 |
| 62 | | | 65 |
| 63 | | | 85 |
| 64 | | | 78 |
| 66 | | | 40 |
| 67 | | | 56 |
| 68 | | | 61 |

Preparation of Compounds of this Invention

The compounds of this invention can be prepared from the appropriate starting monosubstituted acetylenes as is illustrated in Scheme 1. The starting monosubstituted acetylenes can be prepared by a number of different approaches as is understood by one skilled in the art. The anion of the starting acetylene is prepared using an appropriate base, and is treated with the nitrone prepared from acetaldehyde and 5-hydroxypentanal oxime. The resulting protected adduct is deprotected in situ, and acetylated with trimethylsilyl isocyanate to provide the desired hydroxyurea products.

Scheme 1

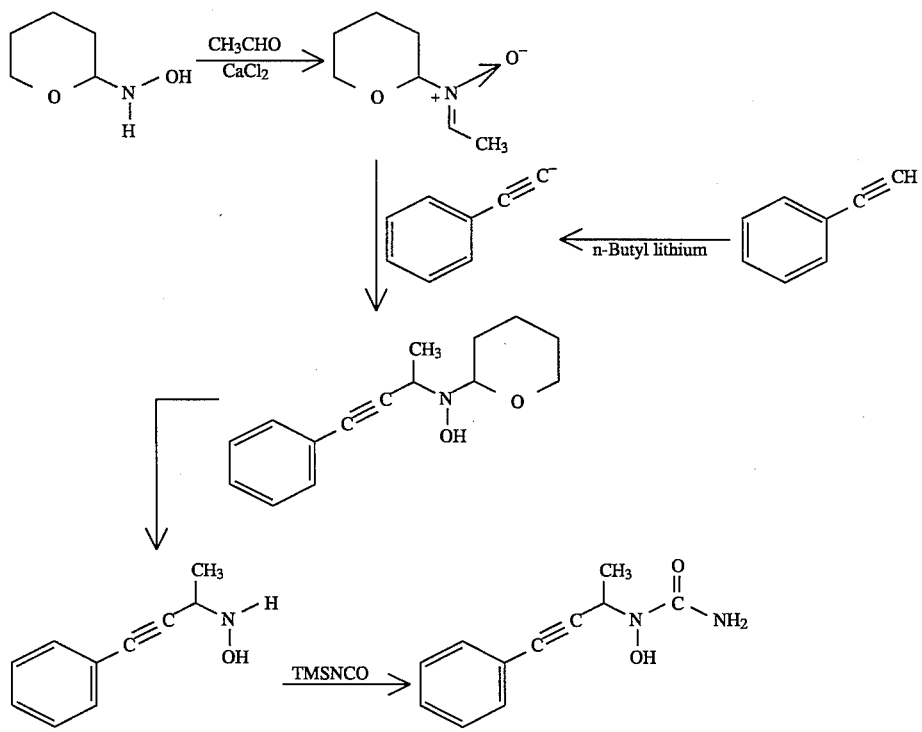

Alteratively, compounds of this invention can be prepared by the general method outlined in Scheme 2. Starting from the appropriate monosubstituted acetylene, the propargylic alcohol can be prepared by metallation followed by reaction with an aldehyde. Subsequent replacement of the alcohol by a protected hydroxylme function can be effected by a modified Mitsunobu process (Lee, B. H.,Miller, M. J., *J. Org. Chem.*, 48, 24–31 (1983) and references therein). Deprotection provides the hydroxylamine intermediate which is convened to the desired N-hydroxyurea.

Scheme 2

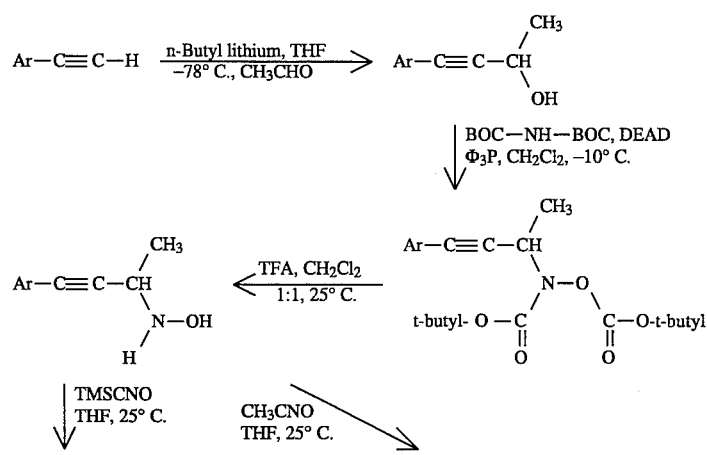

-continued
Scheme 2

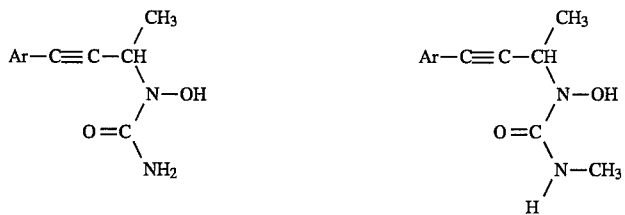

A novel and preferred method to prepare N-hydroxyurea compounds of this invention is outlined in Scheme 3. In this procedure, the starting alcohol A—C≡C—B—OH is treated with a mixture of triphenylphosphine, an azodicarboxylate diester, and the novel bis-carboxyhydroxylamine reagent $R^5OCG^1ONHCG^2OR^6$ (where $R^5$ is selected from aryl, $C_1$-$C_8$ alkyl, aralkyl in which the alkyl portion contains Scheme 3

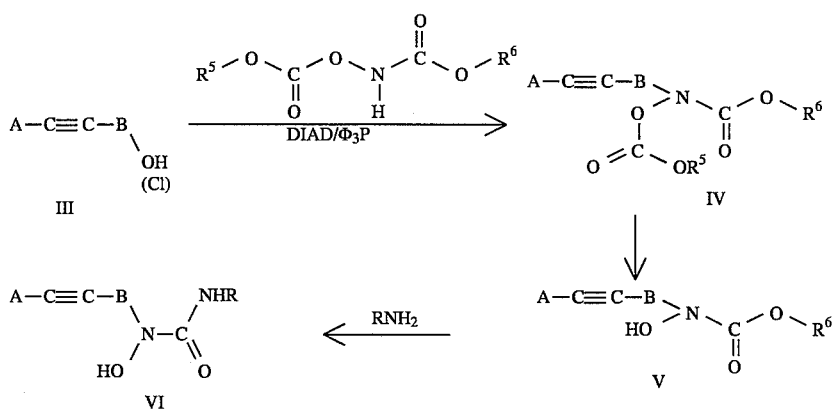

from one to six carbon atoms, and 2,2,2-trichloro- or 2,2,2-trifluoroethyl and $R^6$ is aryl and $G^1$ and $G^2$ are sulfur or oxygen) to provide an intermediate acetylenic bis- adduct which is subsequently converted to hydroxyurea. Preferred reactants are N,O-bis(carbophenoxy)-hydroxylamine ($R^5$=$R^6$=phenyl and $G^1$=$G^2$=O) referred to as CPHA, and N-(carbophenoxy)-O-(carbo-t-butoxy)hydroxylamine, referred to as FTBHA. Other preferred bis-carboxyhydroxylamine reagents useful in this process include the compounds synthesized by the methods detailed in Example 81–86 below, namely N-carbo-(4-nitrophenoxy)-O-carbomethoxyhydroxylamine;

N,O-bis[phenoxy(thiocarbonyl)]hydroxylamine;

N,O-bis[carbo-(4-chlorophenoxy)]hydroxylamine;

N,O-bis[carbo-(4-methylphenoxy)]hydroxylamine;

N-carbo-[phenoxy(thiocarbonyl)]-O-carbomethoxyhydroxylamine; and (N-carbophenoxy-O-carbo-tert-butoxy)hydroxylamine.

The advantages of this novel reagent are principally derived from $R^6$ being equal to aryl. The resulting aryl urethane can be directly converted to N-hydroxyureas by treatment with ammonia, ammonium hydroxide or amines, thereby providing a more efficient procedure to the desired products in good yield and under mild conditions.

The starting acetylenic alcohol, III, is reacted with the bis-carboxyhydroxylamine in an aprotic organic solvent such as tetrahydrofuran, benzene, or methylene chloride in the presence of an azodicarboxylate at a temperature ranging between about –20° C. and room temperature for a period sufficient to effect substantial conversion of the starting material to IV. The intermediate, IV, is treated under standard conditions to cleave the carbonate ($OR^5$) to produce the N-hydroxyurethane, V, which is, in turn, converted by the action of the desired amine, $RNH_2$ (or ammonia where R=H) to the desired product, VI. Alternatively, the starting material may be an acetylenic chloride, III, Alternatively, the starting material may be an acetylenic chloride, III, which is reacted with the biscarboxyhydroxylamine in the presence of an acid scavenger such as triethylamine.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carder such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humnectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capstries, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the mute of administration, the severity of the condition being treated, and the condition and prior medical history of the patient being treated. However, it is within the skid of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Example 1

Preparation of
N-Hydroxy-N-(4-phenyl-3butyn-2-yl)urea

A solution of phenylacetylene (2.2 mL, 20 mmol) at −70° C. in dry THF (20 mL) was treated under nitrogen with n-BuLi (8 mL, 2.5M in hexanes, 20 mmol) and the mixture was stirred for 1 h. A solution of II (prepared by modification of the method reported in *Acta. Chim. Acad. Sci. Hung.* 1958, 14, 333, by the treatment of 5-hydroxypentanal oxime (3.5 g, 30 mmol) with acetaldehyde (3.4 mL, 60 mmol) in the presence of $CaCl_2$ (17.4 g, 130 mmol) at 0° C. in dichloromethane for 6 h, filtered, and dichloromethane evaporated in vacuo at 0° C.) in THF precooled to 0° C. (50 mL) was added to the cold anion (−78° C.) and stirred for 30 min after removal of the cold bath. Ethanol (50 mL) and 6N HCl (5 mL) was added and the mixture was stirred for 0.5 h at room temperature and then poured into 250 mL of water, washed with 3×100 mL of ether, basified with 50 mL of ammonium hydroxide, saturated with salt, extracted with 3×100 mL of ether, dried over potassium carbonate, filtered, and evaporated to provide the crude hydroxylamine intermediate which was purified by column chromatography (ca. 50 g $SiO_2$, using 1:1 ether:hexane) to give the pure hydroxylamine (0.78 g, 4.8 mmol, 24%) mp 62°–4° C. The hydroxylamine in 25 mL of dry THF was treated with trimethylsilyl isocyanate (0.8 mL, 5 mmol) and stirred at room temperature overnight. The solution was poured into 10 mL of a saturated aqueous ammonium chloride solution, stirred for 1.5 h, diluted with 10 mL of water extracted with 3×25 mL of ethyl acetate, dried over magnesium sulfate, filtered, evaporated, and recrystallized from ethyl acetate/hexane to provide 0.67 g of the title compound (16% overall yield). m.p. 141°–142° C. (dec); $^1$H NMR (300 MHz, DMSO-$d_6$) 1.36 (3H, d, J=7 Hz), 5.13 (1H, q, J=7 Hz), 6.55 (2H, br s), 7.37 (5H, m), 9.33 (1H, s). Analysis calculated for $C_{11}H_{12}N_2O_2$: C, 64.69, H, 5.92, N, 13.72; found: C, 64.43, H, 6.00, N, 13.57.

Example 2

Preparation of
N-Hydroxy-N-[4-(6-methoxynaphth-2-yl)-butyn-2-yl]urea

The title compound was prepared according to the procedure of Example 1 using 6-methoxynaphthylacetylene instead of phenylacetylene. m.p. 181°–183° C.; $^1$H NMR (300 MHz, DMSO-$d_6$) 1.39 (3H, d, J=7 Hz), 3.88 (3H, s), 5.16 (1H, m), 6.56 (2H, br s), 7.19 (1H,dd, J=9 Hz, J=2 Hz), 7.33 (1H, d, J=2 Hz), 7.4 (1H, dd, J=9 Hz, J=2 Hz), 7.81 (2H, dd, J=14 Hz, J=9 Hz), 7.95 (1H, s), 9.35 (1H, s); MS 285 (M+H); Analysis calc'd for $C_{16}H_{16}N_2O_3$: C, 67.59; H, 5.67; N, 9.85. Found: C, 67.67; H, 5.72; N, 9.82.

Example 3

Preparation of
N-Hydroxy-N-[4-(3-phenoxyphenyl-3-butyn-2-yl]urea

The title compound was prepared according to the procedure of Example 1 using 3-phenyoxyphenylacetylene instead of phenylacetylene, and the crude hydroxylamine was used without further purification. mp 110°–115° C.; $^1$H NMR (300 MHz, DMSO-$d_6$) 1.33 (d, 3H, J=7 Hz), 5.10 (q, 1H, J=7 Hz), 6.52 (br s, 2H), 6.91 (m, 1H), 7.05 (m, 3H), 7.18 (m, 2H), 7.41 (m, 3H), 9.32 (s, 1H); IR (KBr) 3300, 3200, 1665, 1590, 1580, 1485, 1220 cm$^{-1}$; mass spectrum m/e (rel. intensity),314 (40, M$^+$+NH$_4$), 297 (60, M$^+$+H), 271 (55), 254 (100). Analysis calculated for $C_{17}H_{16}N_2O_3 \cdot \frac{1}{4}H_2O$; C, 67.87, H, 5.53, N, 9.31; found: C, 68.02, H, 5.46, N, 9.19.

Example 4

Preparation of
N-Hydroxy-N-(5-phenylthio-3-pentyn-2-yl)urea

The title compound was prepared according to the procedure of Example 1 using phenyl propargyl sulfide instead of phenylacetylene. NMR (300 MHz, DMSO-$d_6$), 1.21 (3H, d, J=7 Hz), 4.03 (1H, q, J=7 Hz), 4.86 (2H, m), 6.48 (2H, bs), 7.33 (5H, m), 9.21 (1H, s); MS 251 (M+1)$^+$; Analysis calc'd for $C_{12}H_{16}N_2O_2S_1$: C, 57.57; H, 5.63; N, 11.19. Found: C, 57.00; H, 5.77; N, 10.45.

Example 5

Preparation of
N-Hydroxy-N-[5-[(N-methyl-N-benzyl)amino]-3-pentyn-2-yl]urea

The title compound was prepared according to the procedure of Example 1 using N-methyl-N-propargyl benzyl amine instead of phenylacetylene. m.p. 99°–101° C.; NMR (300 MHz, DMSO-$d_6$), 1.31 (3H, d, J=7 Hz), 2.18 (3H, s), 3.20 (2H, d, J=1.5 Hz), 3.48 (2H, s), 4.94 (1H, q, J=7 Hz), 6.53 (2H, s), 7.30 (5H, m), 9.22 (1H, s); MS 262 (M+1)$^+$; Analysis calc'd for $C_{14}H_{19}N_3O_2$: C, 64.34; H, 7.32; N, 16.08. Found: C, 63.99; H, 7.25; N, 15.91.

Example 6

Preparation of N-Hydroxy-N-[4-(3-benzyloxyphenyl)-3-butyn-2-yl]urea

The title compound was prepared according to the procedure of Example 1 using 3-benzyloxyphenylacetylene instead of phenylacetylene, and the crude hydroxylamine was used without further purification. mp 151°-3° C.; $^1$H NMR (300 MHz, DMSO-$d_6$) 1.38 (d, 3H, J=7 Hz), 5.12 (s, 2H), 5.13 (q, 1H, J=7 Hz), 6.54 (br s, 2H), 7.00 (m, 3H), 7.25–7.48 (m, 6H), 9.33 (s, 1H); IR (KBr) 3435, 1680, 1650 cm$^{-1}$; mass spectrum m/e (rel intensity 328 (45, M$^+$+NH$_4$), 311 (100, M$^+$+H), 295 (13), 285 (34), 268 (87), 252 (98) 235 (18). Analysis calculated for $C_{18}H_{18}N_2O_3$: C, 69.66, H, 5.85, N, 9.03; found: C, 70.28, H, 6.13, N, 9.02.

Example 7

Preparation of N-Hydroxy-N-[4-(4benzyloxyphenyl)-3-butyn-2-yl]urea

The title compound was prepared according to the procedure of Example 1 using 4-benzyloxyphenylacetylene instead of phenylacetylene, and the crude hydroxylamine was used without further purification. mp 154°-6° C.; $^1$H NMR (300 MHz, DMSO-$d_6$) 1.34 (d, 3H, J=7 Hz), 5.12 (m, 3H), 6.50 (s, 2H), 6.98 (m, 2H), 7.3–7.5 (m, 7H), 9.78 (s, 1H); IR (KBr) 3360, 2930, 1610 cm$^{-1}$; mass spectrum m/e (rel intensity) 311 (100, M$^+$+H), 295 (12), 268 (14), 252 (22), 235 (43). Analysis calculated for $C_{18}H_{18}N_2O_3 \cdot \frac{1}{2}H_2O$: C, 67.70, H, 6.00, N, 8.77; found: C, 67.61, H, 5.81, N, 8.86

Example 8

Preparation of N-Hydroxy-N-[4-cyclohexyl-3-butyn-2-yl]urea

The title compound was prepared according to the procedure of Example 1 using cyclohexylacetylene instead of phenylacetylene. m p 112°-3° C.; NMR (300 MHz, DMSO-$d_6$), 1.22 (d, 3H, J=7 Hz), 1.20–1.45 (m, 5H), 1.65 (m, 5H), 2.35 (m, 1H), 4.85 (dq, 1H, J=2, 7 Hz), 6.42 (br s, 2H), 9.10 (s, 1H); IR (CHCl$_3$) 3540, 2930, 2235, 1680, 1560 cm$^{-1}$; mass spectrum m/e (rel intensity) 228 (60, M$^+$+NH$_4$), 211 (100, M$^+$ +H), 195 (10). Analysis calculated for $C_{11}H_{18}N_2O_2$: C, 62.83, H, 8.63, N, 13.32; found: C, 62.92, H, 8.73, N, 13.18.

Example 9

Preparation of N-Hydroxy-N-(4-cyclohexen-1-yl-3-butyn-2-yl)urea

The title compound was prepared according to the procedure of Example 1 using 1-cyclohexenylacetylene instead of phenylacetylene. m p 157°-8° C.; NMR (300 MHz, DMSO-$d_6$), 1.27 (d, 3H, J=7 Hz), 1.53 (m, 4H), 1.02 (m, 4H), 4.98 (q, 1H, J= 7 Hz), 5.98 (m, 1H), 6.48 (s, 2H), 9.20 (s, 1H); IR (KBr) 3400, 3160, 2920, 2215, 1640 cm$^{-1}$; mass spectrum m/e (rel intensity) 226 (25, M$^+$+NH$_4$), 209 (100, M$^+$+H), 193 (15), 150 (15), 94 (20). Analysis calculated for $C_{11}H_{16}N_2O_2$; C, 63.44, H, 7.74, N, 13.45; found: C, 63.35, H, 7.70, N, 13.43.

Example 10

Preparation of N-Hydroxy-N-(5-phenoxy-3-pentyn-2-yl)urea

The tide compound was prepared according to the procedure of Example 1 using phenyl propargyl ether instead of phenylacetylene. m.p. 75°–77° C.; NMR (300 MHz, DMSO-$d_6$), 1.26 (3H, d, J=7 Hz), 4.79 (2H s), 4.95 (1H, q, J=7Hz), 6.51 (2H, s), 6.97 (3H, m), 7.3 (2H, m), 9.28 (1 H, s). MS (M+NH$_4$)$^+$252. Analysis calc'd for $C_{12}H_{14}N_2O_3$; C, 61.62; H, 6.023; N, 11.96. Found: C, 61.03, H, 6.04; N, 11.81.

Example 11

Preparation of N-Hydroxy-N-(7-phenyl-3-heptyn-2-yl)urea

The title compound was prepared according to the procedure of Example 1 using 5-phenyl-1-pentyne instead of phenylacetylene. m.p. 78°–81° C.; NMR (300 MHz, DMSO-$d_6$), 1.25 (3H, d, J=7 Hz), 1.69 (2H, m), 2.13 (2H, d, t, J=7 Hz, J=1.5 Hz), 2.65 (2H, t, J=7 Hz), 4.87 (1H, q, J=7 Hz), 6.48 (2H, s), 7.19 (3H, m), 7.29 (2H, m), 9.14 (1H, s); MS (M+1)$^+$247, (M+NH$_4$)$^+$264. Analysis calc'd for $C_{14}H_{18}N_2O_2$; C, 68.26; H, 7.36; N, 11.38. Found: C, 67.79, H, 7.39; N, 11.48.

Example 12

Preparation of N-Hydroxy-N-[4-(4-phenoxyphenyl)-3-butyn-2-yl]urea

The title compound was prepared according to the procedure of Example 1 using 4-phenoxyphenylacethylene instead of phenylacetylene. m.p. 141°–142° C.; NMR (300 MHz, DMSO-$d_6$), 1.35 (3H, d, J=7 Hz), 5.11 (1H, q, J=7Hz), 6.55 (2H, s), 6.95 (2H, d, J=8 Hz), 7.06 (2H, d, J=8Hz), 7.19 (1H, t, J=8Hz), 7.43 (4H, m), 9.33 (1H, s); MS (M+H)$^+$297.

Example 13

Preparation of N-Hydroxy-N-[4-(5-butylthien-2-yl)-3-butyn-2-yl]urea

The title compound was prepared according to the procedure of Example 1 using 5-butyl-2-thienylacetylene instead of phenylacetylene. m.p. 104°–106° C.; NMR (300 MHz, DMSO-$d_6$), 0.89 (3H, t, J=7 Hz), 1.34 (3H, d, J=7Hz), 1.31 (2H, m), 1.57 (2H, m), 2.75 (2H, t, J=7 Hz), 5.12 (1H, q, J=7Hz), 6.55 (2H, s), 6.78 (1H, d, J=7 Hz), 7.05 (1H, d, J=3Hz); MS (M+H)$^+$267, (M+NH$_4$)$^+$284. Analysis calc'd for $C_{13}H_{18}N_2O_2S_1 \cdot \frac{1}{2}H_2O$: C, 56.62; H, 6.81; N, 10.52. Found: C, 56.59, H, 6.40; N, 10.11.

Example 14

Preparation of N-Hydroxy-N-[4-(5-methylthien-2-yl-3-butyn-2-yl]urea

The title compound was prepared according to the procedure of Example 1 using 5-methyl-2-thienylacetylene instead of phenylacetylene. m.p. 132°–134° C.; NMR (300 MHz, DMSO-$d_6$), 1.35 (3H, d, J=7 Hz), 2.41 (3H, s), 5.12 (1H, q, J=7 Hz), 6.55 (2H, s), 6.73 (1H, dd, J=3 Hz, J=1 Hz), 7.04 (1H, d, J=3 Hz), 9.33 (1H, s); MS (M+H)$^+$ 225, (M+NH$_4$)$^+$242.

Example 15

Preparation of N-Hydroxy-N-(4-phenyl-3-butyn-2-yl-N'-methylurea (a) A solution of phenylacetylene (1.02 g, 10.0 mmol) in dry THF (20 mL) at −78° C. was treated with one equivalent of n-BuLi (4.0 mL, 2.5M in hexane, 10.0 mmol) and the mixture was stirred for 30 min under $N_2$. Reaction mixture was then quenched with acetaldehyde (0.6 mL, 11 mmol). To this was added 50 mL of ether, and the organics were washed with water (50 mL) and brine, dried with $MgSO_4$, filtered, evaporated to obtain 1.1 g of corresponding alcohol as yellow color oil.

(b) In a 100 mL round bottom flask, under nitrogen atmosphere were dissolved the crude alcohol (1.1 g, 7.5 mmol) from part (a) above, triphenyl phosphine (2.67 g, 10 mmol) and N-O-bis-t-butyloxycarbonylhydroxylamine (2.23 g, 10 mmol) in freshly dried THF (30 mL). The reaction mixture was cooled to −10° C. and diethylazodicarboxylate (1.6 mL, 11 mmol), was added in freshly dried THF (10 mL) over a 10 min period. The reaction mixture was stirred for 30 min., then the volatiles were removed under vacuum and the resulting residue was chromatographed by column chromatography (silica gel, 10% ethyl acetate:hexane) to obtain 2.38 g of the di-Boc-protected hydroxylamine as a pale yellow syrup.

(c) The di-Boc-protected hydroxylamine derivative (2.38 g) from part (b) above was dissolved in 15 mL of dichloromethane and treated with equal volume of trifluoro acetic acid (15 mL). The reaction was judged complete after 10 min. The reaction mixture was poured into cold sat $NaHCO_3$ (150 mL), extracted with 100 mL of methylene chloride, backwashed with said. $NaHCO_3$, followed by brine, dried with $MgSO_4$, filtered, concentrated to obtain the title hydroxyl amine (1.2 g) as a light brown oil which was used in the next step without further purification.

(d) The crude hydroxylamine (1.1 g, 7.0 mmol) from part (c) above was dissolved in dry THF (20 mL). To the reaction mixture was added methyl isocyanate (0.7 mL, 8.0 mmol) under $N_2$, and the resulting solution was stirred overnight. The reaction mixture was concentrated under vacuum to obtain thick yellow syrup, chilled, dissolved in $Et_2O$ (10 mL), and scratched to induce crystallization. The resulting solid which separated, was filtered, and vacuum dried (820 mg). Recrystallized from EtOAc/hexane to obtain title product (550 mg) as white crystalline material. m.p. 136°–137° C.; NMR (300 MHz, DMSO-$d_6$), 1.36 (3H, d, J=7 Hz), 2.61 (3H, d, J=4 Hz), 5.11 (1H, q, J=7 Hz), 7.12 (1H, q, J=4 Hz), 7.38 (5H, m), 9.28 (1H, s); MS (M+H)$^+$219, (M+NH$_4$)$^+$236. Analysis calc'd for $C_{12}H_{14}N_2O_2$: C, 66.03; H, 6.46; N, 12.84. Found: C, 66.0, H, 6.36; N, 12.83.

Example 16

Preparation of N-Hydroxy-N-[4-(2-benzo[b]thienyl)-3-butyn2-yl]urea

The title compound was prepared according to the procedure of Example 15 using 2-ethynylbenzo[b]thiophene instead of phenylacetylene in step (a), and using trimethylsilyl isocyanate instead of methyl isocyanate in step (d). m.p. 168°–169° C.; NMR (300 MHz, DMSO-$d_6$), 1.4 (3H, d, J=7 Hz), 5.20 (1H, q, J=7Hz), 6.61 (2H, s), 7.42 (2H, m), 7.61 (1H, s), 7.85 (1H, m), 7.95 (1H, m), 9.42 (1H, s); MS (M+1)$^+$261. Analysis calc'd for $C_{13}H_{12}N_2O_2S_1$: C, 59.97; H, 4.64; N, 10.76. Found: C, 59.49, H, 4.56; N, 10.57.

Example 17

Preparation of N-Hydroxy-N-[4(4-bromophenyl)-3-butyn-2-yl]urea

The title compound was prepared according to the procedure of Example 15 using p-bromophenylacetylene instead of phenylacetylene and LDA instead of n-BuLi in step (a), and using trimethylsilyl isocyanate instead of methyl isocyanate in step (d). m.p. 155°–157° C.; NMR (300 MHz, DMSO-$d_6$), 1.35 (3H, d, J=7 Hz), 5.12 (1H, q, J=7 Hz), 6.57 (2H, s), 7.34 (2H, d, J=9 Hz), 7.57 (2H, d, J=9 Hz), 9.35 (1H, s); MS (M+1)$^+$ 283, (M+NH$_4$)$^+$300. Analysis calc'd for $C_{11}H_{11}Br_1N_2O_2$: C, 46.66; H, 3.92; N, 9.89. Found: C, 46.5, H, 3.93; N, 9.79.

Example 18

Preparation of N-Hydroxy-N-[4(4-bromophenyl)-3-butyn-2yl]-N'-methylurea

The title compound was prepared according to the procedure of Example 15 using p-bromophenylacetylene instead of phenylacetylene and LDA instead of n-BuLi in step (a). m.p. 145°–146° C; NMR.(300 MHz, DMSO-$d_6$), 1.35 (3H, d, J=7 Hz), 2.62 (3H, d, J=5 Hz), 5.10 (1H, q, J=7 Hz), 7.11 (1H, q, J=5 Hz), 7.33 (2H, d, J=9 Hz), 7.57 (2H, d, J=9 Hz), 9.30 (1H, s); MS (M+1)$^+$297; Analysis calc'd for $C_{12}H_{13}Br_1N_2O_2$: C, 48.50; H, 4.40; N, 9.43. Found: C, 47.99, H, 4.29; N, 9.27.

Example 19

Preparation of N-Hydroxy-N-[4-(4-chlorophenyl)-3butyn-2-yl]urea

The title compound was prepared according to the procedure of Example 17 using p-chlorophenylacetylene instead of p-bromophenylacetylene. m.p. 159°–161° C.; NMR (300 MHz, DMSO-$d_6$), 1.35 (3H, d, J=7 Hz), 5.22 (1H, q, J=7 Hz), 6.56 (2H, s), 7.42 (4H, m), 9.34 (1H, s); MS (M+1)$^+$239, (M+NH$_4$)$^+$256; Analysis calc'd for $C_{11}H_{11}Cl_1N_2O_2$: C, 55.25; H, 4.64; N, 11.74. Found: C, 55.09, H, 4.39; N, 11.42.

Example 20

Preparation of N-Hydroxy-N-[4-(4-chlorophenyl)-3-butyn-2-yl]-N'-methylurea

The title compound was prepared according to the procedure of Example 18 using p-chlorophenylacetylene instead of p-bromophenylacetylene. m.p. 151°–153° C.; NMR (300 MHz, DMSO-$d_6$), 1.33 (3H, d, J=7 Hz), 2.62 (3H, d, J=5 Hz), 5.11 (1H, q, J=7 Hz), 7.12 (1H, q, J=5 Hz), 7.42 (4H, m), 9.30 (1H, s); MS (M+H)$^+$253, (M+NH$_4$)$^+$270. Analysis calc'd for $C_{12}H_{13}Cl_1N_2O_2$: C, 57.03; H, 5.81; N, 11.08. Found: C, 56.91, H, 5.08; N, 11.01.

Example 21

Preparation of N-Hydroxy-N-[4-(4-fluorophenyl)-3-butyn-2-yl]urea

The title compound was prepared according to the procedure of Example 17 using p-fluorophenylacetylene instead of p-bromophenylacetylene in step (a). m.p. 156°–158° C.; NMR (300 MHz, DMSO-$d_6$), 1.35 (3H, d, J=7 Hz), 5.13 (1H, q, J=7 Hz), 6.55 (2H, s), 7.2 (2H, t, J=7 Hz), 7.45 (2H,m), 9.34 (1H, s); MS (M+1)$^+$223, (M+NH$_4^+$ 240. Analysis calc'd for $C_{11}H_{11}F_1N_2O_2 \cdot \frac{1}{2}H_2O$: C, 57.13; H, 4.80; N, 12.11. Found: C, 57.36, H, 4.89; N, 12.0.

Example 22

Preparation of N-Hydroxy-N-[4-[4-(1-methylethyl)phenyl]-3-butyn-2-yl]urea

The title compound was prepared according to the procedure of Example 15 using p-isopropylphenylacetylene instead of p-bromophenylacetylene in step (a), and using trimethylsilyl isocyanate instead of methyl isocyanate in step (d). m.p. 154°–156° C.; NMR (300 MHz, DMSO-$d_6$), 1.18 (6H, d, J=7 Hz), 1.35 (3H, d, J=7 Hz), 2.89 (1H, m), 5.12 (1H, q, J=7 Hz), 6.55 (2H, s), 7.22 (2H, d, J=7 Hz), 7.31 (2H, d, J=7 Hz), 9.31 (1H, s); MS (M+1)$^+$247, (M+NH$_4$)$^+$ 264. Analysis calc'd for $C_{14}H_{18}N_2O_2$: C, 68.26; H, 7.36; N, 11.37. Found: C, 67.80, H, 7.27; N, 11.17.

Example 23

Preparation of N-Hydroxy-N-[4-[4-(1-methylethyl)phenyl]-3-butyn-2-yl]-N'-methylurea The title compound was prepared according to the procedure of Example 22 using methyl isocyanate instead of trimethylsilyl isocyanate in step (d). m.p. 146°–147° C.; NMR (300 MHz, DMSO-$d_6$), 1.18 (6H, d, J=7 Hz), 1.35 (3H, d, J=7 Hz), 2.61 (3H, d, J=5 Hz), 2.89 (1H, m), 5.09 (1H, q, J=7 Hz), 7.09 (1H, q, J=5 Hz), 7.22 (2H, d, J=9 Hz), 7.30 (2H, d, J=9 Hz), 9.25 (1H, s); MS (M+1)$^+$261, (M+NH$_4$)$^+$278.

Example 24

Preparation of N-Hydroxy-N-[4-(4-ethylphenyl)-3-butyn-2-yl]urea

The title compound was prepared according to the procedure of Example 22 using p-ethylphenylacetylene instead of p-isopropylphenylacetylene in step (a). m.p. 142°–144° C; NMR (300 MHz, DMSO-$d_6$), 1.15 (3H, t, J=7 Hz), 1.35 (3H, d, J=7 Hz), 2.6 (1H, q, J=7 Hz), 5.1 (1H, q, J=7 Hz), 6.55 (2H, s), 7.20 (2H, d, J=9 Hz), 7.30 (2H, d, J=9 Hz), 9.31 (1H, s); MS (M+1)$^+$233, (M+NH$_4$)$^+$250. Analysis calc'd for: C, 67.21; H, 6.94; N, 12.06. Found: C, 66.92, H, 6,93; N, 12.04.

Example 25

Preparation of N-Hydroxy-N-[4-(4-ethylphenyl)-3-butyn-2-yl]-N'-methylurea

The title compound was prepared according to the procedure of Example 23 using p-ethylphenylacetylene instead of p-isopropylphenylacetylene in step (a). m.p. 126°–128° C; NMR (300 MHz, DMSO-$d_6$), 1.15 (3H, t, J=7 Hz), 1.35 (3H, d, J=7 Hz), 2.61 (5H, m), 5.08 (1H, q, J=7 Hz), 7.1 (1H, q, J=5 Hz), 7.18 (2H, d, J=9 Hz), 7.29 (2H, d, J=9 Hz), 9.25 (1H, s); MS (M+1)$^+$247, (M+NH$_4$)$^+$264. Analysis calc'd for $C_{14}H_{18}N_2O_2$: C, 68.26; H, 7.36; N, 11.37. Found: C, 67.85, H, 7.33; N, 11.31.

Example 26

Preparation of N-Hydroxy-N-(6-phenyl-3-hexyn-2-yl)urea

The title compound was prepared according to the procedure of Example 24 using 4-phenyl-1-butyne instead of p-ethylphenylacetylene in step (a). m.p. 113°–114° C.; NMR (300 MHz, DMSO-$d_6$), 1.21 (3H, d, J=7 Hz), 2.38 (dt, 2H, J=7 Hz, J=15 Hz), 2.71 (t, 2H, J=7 Hz), 4.85 (1H, q, J=7 Hz), 6.45 (1H, s), 7.25 (5H, m), 9.15 (1H, s); MS (M+NH$_4$)$^+$250. Analysis calc'd for $C_{13}H_{16}N_2O_2$: C, 67.21; H, 6.94; N, 12.06. Found: C, 66.84, H, 6.98; N, 11.75.

Example 27

Preparation of N-Hydroxy-N-(6-phenyl-3-hexyn-2-yl)-N'-methylurea

The title compound was prepared according to the procedure of Example 25 using 4-phenyl-1-butyne instead of p-ethylphenylacetylene in step (a). m.p. 121°–123° C.; NMR (300 MHz, DMSO-$d_6$), 1.22 (3H, d, J=7 Hz), 2.39 (dr, 2H, J=7 Hz, J=15 Hz), 2.6 (3H, d, J=5 Hz); 2.70 (2H, t, J=7 Hz), 4.82 (1H, q, J=7 Hz), 6.99 (1H, q, J=5 Hz), 7.25 (5H, m), 9.08 (1H, s); MS (M+NH$_4$)$^+$264. Analysis calc'd for C, 68.26; H, 7.36; N, 11.37. Found: C, 68.19, H, 7.33; N, 11.211.

Example 28

Preparation of N-Hydroxy-N-[4-(4-methylphenyl)-3-butyn-2-yl]urea

The title compound was prepared according to the procedure of Example 24 using p-methylphenylacetylene instead of p-ethylphenylacetylene in step (a). m.p. 144° C.; NMR (300 MHz, DMSO-$d_6$), 1.33 (3H, d, J=7 Hz), 2.30 (3H, s), 5.11 (1H, q, J=7 Hz), 6.54 (1H, s), 7.17 (2H, d, J=7 Hz), 7.28 (2H, d, J=7 Hz), 9.32 (1H, s); MS (M+1)$^+$ 219, (M+NH$_4$)$^+$236. Analysis calc'd for $C_{12}H_{14}N_2O_2$: C, 66.03; H, 6.47; N, 12.84. Found: C, 65.52, H, 6.46; N, 12.61.

Example 29

Preparation of N-Hydroxy-N-[4-(4-methylphenyl)-3-butyn-2-yl]-N'-methylurea

The title compound was prepared according to the procedure of Example 25 using p-methylphenylacetylene instead of p-ethylphenylacetylene in step (a). m.p. 137°–138° C.; NMR (300 MHz, DMSO-$d_6$), 1.35 (3H, d, J=7 Hz), 2.31 (3H, s), 2.61 (3H, d, J=5 Hz), 5.09 (1H, q, J=7 Hz), 7.09 (1H, q, J=5 Hz), 7.15 (2H, d, J=7 Hz), 7.28 (2H, d, J=7 Hz), 9.25 (1H, s); MS (M+1)$^+$233, (M+NH$_4$)$^+$250. Analysis calc'd for C$_{13}$H$_{16}$N$_2$O$_2$: C, 67.21; H, 6.94; N, 12.06. Found: C, 66.81, H, 6.81; N, 11.97.

Example 30

Preparation of N-Hydroxy-N-(5-phenyl-3-pentyn-2-yl)urea

The title compound was prepared according to the procedure of Example 15 using 1-phenyl-2-propyne instead of phenylacetylene in step (a), and using trimethylsilyl isocyanate instead of methyl isocyanate in step (d). m.p 106°-7° C.; $^1$H NMR (d$_6$ Me$_2$SO) 1.28 (d, 3, J=7 Hz), 3.61 (s, 2), 4.94 (q, 1, J=7 Hz), 6.51 (s, 2), 7.22 (m, 1), 7.33 (m, 4), 9.22 (s, 1) ppm; mass spectrum m/e 236 (M$^+$+NH$_4$). Analysis calculated for C$_{12}$H$_{14}$N$_2$O$_2$: C, 66.03, H, 6.46, N, 12.83; found: C, 65.41, H, 6.33, N, 12.56.

Example 31

Preparation of N-Hydroxy-N-[4-(2-furyl)-3-butyn-2-yl]urea

The title compound was prepared according to the procedure of Example 15 using 2-ethynylfuran instead of phenylacetylene in step (a), and using trimethylsilyl isocyanate instead of methyl isocyanate in step (d). m.p 141°-2° C.; $^1$H NMR (d$_6$ Me$_2$SO) 1.35 (d, 3, J=7 Hz), 5.15 (q, 1, J=7 Hz), 6.52 (dd, 1, J=1.5, 3 Hz), 6.58 (s, 2), 6.72 (d, 1, J=4.5 Hz), 7.68 (m, 1), 9.38 (s, 1) ppm; mass spectrum m/e 195 (M$^+$+H). Analysis calculated for C$_9$H$_{10}$N$_2$O$_3$: C, 55.66, H, 5.16, N, 14.42; found: C, 55.24, H, 4.86, N, 14.08.

Example 32

Preparation of N-Hydroxy-N-(3-phenyl-2-propynyl)urea

The title compound was prepared according to the procedure of Example 15 using paraformaldehyde instead of acetaldehyde in step (a), and using trimethylsilyl isocyanate instead of methyl isocyanate in step (d). m.p 127°-8° C.; $^1$H NMR (d$_6$ Me$_2$SO) 4.33 (s, 2), 6.55 (s, 2), 7.39 (m, 5), 9.60 (s, 1) ppm; mass spectrum m/e (rel intensity) 208 (100, M$^+$+NH$_4$), 191 (60, M$^+$+H). Analysis calculated for C$_{10}$H$_{10}$N$_2$O$_2$: C, 63.14, H, 5.30, N, 14.73; found: C, 62.56, H, 5.25, N, 14.43.

Example 33

Preparation of N-Hydroxy-N-[3-(3-phenoxyphenyl)-2-propynyl]urea

The title compound was prepared according to the procedure of Example 15 using m-phenoxyphenylacetylene and paraformaldehyde instead of phenylacetylene and acetaldehyde respectively in step (a), and using trimethylsilyl isocyanate instead of methyl isocyanate in step (d). m.p 139°-41° C.; $^1$H NMR (d$_6$ Me$_2$SO) 4.30 (s, 2), 6.57 (s, 2), 6.93 (m, 1), 7.05 (m, 3), 7.19 (m, 2), 7.41 (m, 3), 9.59 (s, 1) ppm; mass spectrum m/e (rel intensity) 300 (80, M$^+$+NH$_4$), 283 (40, M$^+$+H), 257 (100), 240 (80), 222 (60). Analysis calculated for C$_{16}$H$_{14}$N$_2$O$_3$: C, 68.07, H, 4.99, N, 9.92; found: C, 67.97, H, 5.02, N, 9.83.

Example 34

Preparation of N-Hydroxy-N-[4-(3-furyl)-3-butyn-2-yl]urea

The title compound was prepared according to the procedure of Example 15 using 3-ethynylfuran instead of phenylacetylene in step (a), and using trimethylsilyl isocyanate instead of methyl isocyanate in step (d). m.p 152°-4° C.; $^1$H NMR (d$_6$ Me$_2$SO) 1.33 (d, 3, J=7 Hz), 5.09 (q, 1, J=7 Hz), 6.51 (s, 2), 6.55 (m, 1), 7.7 (m, 1), 7.95 (m, 1), 9.31 (s, 1) ppm; mass spectrum m/e (rel intensity) 212 (60, M$^+$+NH$_4$), 195 (100, M$^+$+H). Analysis calculated for C$_9$H$_{10}$N$_2$O$_3$: C, 55.66, H, 5.19, N, 14.42; found: C, 5.07, H, 5.32, N, 13.83.

Example 35

Preparation of N-Hydroxy-N-[4-[3-(4-methylphenoxy)phenyl]-3-butyn-2-yl]urea

The title compound was prepared according to the procedure of Example 15 using 3-(4-methylphenoxy)phenylacetylene instead of phenylacetylene in step (a), and using trimethylsilyl isocyanate instead of methyl isocyanate in step (d). m.p 154°-5° C.; $^1$H NMR (d$_6$ Me$_2$SO) 1.32 (d, 3, J=7 Hz), 2.31 (s, 3), 5.09 (q, 1, J=7 Hz), 6.55 (s, 2), 6.85 (m, 1), 6.97 (m, 3), 7.13 (d, 1, J=7 Hz), 7.23 (d, 2, J=7 Hz), 7.35 (t, 1, J=7 Hz), 9.33 (s, 1) ppm; mass spectrum m/e (rel intensity) 311 (70, M$^+$+H), 295 (40), 268 (80), 252 (40), 235 (100), 145 (45). Analysis calculated for C$_{18}$H$_{18}$N$_2$O$_3$: C, 69.55, H, 5.84, N, 9.02; found: C, 69.48, H, 5.94, N, 8.95.

Example 36

Preparation of N-Hydroxy-N-[3-[3-(4-methylphenoxy)phenyl]-2-propynyl]urea

The title compound was prepared according to the procedure of Example 15 using 3-(4-methylphenoxy)phenylacetylene and paraformaldehyde instead of phenylacetylene and acetaldehyde respectively in step (a), and using trimethylsilyl isocyanate instead of methyl isocyanate in step (d). m.p 133°-4° C.; $^1$H NMR (d$_6$ Me$_2$SO) 2.31 (s, 3), 4.29 (s, 2), 6.54 (s, 2), 6.87 (m, 1), 6.97 (m, 3), 7.14 (d, 1, J=7 Hz), 7.23 (d, 2, J=7 Hz), 7.35 (t, 1, J=7 Hz), 9.58 (s, 1) ppm; mass spectrum m/e (rel intensity) 297 (100, M$^+$+H), 254 (70). Analysis calculated for C$_{17}$H$_{16}$N$_2$O$_3$: C, 68.90, H, 5.44, N, 9.45; found: C, 68.88, H, 5.50, N, 9.44.

Example 37

Preparation of N-Hydroxy-N-[4-(4-methoxyphenyl)-3-butyn-2-yl]urea

The tide compound was prepared according to the procedure of Example 15 p-methoxyphenylacetylene instead of phenylacetylene in step (a), and using trimethylsilyl isocyanate instead of methyl isocyanate in step (d). m.p. 144°-6° C.; NMR (300 MHz, DMSO-d$_6$) 1.33 (d, 3 J=7 Hz), 3.77 (s, 3), 5.10 (q, 1 J=7 Hz), 6.53 (s, 2), 6.90 (d, 2, J=9 Hz), 7.32 (d, 2, J=9 Hz), 9.30 (s, 1) ppm; mass spectrum m/e (rel intensity) 252 (5, M$^+$+NH$_4$), 235 (100, M$^+$+H).

Example 38

Preparation of N-Hydroxy-N-[4-(3-phenoxyphenoxy)-2-butynyl]urea

The title compound was prepared according to the procedure of Example 15 using 3-phenoxyphenoxypropargylether and paraformaldehyde instead of phenylacetylene and acetaldehyde respectively in step (a), and using trimethylsilyl isocyanate instead of methyl isocyanate in step (d). m.p. 105°-7° C.; NMR (300 MHz, DMSO-$d_6$) 4.13 (s, 2), 4.78 (s, 2), 6.51 (s, 2), 6.57 (dd, 1, J=1.5, 9 Hz), 6.63 (t, 1, J=1.5 Hz), 6.75 (dd, 1, J=1.5, 9 Hz), 7.05 (d, 2, J=7 Hz), 7.15 (t, 1, J=7 Hz), 7.30 (t, 1, J=7 Hz), 7.40 (t, 2, J=7 Hz), 9.54 (s, 1) ppm; mass spectrum m/e (rel intensity) 330 (30, $M^++NH_4$), 313 (35, $M^++H$), 287 (40), 270 (100), 254 (40). Analysis calculated for $C_{17}H_{16}N_2O_4$: C, 65.37, H, 5.16, N, 8.97; found: C, 64.87, H, 5.19, N, 8.88.

Example 39

Preparation of N-Hydroxy-N-[3-[3-(4-methoxyphenoxy)phenyl]-2-propynyl]urea

The title compound was prepared according to the procedure of Example 15 using 3-(4-methoxyphenoxy)phenylacetylene and paraformaldehyde instead of phenylacetylene and acetaldehyde respectively in step (a), and using trimethylsilyl isocyanate instead of methyl isocyanate in step (d). m.p 144°-6° C.; $^1$H NMR ($d_6$ Me$_2$SO) 3.78 (s, 3), 4.29 (s, 2), 6.55 (s, 2), 6.83 (s, 1), 6.97 (m, 5), 7.09 (d, 1, J=7 Hz), 7.35 (t, 1, J=7 Hz), 9.58 (s, 1) ppm; mass spectrum m/e (rel intensity) 330 (50, $M^++NH_4$), 313 (80, $M^++H$), 287 (50), 270 (100). Analysis calculated for $C_{17}H_{16}N_2O_4$: C, 65.37, H, 5.16, N, 8.97; found: C, 64.84, H, 5.16, N, 8.74.

Example 40

Preparation of N-Hydroxy-N-[4-[3-(4-methoxyphenoxy)phenyl]-3-butyn-2-yl]urea The title compound was prepared according to the procedure of Example 15 using 3-(4-methoxyphenoxy)phenylacetylene instead of phenylacetylene in step (a), and using trimethylsilyl isocyanate instead of methyl isocyanate in step (d). m.p 157°-8° C.; $^1$H NMR ($d_6$ Me$_2$SO) 1.33 (d, 3, J=7 Hz), 3.75 (s, 3), 5.09 (q, 1, J=7 Hz), 6.54 (s,2), 6.79 (m, 1), 7.03 (m, 6), 7.33 (t, 1, J=7 Hz), 9.31 (s, 1) ppm; mass spectrum m/e (rel intensity) 344 (50, $M^++NH_4$), 237 (100, $M^++H$), 301 (40), 284 (95), 268 (85), 251 (50). Analysis calculated for $C_{18}H_{18}N_2O_4$: C, 66.24, H, 5.56, N, 8.59; found: C, 65.91, H, 5.74, N, 8.23.

Example 41

Preparation of N-Hydroxy-N-(4-phenoxy-2-butynyl)urea

The title compound was prepared according to the procedure of Example 15 using phenylpropargylether and panformaldehyde instead of phenylacetylene and acetaldehyde respectively in step (a), and using trimethylsilyl isocyanate instead of methyl isocyanate in step (d). m.p. 97°-9° C.; $^1$H NMR ($d_6$ Me$_2$SO) 4.13 (s, 2), 4.78 (s, 2), 6.52 (s, 2), 6.96 (m, 3), 7.31 (m, 2), 9.52 (s, 1) ppm; mass spectrum m/e (rel intensity) 238 (100, $M^++NH_4$), 222 (25), 179 (50). Analysis calculated for $C_{11}H_{12}N_2O_3$: C, 59.98, H, 5.49, N, 12.72; found: C, 59.07, H, 5.33, N, 12.58.

Example 42

Preparation of N-Hydroxy-N-[4-[3-(4-chlorophenoxy)phenyl]-3-butyn-2-yl]urea

The title compound was prepared according to the procedure of Example 15 using 3-(4-chlorophenoxy)phenylacetylene instead of phenylacetylene in step (a), and using trimethylsilyl isocyanate instead of methyl isocyanate in step (d). m.p 148°-9° C.; $^1$H NMR ($d_6$ Me$_2$SO) 1.34 (d, 3, J=7 Hz), 5.11 (q, 1, J=7 Hz), 6.55 (s, 2), 6.95 (m, 1), 7.05 (m, 3), 7.18 (d, 1, J=7 Hz), 7.38 (t, 1, J=7 Hz), 7.45 (m, 2), 9.33 (s, 1) ppm; mass spectrum m/e (rel intensity) 348 and 350 (20 and 7, $M^++NH_4$), 331 and 333 (45 and 15, $M^++H$), 305 and 307 (54 and 17), 288 and 290 (100 and 33). Analysis calculated for $C_{17}H_{15}ClN_2O_3$: C, 61.72, H, 4.57, N, 8.47; found: C, 61.23, H, 4.57, N, 8.35.

Example 43

Preparation of N-Hydroxy-N-[4-[3-(4-fluorophenoxy)phenyl]-3-butyn-2-yl]urea

The title compound was prepared according to the procedure of Example 15 using 3-(4-fluorophenoxy)phenylacetylene instead of phenylacetylene in step (a), and using dimethylsilyl isocyanate instead of methyl isocyanate in step (d). m.p 139°-40° C.; $^1$H NMR ($d_6$ Me$_2$SO) 1.33 (d, 3, J=7 Hz), 5.10 (q, 1, J=7 Hz), 6.55 (s, 2), 6.87 (m, 1), 7.03 (m, 1), 7.13 (m, 3), 7.25 (t, 2, J=8 Hz), 7.37 (t, 1, J=8 Hz), 9.33 (s, 1) ppm; mass spectrum m/e (rel intensity) 332 (80, $M^++NH_4$), 315 (75, $M^++H$), 289 (80), 272 (100). Analysis calculated for $C_{17}H_{15}FN_2O_1$: C, 64.95, H, 4.81, N, 8.91; found: C, 64.67, H, 4.76, N, 8.81.

Example 44

Preparation of N-Hydroxy-N-[3-[3-(4-fluorophenoxy)phenyl]-2-propynyl]urea

The title compound was prepared according to the procedure of Example 15 using 3-(4-fluorophenoxy)phenylacetylene and paraformaldehyde instead of phenylacetylene and acetaldehyde respectively in step (a), and using trimethylsilyl isocyanate instead of methyl isocyanate in step (d). m.p 142°-4° C.; $^1$H NMR ($d_6$ Me$_2$SO) 4.31 (s, 2), 6.55 (s, 2), 6.91 (m, 1), 7.03 (m, 1), 7.15 (m, 3), 7.27 (t, 1, J=8 Hz), 7.37 (t, 1, J=8 Hz), 9.60 (s, 1) ppm; mass spectrum m/e (rel intensity) 318 (100, $M^++NH_4$), 301 (60, $M^++H$), 275 (60), 258 (65), 242 (40). Analysis calculated for $C_{16}H_{13}FN_2O_3$: C, 63.99, H, 4.36, N, 9.33; found: C, 63.63, H, 4.38, N, 9.19.

Example 45

Preparation of N-Hydroxy-N-[5-(3-phenoxyphenoxy)-3-pentyn-2-yl]urea

The title compound was prepared according to the procedure of Example 15 using 3-phenoxyphenoxypropargyl ether instead of phenylacetylene in step (a), and using trimethylsilyl isocyanate instead of methyl isocyanate in step (d). m.p. 98°–100° C.; NMR (300 MHz, DMSO-$d_6$) 1.25 (d, 3, J=7 Hz), 4.75 (s, 2), 4.95 (q, 1, J=7 Hz), 6.52 (s, 2), 6.55 (m, 1), 6.62 (t, 1,J=3 Hz), 6.75 (m, 1), 7.03 (d, 2, J=8 Hz), 7.15 (t, 1, J=8 Hz), 7.29 (t, 1, J=8 Hz), 7.40 (t, 1, J=8 Hz) ppm; mass spectrum m/e (rel intensity) 344 (70, M$^+$+NH$_4$), 301 (30), 284 (30), 268 (100). Analysis calculated for C$_{18}$H$_{18}$N$_2$O$_4$: C, 65.24, H, 5.54, N, 8.58; found: C, 65.54, H, 5.34, N, 8.11.

Example 46

Preparation of
N-Hydroxy-N-[4-[3-(4-pyridinyloxy)phenyl]-3-butyn-2-yl]urea

The title compound was prepared according to the procedure of Example 15 using 3-(4-pyridyloxy)phenylacetylene instead of phenylacetylene in step (a), and using trimethylsilyl isocyanate instead of methyl isocyanate in step (d). m.p 123°-5° C.; $^1$H NMR (d$_6$ Me$_2$SO) 1.35 (d, 3, J=7 Hz), 5.11 (q, 1, J=7 Hz), 6.55 (s, 2), 6.93 (dd, 2, J=1, 7 Hz), 7.15 (d, 1, J=0.5 Hz), 7.20 (dd, 1, J=2.5, 8 Hz), 7.30 (d, 1, J=8 Hz), 7.47 t, 1, J=8 Hz), 8.48 (dd, 2, J=1, 7 Hz), 9.33 (s, 1 ) ppm; mass spectrum m/e (rel intensity) 298 (15, M$^+$+H), 255 (1130). Analysis calculated for C$_{16}$H$_{15}$N$_3$O$_3$·0.5 H$_2$O: C, 62.53, H, 5.25, N, 13.68; found: C, 62.83, H, 5.32, N, 12.90.

Example 47

Preparation of
N-Hydroxy-N-[4-[3-(2-pyridinyloxy)phenyl]-3-butyn-2-yl]urea

The title compound was prepared according to the procedure of Example 15 using 3-(2-pyridyloxy)phenylacetylene instead of phenylacetylene in step (a), and using s trimethylsilyl isocyanate instead of methyl isocyanate in step (d) . m.p 132°-4° C.; $^1$H NMR (d$_6$ Me$_2$SO) 1.35 (d, 3, J=7 Hz), 5.13 (q, 1, J=7 Hz), 6.55 (s, 2), 7.05 (d, 1, J=7 Hz), 7.18 (m, 4), 7.40 (t, 1, J=8 Hz), 7,87 (dr, 1, J=1.5, 7 Hz), 8.17 (dd, 1, J=1.5, 6 Hz), 9.33 (s, 1) ppm; mass spectrum m/e (rel intensity) 315 (25, M++H4), 298 (100, M$^+$+H). Analysis calculated for C$_{16}$H$_{15}$N$_3$O$_3$: C, 64.63, H, 5.08, N, 14.13; found: C, 64.49, H, 5.24, N, 13.72.

Example 48

Preparation of
N-Hydroxy-N-[5-[3-(3-pyridinyloxy)phenoxy]-3-pentyn-2-yl]urea

The title compound was prepared according to the procedure of Example 15 using 3-(3-pyridyloxy)phenoxypropargyl ether instead of phenylacetylene in step (a), and using Is trimethylsilyl isocyanate instead of methyl isocyanate in step (d). m.p. 131°-2° C.; NMR (300 MHz, DMSO-d$_6$) 1.35 (d, 3, J=7 Hz), 4.77 (d, 2, J=1.5 Hz), 4.95 (q, 1, J=7 Hz), 6.52 (s, 2), 6.63 (m, 1), 6.72 (t, 1, J=1.5 Hz), 6.81 (m, 1), 7.33 (t, 1, J=8 Hz), 7.45 (m, 1 ), 8.38 (m, 2), 9.28 (s, 1 ) ppm; mass spectrum m/e (rel intensity) 328 (20, M$^+$+H), 285 (100). Analysis calculated for C$_{17}$H$_{17}$N$_3$O$_4$: C, 62.37, H, 5.23, N, 12.83; found: C, 61.82, H, 5.19, N, 12.67.

Example 49

Preparation of
N-Hydroxy-N-[4-[3-(3-pyridinyloxy)phenoxyl-2-butynyl]urea

The title compound was prepared according to the procedure of Example 15 using 3-(3-pyridyloxy)phenoxypropargyl ether and paraformaldehyde instead of phenylacetylene and acetaldehyde respectively in step (a), and using trimethylsilyl isocyanate instead of methyl isocyanate in step (d). m.p. 126°-8° C.; NMR (300 MHz, DMSO-d$_6$) 4.13 (s, 2), 4.79 (s, 2), 6.53 (s, 2), 6.63 (dd, 1, J=1.5 8 Hz), 6.73 (t, 1, J=1.5 Hz), 6.82 (m, 1), 7.34 (t, 1, J=8 Hz), 7.45 (m, 2), 8.39 (m, 2), 9.55 (s, 1 ) ppm; mass spectrum m/e (rel intensity) 314 (12, M$^+$+H),271 (100), 188 (50). Analysis calculated for C$_{16}$H$_{15}$N$_3$O$_4$: C, 61.33, H, 4.83, N, 13.41; found: C, 60.67, H, 4.76, N, 13.20.

Example 50

Preparation off
N-Hydroxy-N-[5-[3-(2-pyridinyloxy)phenoxy]-3-pentyn-2-yl]urea

The title compound was prepared according to the procedure of Example 15 using 3-(2-pyridyloxy)phenoxypropargyl ether instead of phenylacetylene in step (a), and using trimethylsilyl isocyanate instead of methyl isocyanate in step (d). m.p. 117°-9° C.; NMR (300 MHz, DMSO-d$_6$) 1.35 (d, 3, J=7 Hz), 4.85 (d, 2, J=1.5 Hz), 4.95 (q, 1, J=7 Hz), 6.52 (s, 2), 6.73 (m, 2), 6.84 (m, 1), 7.03 (d, 1, J=8 Hz), 7.14 (m, 1), 7.33 (t, 1, J=8 Hz), 7.85 (m, 1), 8.17 (m, 1), 9.29 (s, 1) ppm; mass spectrum m/e (rel intensity) 328 (100, M$^+$+H), 285 (40), 269 (30), 188 (30). Analysis calculated for C$_{17}$H$_{17}$N$_3$O$_4$: C, 62.37, H, 5.23, N, 12.83; found: C, 62.35, H, 5.33, N, 12.75.

Example 5 1

Preparation of
N-Hydroxy-N-[4-[3-2-pyridinyloxy)phenoxy]-2-butynyl]urea

The title compound was prepared according to the procedure of Example 15 using 3-(2-pyridyloxy)phenoxypropargyl ether and panformaldehyde instead of phenylacetylene and acetaldehyde respectively in step (a), and using trimethylsilyl isocyanate instead of methyl isocyanate in step (d). m.p. 124°-7° C.; NMR (300 MHz, DMSO-d$_6$) 4.14 (s, 2), 4.80 (s, 2), 6.52 (s, 2), 6.73 (m, 2), 6.84 (m, 1 ), 7.03 (d, 1, J=8 Hz) 7.15 (m, 1), 7.33 (t, 1,J=8 Hz), 7.85 (m, 1), 8.17 (m, 1), 9.53 (s, 1) ppm; mass spectrum m/e (rel intensity) 314 (30, M$^+$+H), 271 (100), 188 (25). Analysis calculated for C$_{16}$H$_{15}$N$_3$O$_4$: C, 61.33, H, 4.83, N, 13.41; found: C, 61.11, H, 4.98, N, 13.13.

Example 52

Preparation of
N-Hydroxy-N-[5-[3-(4-pyridinyloxy)phenoxy]-3-pentyn-2-yl]urea

The title compound was prepared according to the procedure of Example 15 using 3-(4-pyridyloxy)phenoxypropargyl ether instead of phenylacetylene in step (a), and using trimethylsilyl isocyanate instead of methyl isocyanate in step (d). NMR (300 MHz, DMSO-d$_6$) 1.35 (d, 3, J=7 Hz), 4.79 (d, 2, J=1.5 Hz), 4.95 (q, 1, J=7 Hz), 6.51 (s, 2), 6.77

(m, 1), 6.83 (t, 1, J=1.5 Hz), 6.95 (m, 3), 7.39 (t, 1, J=8 Hz), 8.45 (dd, 1, J=1, 8 Hz), 9.30 (s, 1 ) ppm; mass spectrum m/e (rel intensity) 328 (30, M$^+$+H), 285 (100), 188 (40). Analysis calculated for $C_{17}H_{17}N_3O_4$: C, 62.37, H, 5.23, N, 12.83; found: C, 62.18, H, 5.38, N, 12.73.

Example 53

Preparation of
N-Hydroxy-N-[4-[3-(3-pyridinyloxy)phenyl]-3-butyn-2-yl]urea

The title compound was prepared according to the procedure of Example 15 using 3-(3-pyridyloxy)phenylacetylene instead of phenylacetylene in step (a), and using s trimethylsilyl isocyanate instead of methyl isocyanate in step (d). m.p 75°-8° C.; $^1$H NMR ($d_6$ Me$_2$SO) 1.35 (d, 3, J=7 Hz), 5.12 (q, 1, J=7 Hz), 6.57 (s, 2), 7.02 (m, 1), 7.10 (m, 1), 7.21 (d, 1,J=8 Hz), 7.40 (d, 1,J=8 Hz), 7.45 (m, 2), 8.42 (m, 2), 9.33 (s, 1) ppm; mass spectrum m/e (rel intensity) 298 (100, M$^+$+H), 282 (15), 255 (35). Analysis calculated for $C_{16}H_{15}N_3O_3 \cdot 0.5H_2O$: C, 62.79, H, 5.72, N, 13.73; found: C, 63.01, H, 6.38, N, 12.90.

Example 54

Preparation of
N-Hydroxy-N-[3-[3-(3-pyridinyloxy)phenyl]-2-propyn-1-yl]urea

The tide compound was prepared according to the procedure of Example 15 using 3-(3-pyridyloxy)phenylacetylene and panformaldehyde instead of phenylacetylene and s acetaldehyde respectively in step (a), and using trimethylsilyl isocyanate instead of methyl isocyanate in step (d). m.p. 107°–110° c.; $^1$H NMR ($d_6$ Me$_2$SO) 4.30 (s, 2), 6.57 (bs, 2), 7.02 (m, 1), 7.10 (dm, 1, J=8 Hz), 7.23 (dm, 1, J=8 Hz), 7.45 (m, 3), 8.40 (m, 2), 9.60 (s, 1) ppm; mass spectrum m/e (rel intensity) 284 (M$^+$+H, 25), 241 (100), 194 (100). Analysis calculated for $C_{15}H_{13}N_3O_3 \cdot 0.5H_2O$: C, 61.63, H, 4.83, N, 14.38; found: C, 60.82, H, 4.65, N, 13.93.

Example 55

Preparation of
N-Hydroxy-N-[6-[3-(2-pyridinyloxy)phenyl]-3-hexyn-2-yl]-urea

The title compound was prepared according to the procedure of Example 15 using 4-[3-(2-pyridyloxy)phenyl]-1-butyne instead of phenylacetylene in step (a), and using s trimethylsilyl isocyanate instead of methyl isocyanate in step (d). $^1$H NMR ($d_6$ Me$_2$SO) 1.20 (d, 3, J=7 Hz), 2.42 (dr, 2, J=3, 7 Hz), 2.73 (t, 2, J=7 Hz), 4.83 (tq, 1, J=3, 7 Hz), 6.44 (bs, 2), 6.94 (dm, 1, J=8 Hz), 7.00 (dm, 1, J=9 Hz), 7.02 (m, 1), 7.11 (m, 2), 7.32 (t, 1, J=8 Hz), 7.83 (ddd, 1, J=3, 7, 8 Hz), 8.15 (dm, 1, J=4 Hz), 9.13 (s, 1) ppm; mass spectrum m/e (rel intensity) 326 (M$^+$+H, 30), 283 (100). Analysis calculated for $C_{18}H_{19}N_3O_3 \cdot 0.5H_2O$: C, 64.55, H, 6.03, N, 12.57; found: C, 64.77, H, 5.65, N, 12.37.

Example 56

Preparation of
N-Hydroxy-N-[4-[3-(2-pyridinyloxylphenyl]-3-butyn-2-yl]-N'-methylurea The title compound was prepared according to the procedure of Example 15 using -(2-pyridyloxy)phenylacetylene instead of phenylacetylene in step (a). m.p. 147°–149° C.; $^1$H NMR ($d_6$ Me$_2$SO) 1.33 (d, 3, J=7 Hz), 2.60 (d, 3, J=5 Hz), 5.08 (q, 1,J=7 Hz), 6.88 (m, 1), 7.00 (ddd, 1, J=1, 3, 9 Hz), 7.10 (m, 4), 7.24 (m, 2), 7.36 (t, 1, J=8 Hz), 9.28 (s, 1) ppm; mass spectrum m/e (rel intensity) 329 (M$^+$+H, 100). Analysis calculated for $C_{18}H_{16}FN_2O_3$: C, 66.04, H, 4.93, N, 8.56; found: C, 66.30, H, 5.44, N, 8.46.

Example 57

Preparation of
N-hydroxy-N-{4-[5-(4-fluorophenoxy)-2-furyl[-3-butyn-2-yl}urea

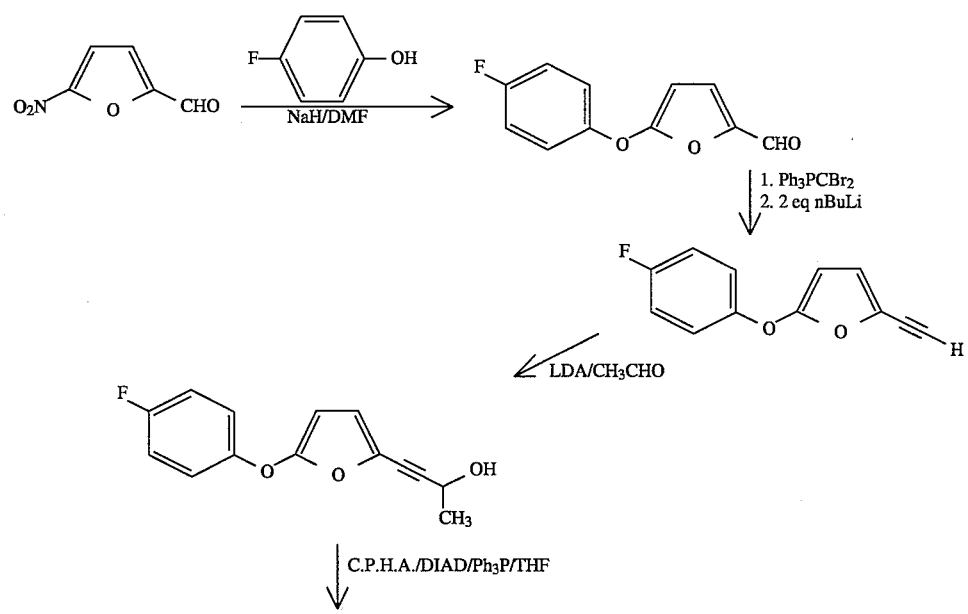

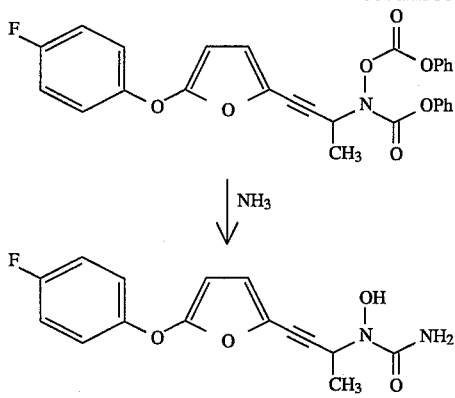

(a) 5-(4-fluorophenoxy)-2-furfuraldehyde: To a stirred suspension of penme washed 80% sodium hydride (5.3 g, 177 mmol) in THF (200 mL) under argon was added p-fluorophenol (19.9 g, 177 mmol) in small portions as a solid. After gas evolution had ended the THF was removed by rotary evaporator. The crude phenoxide was redissolved in DMF (200 mL) and cooled to 43° C.; to this stirred mixture was added 5-nitro furfuraldehyde (25 g, 177 mmol) as a DMF (50mL) solution via dropping funnel. During the addition the reaction mixture became very thick, requiring the addition of additional DMF (150 mL), removal from the ice bath and swirling. The addition was then continued to the stirred reaction mixture in the ice bath. After the addition the reaction mixture was stirred 0.5 h and poured into ice water. The mixture was extracted with ether (200 mL×8 ), the ether layers combined washed with 10% NaOH (3×100 mL), water (3×100 mL) and dried (MgSO$_4$). The mixture was concentrated and the resulting solid was dissolved in ethyl acetate, treated with decolorizing carbon, filtered and concentrated. The solid obtained was recrystalized from ether/hexane to afford 25 g (68%) of desired aldehyde as a slightly yellow solid.

(b) 2-[5-(4-fluorophenoxy)-2-furyl]-1,1dibromoethene: Carbon tetrabromide (100.73 g, 303 mmol), zinc dust (19.84 g, 303 mmol) and triphenylphosphine (79.56 g, 303 mmol) were combined in CH$_2$Cl$_2$ (700 mL ) and stirred overnight under an argon atmosphere. A CH$_2$Cl$_2$ (100 mL) solution of aldehyde (25 g, 121 mmol) was added to the s resulting suspension and stirred 2 h at room temperature. A double volume of pentane (1600 mL) was added to the stirred mixture, after additional stirring the pentane/CH$_2$Cl$_2$ was decanted. The pentane/CH$_2$Cl$_2$ solution was filtered through a short column of silica gel topped with celite. The filtrate was concentrated to afford 43 g (98%) of the dibromo olefin as a yellow oil.

(c) 2-[5-(4-fluorophenoxy)-2-furyl]-ethyne: To a stirred −78° C. THF (200 mL) solution of dibromo olefin (23.1 g, 63.81 mmol) under argon was added n-butyl lithium (51.0 mL, 127.62 mmol, 2.5M in hexanes). The reaction was stirred for 0.5 h at −78° C. Aqueous ammonium chloride was added to the cold reaction; the ice bath removed and the reaction allowed to come to room temperature. The majority of THF was removed by rotary evaporator. The resulting mixture was partitioned between water and ether. The combined ether layers were dried (MgSO$_4$) and concentrated. The residue was purified by flash column (SiO$_2$) eluting with 100% hexanes to give 6.5 g (50%) of pure acetylene.

(d) 4-[5-(4-fluorophenoxy)-2-furyl]-3-butyne-2-ol: LDA was generated by the addition of n-butyl lithium (14.2 mL, 35.4 mmol, 2.5M in hexanes) to a stirred −78° C. THF (100 mL) solution of diisopropylamine (3.58 g, 35.4 mmol). The solution was warmed to −5° C. (ice/methanol) and stirred for 0.5 h. To this stirred solution was added the acetylene (6.5 g, 32.2 mmol) obtained above as a THF solution via syringe. The reaction was stirred 0.5 h and acetaldehyde (3.11 g, 70.8 mmol) was added via syringe, the ice bath removed and the reaction warmed to room temperature. Water was added and most of the TIF removed by rotary evaporator. The resulting mixture was partitioned between water and ethyl acetate. The combined ethyl acetate layers were dried (MgSO$_4$) and concentrated. The residue was purified by flash column (SiO$_2$) elufing with 30% ether hexanes to give 6.39 g (81%) of the desired alcohol as a slightly yellow solid. 0.45 g (10%) of starting acetylene was also recovered. m.p.(ether/hexanes): 56°–57.5° C. $^1$H NMR (300 MHz, CDCl$_3$) δ TMS: 1.54 (d, J=7 Hz, 3H),1.88 (d,J=6 Hz, 1H), 4.75 (m, 1H), 5.47 (d, J=4 Hz, 1H), 6.53 (d, J=4 Hz, 1H), 7.04 (m,4H), MS (DCI-NH$_3$) m/e, 247 (M+1 ), 229.

(e) N,O-Bis(carbophenoxy)-N-{4-[5-(4-fluorophenoxy)-2-furyl]-3-butyn-2-yl}hydroxylamine: To a 0° C. stirred THF solution ( 100 mL ) of alcohol obtained above (6.39 g, 25.98 mmol, 1.0 eq), bis N,O-carbophenoxyhydroxylamine (7.80 g, 28.57 mmol, 1.1 eq) and triphenylphosphine (8.17 g, 31.17 mmol, 1.2 eq) was added a THF solution (25 ml) of diisopropylazodicarboxylate (6.30 g, 31.17 mmol, 1.2 eq) via dropping funnel. The reaction mixture was stirred 0.5 h at room temperature and concentrated. The crude is reaction mixture was dissolved in a minimum of CH$_2$Cl$_2$, loaded onto a flash column (SiO$_2$) and eluted with CH$_2$Cl$_2$. Fractions containing product were combined, concentrated. The resulting residue was purified by a second column chromatography, eluting with 50% CH$_2$Cl$_2$/hexanes to afford 7.7 g (59%) of the desired product as a thick yellow oil.

(f). In a screw top vessel with a teflon O-ring was placed the bis carbophenoxy hydroxylamine derivative (7.5 0g, 14.97 mmol) obtained above. Liquid ammonia (~10–15mL) was condensed using a cold finger (dry ice/acetone) into the cooled (also −78° C.) reaction vessel. The vessel was sealed and the ice bath removed and the reaction allowed to stirr/stand overnight at room temperature. The vessel was then recooled to −78° C. and opened, the ice bath was removed and the reaction mixture allowed to come to room temperature and the ammonia allowed to evaporate. The crude residue was dissolved in ~15% MeOH/CH$_2$Cl$_2$ and passed through a short silica column. Fractions containing product were combined,concentrated and triturated( to remove phenol) with 1:1 ether:hexane (2×) to give 2.6 g of N-hydroxyurea, as a yellow solid. Recrystalization from ethyl acetate/hexanes gave 2.3 g of the title compound as an off white solid. The mother liquor and the ether/hexane washes from the phenol trituration were combined, concentrated and chromatographed with 5% MeOH/CH$_2$Cl$_2$, and the resulting solid recrystalized to give an additional 0.3 g of the title compound. Total yield 2.6 g (57%). m.p.: 148°–150° C. (dec). $^1$H NMR (300 MHz, DMSO-d$_6$) δ TMS: 1.34 (d, J=7 Hz, 3H), 5.13 (q, J=7 Hz, 1H), 5.76 (d, J=3 Hz, 1H), 6.56 (bs, 2H), 6.74 (d, J=3 Hz, 1H), 7.13–7.30 (m,4H), 9.37 (s,1H). MS (DCI-NH$_3$) m/e, 305 (M+1), 289,229. Anal. Calcd. for C$_{15}$H$_{13}$FN$_2$O$_4$: C, 59.21; H, 4.31; N, 9.21, Found: C, 59.09; H,4.32; N, 9.15.

Example 58

Preparation of N-hydroxy-N-[4-(5-phenoxy-2-furyl)-3-butyn-2-yl]urea

The title compound was prepared according to the procedure of Example 57 using phenol instead of p-fluorophenol in step (a). m.p.: 150° C. (dec). $^1$H NMR ( 300 MHz, DMSO-d$_6$) δ TMS: 1.34 (d, J=7 Hz, 3H), 5.13 (q, J=7 Hz, 1H), 5.32 (d, J=3 Hz, 1H), 6.56 (bs, 2H), 6.75 (d, J=3 Hz, 1H), 7.10 (m, 2H), 7.21 (m,1H), 7.43 (m,2H), 9.37 (s,1H). MS (DCI-NH$_3$) m/e,309 (M+NH4)$^+$, 287 (M+1)$^+$, 269, 211.

Example 59

Preparation of N-hydroxy-N-[4-(5-thiophenoxy-2-furyl)-3-butyn-2-yl]urea (a) 5-(thiophenoxy)-2-furfuraldehyde: To a 0° C. stirred solution of thiophenol (12.1 g, 109 mmol) and 5-nitrofurfuraldehyde (14.0 g, 99.3 mmol) in acetone ( 1130 mL) was added powdered potassium carbonate (15.1 g, 109 mmol). The reaction mixture was stirred 0.5 h at 0° C. and 1 h at room temperature. An additional 5.0 g of potassium carbonate was added and the mixture stirred 1.5 h at room temperature. The reaction was then filtered washed with ether and the combined filtrates concentrated. The resulting residue was dissolved in ether (250 mL) washed with water (1×100 mL) and brine (1×100 mL), dried (MgSO$_4$) and concentrated. Purification by column chromatography (SiO$_2$, eluting with 10% ethyl acetate/hexanes) afforded 17.7 g (88%) of desired aldehyde as a slightly yellow liquid.

(b) The title compound was prepared according to the procedure of Example 57 using 5-(thiophenoxy)-2-furfuraldehyde instead of 5-(4-fluorophenoxy)-2-furfuraldehyde in step (b). m.p.: 165° C. (dec). $^1$H NMR (300 MHz, DMSO-d$_6$) δ TMS: 1.35 ( d, J= 7 Hz, 3H), 5.15(q, J=7 Hz, 1H), 6.59 (bs, 2H), 6.88 (d, J=3 Hz, 1H), (d, J=3 Hz, 1H), 7.16–7.41 (m,4H), 9.41 (s,1H). MS(DCI-NH$_3$) m/e, 320 (M+NH$_4$)$^+$, 303 (M+1)$^+$, 227.

Example 60

Preparation of N-hydroxy-N-{3-[5-(4-fluorophenoxy)-2-furyl]-2-propynl}urea

The title compound was prepared according to the procedure of Example 57 using formaldehyde instead of acetaldehyde in step (d). m.p.: 149°–151° C. (dec). $^1$H NMR (300 MHz, DMSO-d$_6$) 15 TMS: 4.34 (s, 2H), 5.26 (d, J=3 Hz, 1H), 6.58 (bs, 2H), 6.78 (d, J=3 Hz, 1H), 7.14–7.32 (m,4H), 9.62 (s,1H). MS (DCI-NH$_3$) m/e, 291 (M+1), 248.

Example 61

Preparation of N-hydroxy-N-{4-[5-(4-methoxyphenoxy)-2-furyl]-3-butyn-2-yl}urea The title compound was prepared according to the procedure of Example 57 using 4-methoxyphenol instead of p-fluorophenol in step (a). m.p.: 151°–153° C. (dec). $^1$H NMR (300 MHz, DMSO-d$_6$) δ TMS: 1.34 (d, J=7 Hz, 3H), 3.75 (s, 3H), 5.12 (q, J=7 Hz 1H), 5.61 (d, J=3 Hz, 1H), 6.57 (bs, 2H), 6.70 (d, J=3 Hz, 1H), 6.96 (m, 2H), 7.09 (m, 2H), 9.47 (s, 1H). MS (DCI-NH$_3$) m/e, 334 (M+NH$_4$)$^-$, 317 (M+1)$^+$, 274, 241.

Example 62

Preparation of N-hydroxy-N-[4-[5-(4-methylphenoxy)-2-furyl]-3-butyn-2-yl}urea The title compound was prepared according to the procedure of Example 57 using 4-methylphenol instead of p-fluorophenol in step (a). m.p.: 147°–148° C. (dec). $^1$H NMR (300 MHz, DMSO-d$_6$) δ TMS: 1.34 (d, J=7 Hz, 3H), 3.34 (s, 3H), 5.12 (q, J=7 Hz 1H), 5.72 (d, J=3 Hz, 1H), 6.57 (bs, 2H), 6.73 (d, J=3 Hz, 1H), 7.01 (m, 2H), 7.22 (m, 2H), 9.37 (s,1H). MS (DCI-NH$_3$) m/e, 301 (M+1)$^+$, 283,225.

Example 63

Preparation of N-Hydroxy-N-[3-[3-(2-pyridinyloxy)phenyl]-2-propyn-1-yl]urea

The title compound was prepared from 3-[3-(2-pyridinyloxy)phenyl]-2-propyn-1-ol] using the CPHA method (Example 57, part e). m.p. 158°–160° C.; $^1$H NMR (d$_6$ Me$_2$SO) 4.31 (s, 2), 6.55 (bs, 2), 7.08 (d, 1, J=8 Hz), 7.15 (m, 3), 7.26 (td, 1, J=1, 8 Hz), 7.40 (dr, 1,J=1, 8 Hz), 7.88 (ddd, 1, J=3, 8, 9 Hz), 8.18 (dm, 1,J=5 Hz), 9.10 (s, 1 ) ppm; mass spectrum m/e (rel intensity) 301 (M$^+$+NH4, 5), 284 (M++H, 10), 241 (60), 239 (60), 225 (100), 223 (100). Analysis calculated for C$_{15}$H$_{13}$FN$_2$O$_3$: C, 63.59, H, 4.62, N, 14.83; found: C, 63.36, H, 4.68, N, 14.61.

Example 64

Preparation of N-Hydroxy-N-[5-[3-(2-pyridinyloxy)phenyl]-4-pentyn-3-yl]urea

The title compound was prepared from 3-[ 3-(2-pyridinyloxy)phenyl]-2-propyn-1-ol] using the CPHA method (Example 57, part e). m.p. 96°–98° C.; $^1$H NMR (d$_6$ Me$_2$SO) 0.91 (t, 3, J=7 Hz), 1.70 (p, 2, J=7 Hz), 4.84 (t, 1, J=7 Hz), 6.49 (bs, 2), 7.12 (d, 1, J=8 Hz), 7.10 (m, 3), 7.19 (td, 1, J=1, 8 Hz), 7.36 (t, 1, J=8 Hz), 7.82 (ddd, 1, J=2, 6, 8 Hz), 8.12 (dm, 1, J=4 Hz), 9.23 (s, 1 ) ppm; mass spectrum m/e (rel intensity) 329 (M$^+$+NH$_4$, 5), 312 (M$^+$+H, 100), 269 (80), 253 (70). Analysis calculated for C$_{17}$H$_{17}$N$_3$O$_3$: C, 65.57, H, 5.50, N, 13.49; found: C, 65.58, H, 5.49, N, 13.52.

Example 65

Preparation of N-Hydroxy-N-[4-[3-(6-methoxypyridin-2-yloxy)phenyl]-3-butyn-2-yl]urea The title compound was prepared from 3-[3-(6-methoxypyridin-2-yloxy)phenyl]-2-propyn-1-ol using the CPHA method (Example 57, part e). m.p. 90°–91° C.; $^1$H NMR (d$_6$ Me$_2$SO) 1.35 (d, 3, J=7 Hz), 3.68 (s, 3), 5.12 (q, 1, J=7 Hz), 6.54 (m, 3), 7.16 (bd, 1, J=10 Hz), 7.23 (bd, 1, J=8 Hz), 7.41 (t, 1, J=9 Hz), 7.76 (t, 1, J=9 Hz), 9.32 (s, 1) ppm; mass spectrum m/e (rel intensity) 345 (M$^+$+NH$_4$, 5), 328 (M$^+$+H, 90), 312 (15), 285 (100), 269 (75) 267 (40). Analysis calculated for C$_{17}$H$_{17}$N$_3$O$_4$: C, 62.37, H, 5.23, N, 12.83; found: C, 62.05, H, 5.10, N, 12.68.

Example 66

Preparation of N-Hydroxy-N-[4-[-3-(2-thiazolyloxy)phenyl]-3-butyn-2-yl]urea The title compound was prepared from 3-[3-(2-thiazolyloxy)phenyl]-2-propyn-1-ol using the CPHA method (Example 57, part e). m.p. 118°–119° C.; $^1$H NMR (d$_6$ Me$_2$SO) 1.37 (d, 3, J=7 Hz), 5.13 (q, 1, J=7 Hz), 6.56 (bs, 2), 7.27 (d, 1, J=4 Hz), 7.31 (d, 1, J=4 Hz) 7.34 (m, 3), 7.46 (m, 1), 9.35 (s, 1) ppm; mass spectrum m/e (rel intensity) 304 (M$^+$+H, 100). Analysis calculated for C$_{14}$H$_{13}$N$_3$O$_3$S: C, 55.43, H, 4.32, N, 13.85; found: C, 55.28, H, 4.38, N, 13.67.

Example 67

Preparation of N-Hydroxy-N-[4-[3-(6-methylpyridin-2-yloxy)phenyl]-3-butyn-2-yl]urea The title compound was prepared from 3-[3-(6-methylpyridin-2-yloxy)phenyl]-2-propyn-1-ol using the CPHA method (Example 57, part e). m.p. 133°–135° C.; $^1$H NMR (d$_6$ Me$_2$SO) 1.36 (d, 3, J=7 Hz), 2.32 (s, 3), 5.11 (q, 1, J=7 Hz), 6.54 (bs, 2), 6.80 (d, 1, J=8 Hz), 7.01 (d, 1, J=8 Hz), 7.06 (m, 1), 7.10 (m, 1), 7.20 (bd, 1, J=8 Hz), 7.39 (t, 1, J=8 Hz), 7.74 (t, 1, J=8 Hz), 9.32 (s, 1) ppm; mass spectrum m/e (rel intensity) 312 (M$^+$+H, 100). Analysis calculated for C$_{17}$H$_{17}$N$_3$O$_3$: C, 65.58, H, 5.51, N, 13.49; found: C, 65.02, H, 5.52, N, 13.21.

Example 68

Preparation of N-Hydroxy-N-[4-[3-(6-chloropyridin--2-yloxy)phenyl]-3-butyn-2-yl urea The title compound was prepared from 3-[3-(6-chloropyridin-2-yloxy)phenyl]-2-propyn-1-ol using the CPHA method (Example 57, part e). m.p. 121°–122° C.; $^1$H NMR (d$_6$ Me$_2$SO) 1.36 (d, 3, J=7 Hz), 5.13 (q, 1, J=7 Hz), 6.55 (bs, 2), 7.03 (d, 1, J=8 Hz), 7.18 (m, 2), 7.28 (m, 2), 7.43 (bt, 1, J=8 Hz), 7.91 (t, 1, J=8 Hz), 9.33 (s, 1) ppm; mass spectrum m/e (rel intensity) 332 (M$^+$+H, 50), 256 (100). Analysis calculated for C$_{16}$H$_{14}$ClN$_3$O$_3$: C, 57.92, H, 4.25, N, 12.66; found: C, 57.82, H, 4.25, N, 12.58.

Example 69

Preparation of N-Hydroxy-N-[4-[3-(4-fluoro-3-methylphenoxy)phenyl]-3-butyn-2-yl]urea The title compound was prepared from 3-[3-(4-fluoro-3-methylphenoxy)phenyl]-2-propyn-1-ol using the CPHA method (Example 57, part e). m.p. 141°–142° C.; $^1$H NMR (d$_6$ Me$_2$SO) 1.33 (d, 3, J=7 Hz), 2.23 (d, 3, J=2 Hz), 5.10 (q, 1, J=7 Hz), 6.53 (bs, 2), 6.90 (m, 2), 7.00 (m, 2), 7.13 (dm, 1, J=8 Hz), 7.18 (t, 1, J=8 Hz), 7.36 (t, 1, J=8 Hz) 9.32 (s, 1) ppm; mass spectrum m/e (rel intensity) 346 (M$^+$+NH$_{4, 100}$), 329 (M$^+$+H, 30), 303 (80). Analysis calculated for C$_{18}$H$_{17}$FN$_2$O$_3$: C, 65.83, H, 5.22, N, 8.53; found: C, 65.53, H, 5.22, N, 8.50.

Example 70

Preparation of N-Hydroxy-N-[4-[3-(3-fluoro-4-methylphenoxy)phenyl]-3-butyn-2-yl]urea The title compound was prepared from 3-[3-fluoro-4-methylphenoxy)phenyl]-2-propyn-1-ol using the CPHA method (Example 57, part e). m.p. 128°–130° C.; $^1$H NMR (d$_6$ Me$_2$SO) 1.33 (d, 3, J=7 Hz), 2.21 (d, 3, J=2 Hz), 5.10 (q, 1, J=7 Hz), 6.53 (bd, 2), 6.28 (dd, 1, J=3, 8 Hz), 6.90 (m, 2), 7.03 (dm, 1, J=8 Hz), 7.16 (td, 1, J=1, 8 Hz), 7.30 (bt, 1, J=8 Hz), 7.37 (t, 1, J=8 Hz), 9.31 (s, 1) ppm; mass spectrum m/e (rel intensity) 346 (M$^+$+NH$_{4, 65}$), 329 (M$^+$+H, 65), 303 (65), 286 (100). Analysis calculated for C$_{18}$H$_{17}$FN$_2$O$_3$: C, 65.83, H, 5.22, N, 8.53; found: C, 66.01, H, 5.24, N, 8.50.

Example 71

Preparation of N-Hydroxy-N-[4-[3-(4-methylthiophenoxy)phenyl]-3-butyn-2-yl]urea The title compound was prepared from 3-[3-(4-methylthiophenoxy)phenyl]-2-propyn-1-ol using the CPHA method (Example 57, part e). m.p. 150°–151° C.; $^1$H NMR (d$_6$ Me$_2$SO) 1.32 (d, 3, J=7 Hz), 2.46 (s, 3), 5.08 (q, 1, J=7 Hz), 6.53 (bs, 2), 6.87 (bs, 1), 7.00 (m, 3), 7.12 (bd, 1, J=8 Hz), 7.30 (m, 3), 9.30 (s, 1) ppm; mass spectrum m/e (rel intensity) 343 (M$^+$+H, 25), 300 (25), 284 (70), 267 (100). Analysis calculated for C$_{18}$H$_{18}$N$_2$O$_3$S: C, 63.13, H, 5.30, N, 8.18; found: C, 62.87, H, 5.28, N, 8.10.

Example 72

Preparation of N-hydroxy-N-{4-[5-(4-trifluoromethylphenoxy)-2-furyl]-3-butyn-2-yl}urea The title compound was prepared according to the procedure of Example 57 using 4-trifluoromethylphenol instead of p-fluorophenol in step (a). m.p.: 149°–15 1° C. (dec). $^1$H NMR (300 MHz, DMSO-d$_6$) δ TMS: 1.35 (d, J=7 Hz, 3H), 5.14 (q, J=7 Hz, 1H), 6.03 (d, J=3 Hz, 1H), 6.58 (bs, 2H), 6.82 (d, J=3 Hz, 1H), 7.28 (d, J=9 Hz, 2H), 7.81 (d, J=9 Hz, 2H), 9.39 (s, 1H). MS (DCI-NH$_3$) m/e, 372 (M$^+$NH$_4$)$^+$, 355 (M+1)$^+$, 279.

Example 73

Preparation of N-hydroxy-N-{4-[5-(2,4-difluorophenoxy)-2-furyl]-3-butyn-2-yl}urea The title compound was prepared according to the procedure of Example 57 using 2,4-difluorophenol instead of p-fluorophenol in step (a). m.p.: 126°–128° C. $^1$H NMR (300 MHz, DMSO-$d_6$) δ TMS: 1.34 (d, J=7.5 Hz, 3H), 5.13 (q, J=7.5 Hz, 1H), 5.87 (d, J=4 Hz, 1H), 6.58 (bs, 2H), 6.76 (d, J=4 Hz, 1H), 6.99 (m, 1H), 7.40 (m, 1H), 7.50 (m, 1H), 9.38 (s, 1H). MS (DCI-NH$_3$) m/e, 340 (M+NH$_4$)$^+$, 323 (M+1)$^+$, 280, 247.

Example 74

Preparation of N-hydroxy-N-{4-[5-(3-methyl-4-fluorophenoxy)-2-furyl]-3-butyn-2yl}urea The title compound was prepared according to the procedure of Example 57 using 3-methyl,4-fluorophenol instead of p-fluorophenol in step (a). m.p.: 131°–132° C. $^1$H NMR (300 MHz, DMSO-$d_6$) δ TMS: 1.34 (d, J=7.5 Hz, 3H), 2.23 (d, J=2 Hz, 3H), 5.12 (q, J=7.5 Hz, 1H), 5.75 (d, J=4 Hz, 1H), 6.58 (bs, 2H), 6.74 (d, J=4 Hz, 1H), 6.98 (m,1H), 7.10 (m, 1H), 7.19 (t, J=9 Hz, 1H), 9.38 (s, 1H). MS (DCI-NH$_3$) m/e, 336 (M+NH$_4$)$^+$, 319 (M+1)$^+$, 243.

Example 75

Preparation of N-hydroxy-N-{4-[5-(4-fluorophenoxy)-2-furyl]-3-butyn-2-methyl-2yl}urea The title compound was prepared according to the procedure of Example 57 using acetone instead of acetaldehyde in step (d). m.p.: 106°–108° C. (dec). $^1$H NMR (300 MHz, DMSO-$d_6$) δ TMS: 1.59 (s, 6H), 5.76 (d, J=4 Hz, 1H), 6.45 (bs, 2H), 6.68 (d, J=3 Hz, 1H), 7.13–7.31 (m,4H), 9.43 (s, 1H). MS (DCI-NH$_3$) m/e (M+1), 243.

Example 76

Preparation of [+]-N-Hydroxy-N-[4-[3-(4-fluorophenoxy)phenyl]-3-butyn-2-yl]urea (a) To a solution of the product of Example 43 (500 mg, 1.59 mmol), 1,3-dicyclohexylcarbodiimide (394 mg, 1.91 mmol) and N-α-FMOC-L-phenylalanine (616 mg, 1.59 mmol) in CH$_2$Cl$_2$ (5 mls) was added a crystal of 4-N,N-dimethylaminopyriidne and the reaction was stirred for 18 hrs. It was then filtered throught Celite, concentrated, and the residue containing a mixture of diastereomers was chromatographed (silica gel, 95:5 CH$_2$Cl$_2$:Et$_2$O). The remaining fractions containing a mixture of diastereomers were combined and rechromatographed (silica gel, 97.5:2.5 CH$_2$Cl$_2$:Et$_2$O), to afford a total of 199 mg of the less polar diastereomer as a white foam and 119 mg of the more polar diastereomer as a white foam.

(b) [+] Enantiomer of Example 43. To a solution of 195 mg (0.286 mmol) of the less polar diastereomer, obtained above, in methanol (2 mls) was added K$_2$CO$_3$ (39 mg, 0.286 mmol) and the reaction was stirred for 30 mins. It was then filtered throught Celite and concentrated. The residue was chromatographed (silica, gel, 97:3 Et$_2$O:methanol) followed by crystallization in ethylacetate/hexanes to afford a white solid: m.p.=138.0°–139.5° C.; [α]$_D^{22}$=+39.00°; MS (M+H)$^+$=315.

Example 77

Preparation of [−]-N-Hydroxy-N-[4-[3-(4-fluorophenoxy)phenyl]-3-butyn-2-yl]urea The title compound was prepared according to the procedure of Example 76 using the more polar diastereomer from step (a) to provide the [−] enantiomer of Example 43 a white solid: m.p.=137°–138° C.; [α]$_D^{22}$=−39.88°; MS (M+H)$^+$=315.

Example 78

Preparation of [+]-N-Hydroxy-N-{4-[5-(4-fluorophenoxyl-2-furyl]-3-butyn-2-yl}urea The title compound was prepared according to the procedure of Example 76 using the product from example 57 instead of the product of example 43 in step (a) and the less polar diastereomer obtained in step (a) gave in step (b) a white solid:[α]$_D^{25}$=+51.1° (C= 0.36, CH$_3$OH).

Example 79

Preparation of [−]-N-Hydroxy-N-{4-[5-(4-fluorophenoxy)-2-furyl]-3-butyn-2-yl}urea The title compound was prepared according to the procedure of Example 78 using more polar diastereomer from step (a) gave in step (b) a white solid:[α]$_D^{25}$=−48.5° (C= 0.24, CH$_3$OH).

Example 80

Preparation of N,O-bis(carbophenoxy)hydroxylamine (CPHA)

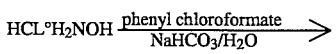

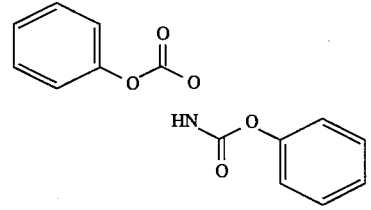

To a 0° C. (ice bath) stirred sodium bicarbonate (143 g, 1.70 Mol) solution (1L H$_2$O) in a 4 L Erlenmeyer flask was added hydroxylamine hydrochloride (58.76 g, 0.85 mol). After some foaming the reaction mixture was stirred for 0.5 h. Phenylchloroformate (400 g, 2.55 mol, 4×100 g bottles from Aldrich Chemical Company) was poured from the bottle directly into the vigorously stirred cold reaction mixture; rapidly followed by addition of additional sodium bicarbonate (214.5 g, 2.55 mol) in water( 1.8 L ); 200 mL additional water used to rinse remaining bicarbonate residue into reaction mixture. The reaction was stirred 0.5 h the ice bath removed and stirred 2 h at room temperature. The resulting suspension was filtered and the collected white solid washed with water. The resulting wet white solid was collected, suspended in hexanes (800 mL), refiltered and collected; suspension in hexane, filtration was repeated two more times. The resulting solid was dissolved in ether (800 mL), washed with brine, dried (MgSO$_4$), and concentrated to afford 200 g of the desired hydroxylamine derivative as a white solid. The material was dissolved in 450 mL ether with heating and hexanes were added (500 mL) with continued heating until some cloudiness develops. Seed crystals were added and product begins crystalization (precipitation); as solid forms more hexane was added (to a total volume of 1.8 L) and the flask allowed to stand overnight at room temperature. The mixture is then cooled to 5° and the white solid collected, washed with hexane, and dried to afford 175 g of white crystaline N,O-bis(carbophenoxy)hydroxylamine (75%). m.p.: 80°–82° C. $^1$H NMR (300 MHz, DMSO-d6) δ TMS: 7.16–7.14 (m, 10 H), 12.35 (1H), 12.35 (1H, bs). Anal. Calcd. for C$_{14}$H$_{11}$NO$_5$: C, 61.54; H, 4.06; N, 5.13. Found: C, 61.50; H, 4.14; N, 5.13.

Example 81

Preparation of N-carbo-(4-nitrophenoxy)-O-carbomethoxyhydroxylamine

HCL°H$_2$NOH $\xrightarrow{\text{1. p-nitrophenyl chloroformate}}_{\text{2. methyl chloroformate}}$

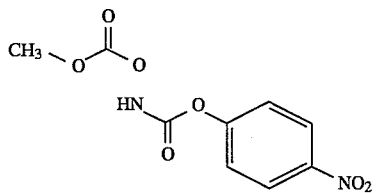

To a solution of 0.70 g (10 mmol) of hydroxylamine hydrochloride and 1.7 g (20 mmol) of sodium bicarbonate in 10 mL of water was added dropwise, with rapid stirring, over ten minutes, a solution of 2.0 g (10 mmol) of 4-nitrophenyl chloroformate in 25 mL of ether. After an additional ten minutes there was added 1 mL (13 mmol) of methyl chloroformate followed by 0.85 g (10 mmol) of solid sodium bicarbonate. After stirring for thirty minutes at room temperature, the reaction was diluted with 40 mL of brine, extracted three times with 50 mL portions of ether, and the combined organic layers were dried over magnesium sulfate, filtered, and evaporated to give 2.51 g of crude product. The crude product was recrystallized by dissolving in a boiling mixture of 100 mL of ether, 25 mL of hexane, and enough THF to effect a homogeneous solution (ca. 10 mL). This solution was boiled on a steam bath while the volume was maintained by the addition of hexane by pipette. When crystallization began, the flask was removed from the heat, allowed to cool to room temperature. The resulting crystals were filtered, washed with hexane, and air dried to give 1.7 g (66%) of the title compound: m.p.: 130°–131° C.; $^1$H as NMR (300 MHz, DMSO-d6) δ TMS: 3.92 (s, 3), 7.41 (d, 2, J=8 Hz), 8.29 (d, 2, J=8 Hz), 12.2 (bs, 1) ppm; IR (KBr) 3290, 1815, 1745, 1545, 1355, 1250, and 1215 cm$^{-1}$.

Example 82

Preparation of N,O-bis[phenoxy(thiocarbonyl)]hydroxylamine

The title compound is prepared according to the procedure of Example 76 using phenyl chlorothionoformate instead of phenyl chloroformate.

Example 83

Preparation of N,O-bis[carbo-(4-chlorophenoxy)]hydroxylamine

The title compound is prepared according to the procedure of Example 76 using 4-chlorophenyl chloroformate instead of phenyl chloroformate.

Example 84

Preparation of N,O-bis[carbo-(4-methylphenoxy)]hydroxylamine

The title compound is prepared according to the procedure of Example 76 using p-tolyl chloroformate instead of phenyl chloroformate.

Example 85

Preparation of N-carbo-[phenoxy(thiocarbonyl)]-O-carbomethoxyhydroxylamine

The title compound is prepared according to the procedure of Example 77 using phenyl chlorothionoformate instead of 4-nitrophenyl chloroformate.

Example 86

Preparation Of (N-carbophenoxy-O-Carbo-tert-butoxy)hydroxylamine (PTBHA)

Aqueous sodium hydroxide solution (1N, 80 mL) was added dropwise at room o temperature to a stirred mixture of N-carbophenoxyhydroxylamine (17.44 g, 0.0799 mol) and di-tert-butyldicarbonate (17.74 g, 0.079 mol) in 75 mL of tetrahydrofuran. The resulting mixture was stirred at room temperature for two hours, after which time the mixture was diluted with 200 mL of diethyl ether and 100 mL of brine solution. The organic layer was separated and washed with additional brine, and then dried over anhydrous magnesium sulfate and concentrated. The last traces of solvent were removed under high vacuum to yield 18.74 g (93%) of the crude product as a white solid. Recrystallization from ether/hexane gave a first crop of 13 g of large plates, m.p. 62°–64° C.

$^1$H NMR (300 MHz, DMSO-d$_6$) δ TMS: 1.48 (s, 9H), 7.11–7.18 (m, 2H), 7.24–7.31 (m, 1H), 7.39–7.47 (m, 2H), 11.83 (1H, bs).

Anal.: Calc. for C$_{12}$H$_{15}$NO$_5$: C, 56.91; H, 5.97; N, 5.53. Found: C, 56.80; H, 5.94; N, 5.52.

Example 87

Preparation of N-hydroxy-N-{4-[5-(2-fluorophenoxy)-2-furyl]-3-butyn-2-yl}urea

The title compound was prepared according to the procedure of Example 57 using 2-fluorophenol instead of p-fluorophenol in step (a). m.p.: 143°–144° C. (dec). $^1$H NMR (300 MHz, DMSO-d6) δ TMS: 1.34 (d, J=7 Hz, 3H), 5.13 (q, J=7 Hz, 1H), 5.75 (d, J=4 Hz, 1H), 6.55 (bs, 2H), 6.73 (d, J=4 Hz, 1H), 7.25 (m, 3H), 7.42 (m, 1H), 9.37 (s, 1H). MS (DCI-NH$_3$) m/e, 322 (M+NH$_4$)$^+$, 305 (M+1)$^+$, 262, 229. Anal. Calcd. for C$_{15}$H$_{13}$FN$_2$O$_4$: C, 59.21; H, 4.31; N, 9.21,. Found: C, 59.13; H, 4.38; N, 9.36.

Example 88

Preparation of
N-hydroxy-N-{4-[5-(2,6-difluorophenoxyl-2,furyl]-3-butyn-2-yl}urea The title compound was prepared according to the procedure of Example 57 using 2,6-difluorophenol instead of p-fluorophenol in step (a). m.p.: 161° C. $^1$H NMR (300 MHz, DMSO-d6) δ TMS: 1.33 (d, J=7 Hz, 3H), 5.12 (q, J=7 Hz, 1H), 5.61 (d, J=4 Hz, 1H), 6.70 (bs, 2H), 6.71 (d, J=4 Hz, 1H), 7.35 (m, 2H), 9.38 (s, 1H). MS (DCI-NH$_3$) m/e, 323 (M+1)$^+$, 247, 154. Anal. Calcd. for $C_{15}H_{12}F_2N_2O_4$: C, 55.90; H, 3.75; N, 8.69. Found: C, 56.25; H, 3.87; N, 8.50.

Example 89

Preparation of
N-hydroxy-N-{4-[5-(3-fluorophenoxy)-2-furyl]-3-butyn-2-yl}urea

The title compound was prepared according to the procedure of Example 57 using 4-methoxyphenol instead of p-fluorophenol in step (a). m.p.: 140° C. $^1$H NMR (300 MHz, DMSO-d6) δ TMS: 1.33 (d, J=7 Hz, 3H), 5.13 (q, J=7 Hz, 1H), 5.92 (d, J=4 Hz, 1H), 6.56 (bs, 2H), 6.77 (d, J=4 Hz, 1H), 6.93 (dd, J=2 Hz, 8Hz, 1H), 7.05 (m, 2H), 7.45 (m, 1H), 9.38 (s, 1H). MS (DCI-NH$_3$) m/e, 322 (M+NH$_4$)$^+$, 305 (M+1)$^-$, 229. Anal. Calcd. for $C_{15}H_{13}FN_2O_4$: C, 59.20; H, 4.30; N, 9.20. Found: C, 58.85; H, 4.22; N, 9.07.

Example 90

Preparation of
N-hydroxy-N-{4-[5-(2-methyl-4-fluorophenoxy)-2-furyl]-3-butyn-2yl}urea The title compound was prepared according to the procedure of Example 57 using 2-methyl-4-fluorophenol instead of p-fluorophenol in step (a). m.p.: 147° C. (dec). $^1$H NMR (300 MHz, DMSO-d6) δ TMS: 1.34 (d, J=7 Hz, 3H), 2.30 (s, 3H), 5.13 (q, J=7 Hz, 1H), 5.55 (d, J=4 Hz, 1H), 6.55 (bs, 2H), 6.70 (d, J=4 Hz, 1H), 7.07 (m, 2H), 7.21 (m, 1H), 9.37 (s, 1H). MS (DCI-NH$_3$) m/e, 336 (M+NH$_4$)$^+$, 319 (M+1)$^+$, 274, 243. Anal. Calcd. for $C_{16}H_{15}FN_2O_4$: C, 60.37; H, 4.75; N, 8.80. Found: C, 60.12; H, 4.88; N, 8.91.

Example 91

Preparation of
N-hydroxy-N-{4-[5-(2,4-difluorophenoxy)-2-furyl]-3-butyn-2-yl}urea The title compound was prepared according to the procedure of Example 57 using 2,4-difluorophenol instead of p-fluorophenol in step (a). m.p.: 145°–150° C. (dec). $^1$H NMR (300 MHz, DMSO-d6) δ TMS: 1.34 (d, J=7 Hz, 3H), 5.13 (q, J=7 Hz, 1H), 5.70 (d, J=4 Hz, 1H), 6.58 (bs, 2H), 6.74 (d, J=4 Hz, 1H), 7.15 (m, 1H), 7.37–7.58 (m, 2H), 9.38 (s, 1H). MS (DCI-NH$_3$) m/e, 340 (M+NH$_4$)$^+$, 323 (M+1)$^+$, 280, 247.

Example 92

Preparation of
N-hydroxy-N-{4-[5-(2,4-dichlorophenoxy)-2-furyl]-3-butyn-2-yl}urea The title compound was prepared according to the procedure of Example 57 using 2,4-dichlorophenol instead of p-fluorophenol in step (a). m.p.: 162° C. (dec). $^1$H NMR (300 MHz, DMSO-d6) δ TMS: 1.34 (d, J=7 Hz, 3H), 5.13 (q, J=7 Hz, 1H), 5.81 (d, J=4 Hz, 1H), 6.57 (bs, 2H), 6.76 (d, J=4 Hz, 1H), 7.26 (d, J=9 Hz, 1H), 7.48 (dd, J=3 Hz,9 Hz, 1H), 7.82 ( d, J=3 Hz, 1H), 9.38 (s, 1H). MS (DCI-NH$_3$) m/e, 372 (M+NHhd)$^+$, 355 (M+1)$^+$, 312, 281. Anal. Calcd. for $C_{15}H_{12}Cl_2N_2O_4$: C, 50.73; H, 3.41; N, 7.89. Found: C, 51.06; H, 3.55; N, 7.78.

Example 93

Preparation of
N-hydroxy-N-{4-[5-(4-chlorophenoxy)-2-furyl]-3-butyn-2-yl}urea

The title compound was prepared according to the procedure of Example 57 using 4-chlorophenol instead of p-fluorophenol in step (a). m.p.: 170° C. (dec). $^1$H NMR (300 MHz, DMSO-d6) δ TMS: 1.34 (d, J= 7 Hz, 3H), 5.13 (q, J=7 Hz, 1H), 5.87 (d, J=3 Hz, 1H), 6.58 (bs, 2H), 6.77 (d, J=3 Hz, 1H), 7.15 (m, 2H), 7.48 (m, 2H), 9.38 (s, 1H). MS (DCI-NH$_3$) m/e, 338 (M+NH$_4$)$^+$, 321 (M+1)$^+$, 278, 245.

Example 94

Preparation of
N-hydroxy-N-{4-[5-(4-bromophenoxy)-2-furyl]-3-butyn-2-yl}urea

The tide compound was prepared according to the procedure of Example 57 using 4-bromophenol instead of p-fluorophenol in step (a) and using lithium diisopropylamide in stead of n-butyl lithium for the conversion of the vinyl dibromide into acetylene in step (c). m.p.: 163° C. (dec). $^1$H NMR (300 MHz, DMSO-d6) δ TMS: 1.34 (d, J= 7Hz, 3H), 5.13 (q, J=7 Hz, 1H), 5.38 (d, J=4 Hz, 1H), 6.57 (bs, 2H), 6.77 (d, J=4 Hz, 1H), 7.09 (m, 2H), 7.61 (m, 2H), 9.37 (s, 1H). MS (DCI-NH$_3$) m/e, 382 (M+NH$_4$)$^+$, 365 (M+1)$^+$, 322, 291, Anal. Calcd. for $C_{15}H_{13}BrN_2O_4$: C, 49.34; H, 3.59; N, 7.67. Found: C, 48.95; H, 3.66; N, 7.58.

Example 95

Preparation of
N-hydroxy-N-{4-[5-(4-phenoxyphenoxy)-2-furyl]-3-butyn-2-yl}urea

The title compound was prepared according to the procedure of Example 57 using 4-phenoxyphenol instead of p-fluorophenol in step (a). m.p.: 130°–133° C. (dec). $^1$H NMR (300 MHz, DMSO-d6) δ TMS: 1.35 (d, J=7 Hz, 3H), 5.13 (q, J=7 Hz, 1H), 5.78 (d, J=3 Hz, 1H), 6.58 (bs, 2H), 6.75 (d, J=3 Hz, 1H), 6.98–7.19 (m, 7H), 7.39. (m, 2H), 9.38 (s, 1H). MS (DCI-NH$_3$) m/e, 396 (M+NH$_4$)$^+$, 379 (M+1)$^+$, 336, 303. Anal. Calcd. for $C_{21}H_{18}N_2O_5$: C, 66.66; H, 4.79; N, 7.40. Found: C, 66.27; H, 5.44; N, 6.92.

Example 96

Preparation of N-hydroxy-N-{4-[5-(3-phenoxyphenoxy)-2-furyl]-3-butyn-2-yl}urea The title compound was prepared according to the procedure of Example 1 using 3-phenoxyphenol instead of p-fluorophenol in step (a). m.p.: 126°–27° C. (dec). $^1$H NMR (300 MHz, DMSO-d6) δ TMS: 1.34 (d, J=7 Hz, 3H), 5.13 (q, J=7 Hz, 1H), 5.88 (d, J=3 Hz, 1H), 6.58 (bs, 2H), 6.72 (m, 1H), 6.75 (d, J=3 Hz, 1H), 6.81 (m, 2H), 7.08 (m, 2H), 7.20 (m, 1H), 7.42 (m, 3H), 9.38 (s, 1H). MS (DCI-NH$_3$) m/e, 396 (M+NH$_4$)$^+$, 379 (M+1)$^+$, 303. Anal. Calcd. for $C_{21}H_{18}N_2O_5$: C, 66.66; H, 4.79; N, 7.40. Found: C, 66.46; H, 4.74; N, 7.36.

Example 97

Preparation of N-hydroxy-N-{4-[5-(4-n-butoxyphenoxy)-2-furyl]-3-butyn-2-yl}urea The title compound was prepared according to the procedure of Example 57 using 4-n-butoxyphenol instead of p-fluorophenol in step (a). m.p.: 128°–29° C. $^1$H NMR (300 MHz, DMSO-d6) δ TMS: 0.93 (t, J=7.5 Hz, 3H), 1.34 (d, J=7 Hz, 3H), 1.43 (m, 2H), 1.86 (m, 2H), 3.94 (t, J=7 Hz, 3H), 5.12 (q, J=7 Hz, 1H), 5.61 (d, J=3 Hz, 6.56 (bs, 2H), 6.70 (d, J=3 Hz, 1H), 6.95 (m, 2H), 7.07 (m, 2H), 9.36 (s, 1H). MS (DCI-NH$_3$) m/e, 376 (M+NH$_4$)$^+$, 359 (M+1)$^+$, 316, 283.

Example 98

Preparation of N-hydroxy-N-{4-]5-(4-phenylphenoxy)-2-furyl]-3-butyn-2-yl}urea The title compound was prepared according to the procedure of Example 57 using 4-phenyphenol instead of p-fluorophenol in step (a). m.p.: 165° C. (dec). $^1$H NMR (300 MHz, DMSO-d6) δ TMS: 1.34 (d, J=7 Hz, 3H), 5.14 (q, J=7 Hz, 1H), 5.89 (d, J=4 Hz, 1H), 6.57 (bs, 2H), 6.78 (d, J=3 Hz, 1H), 7.19 (m, 2H), 7.37 (m, 2H), 7.47 (m, 2H), 7.65 (m, 2H), 7.72 (m, 2H), 9.38 (s, 1H). MS (DCI-NH$_3$) m/e, 380 (M+NH$_4$)$^+$, 363 (M+1)$^+$, 287. Anal. Calcd. for $C_{21}H_{18}N_2O_4$: C, 69.60; H, 5.01; N, 7.73. Found: C, 69.58; H, 5.08; N, 7.75.

Example 99

Preparation of N-hydroxy-N-{4-[5-(4-n-butylphenoxy)-2-furyl]-3-butyn-2-yl}urea The title compound was prepared according to the procedure of Example 57 using 4-n-butylphenol instead of p-fluorophenbl in step (a). m.p.:116°–118° C. $^1$H NMR (300 MHz, DMSO-d6) δ TMS: 0.89 (t, J=7.5 Hz, 3H), 1.29 (m, 2H), 1.34 (d, J=7 Hz, 3H), 1.53 (m, 2H), 2.56 (t, J=7.5 Hz, 3H), 5.12 (q, J=7 Hz, 1H), 5.76 (d, J=4 Hz, 1H), 6.57 (bs, 2H), 6.74 (d, J=4 Hz, 1H), 7.01 (m, 2H), 7.23 (m, 2H), 9.37 (s, 1H). MS (DCI-NH$_3$) m/e, 360 (M+NH$_4$)$^+$, 343 (M+1)$^+$, 300, 267. Anal. Calcd. for $C_{19}H_{22}N_2O_4$: C, 66.65; H, 6.48; N, 8.18. Found: C, 66.70; H, 6.49; N, 8.23.

Example 100

Preparation of N-hydroxy-N-{4-[5-(4-t-butylphenoxy)-2-furyl]-3-butyn-2-yl}urea The title compound was prepared according to the procedure of Example 57 using 4-t-butylphenol instead of p-fluorophenol in step (a). m.p.: 144°–145° C. $^1$H NMR (300 MHz, DMSO-d6) δ TMS: 1.28 ( s, 9H), 1.34 (d, J=7 Hz, 3H), 5.13 (q, J=7Hz, 1H), 5.78 (d, J=4 Hz, 1H), 6.57 (bs, 2H), 6.74 (d, J=4 Hz, 1H), 7.02 (m, 2H), 7.43 (m, 2H), 9.37 (s, 1H). MS (DCI-NH$_3$) m/e, 360 (M+NH$_4$)$^+$, 343 (M+1)$^+$, b 300, 267.

Example 101

Preparation of N-hydroxy-N-{4-[5-(4-cyanophenoxyy)-2-furyl]-3-butyn-2-yl}urea The title compound was prepared according to the procedure of Example 94 using 4-cyanophenol instead of p-bromophenol. m.p.: 164° C. (dec). $^1$H NMR (300 MHz, DMSO-d6) δ TMS: 1.34 (d, J=7.5 Hz, 3H), 5.14 (q, J=7.5 Hz, 1H), 6.06 (d, J=3Hz, 1H), 6.57 (bs, 2H), 6.82 (d, J=3 Hz, 1H), 7.26 (m, 2H), 7.92 (m, 2H), 9.38 (s, 1H). MS (DCI-NH$_3$) m/e, 329 (M+NH$_4$)$^+$, 312 (M+1)$^+$, 236. Anal. Calcd. for $C_{16}H_{13}N_3O_4$: C, 61.73; H, 4.21; N, 13.50. Found: C, 61.48; H, 4.26; N, 13.39.

Example 102

Preparation of N-hydroxy-N-{4-[5-(3,4-methylenedioxyphenoxy)-2-furyl]-3-butyn-2yl}urea The title Compound was prepared according to the procedure of Example 57 using 3,4-methylenedioxyphenol instead of p-fluorophenol in step (a). m.p.: 128°–130° C. (dec). $^1$H NMR (300 MHz, DMSO-d6) δ TMS: 1.34 (d, J=7 Hz, 3H), 5.12 (q, J=7 Hz, 1H), 5.66 (d, J=4 Hz, 1H), 6.05 (s, 2H), 6.57 (bs, 2H), 6.58 ( dd, 1H), 6.71 (d, J=4 Hz, 1H), 6.86 (d, J=3 Hz, 1H), 6.92 (d, J=9 Hz, 1H), 9.37 (s, 1H). MS (DCI-NH$_3$) m/e, 348 (M+NH$_4$)$^+$, 331 (M+1)$^+$, 288,255.

Example 103

Preparation of N-hydroxy-N-{4-[5-(2-naphthoxy)-2-furyl]-3-butyn-2-yl}urea

The title compound was prepared according to the procedure of Example 57 using 2-naphthol instead of p-fluorophenol in step (a). m.p.: 159° C. (dec). $^1$H NMR (300 MHz, DMSO-d6) δ TMS: 1.34 (d, J=7 Hz, 3H), 5.14 (q, J=7 Hz, 1H), 5.90 (d, J=4 Hz, 1H), 6.57 (bs, 2H), 6.70 (d, J=4Hz, 1H), 7.36 (dd, J=9 Hz,3 Hz, 1H), 7.46–7.58 (m, 3H), 7.94 (m, 2H), 8.02 (d, J=9 Hz, 1H), 9.37 (s, 1H). MS (DCI-NH$_3$) m/e, 337 (M+1)$^+$, 294, 261. Anal. Calcd. for $C_{19}H_{16}N_2O_4$: C, 67.85; H, 4.79; N, 8.33. Found: C, 67.87; H, 4.91; N, 8.30.

Example 104

Preparation of
N-hydroxy-N-{4-[5-(2-chloro-3-hydroxyethyl-4-fluorophenoxy)-2-furyl]-3-butyn-2-yl}urea The title compound was prepared according to the procedure of Example 57 using 2-chloro-4-fluorophenol instead of p-fluorophenol in step (a). Treatment of the dibromo olefin obtained after steb (b) in this manner, with n-butyl lithium followed by acetaldehyde gave a diol as the major product. This material was converted by the standard procedure to give the title compound. m.p.: 148° 150° C. (dec). $^1$H NMR (300 MHz, DMSO-d6) δ TMS: 1.34 (d, J=7 Hz, 3H), 1.47 (d, J=7 Hz, 3H), 5.12 (q, J=7 Hz, 1H), 5.27 (m, 1H), 5.49 (d, J=5 Hz, 1H), 5.67 (d, J=4 Hz, 1H), 6.57 (bs, 2H), 6.73 (d, J=4 Hz, 1H), 7.24 (m, 2H), 9.38 (s, 1H). MS (DCI-NH$_3$) m/e, 400 (M+NH$_4$)$^+$, 383 (M+1)$^+$, 357,307. Anal. Calcd. for C$_{17}$H$_{16}$ClFN$_2$O$_5$: C, 53.34; H, 4.21; N, 7.32. Found: C, 53.15; H, 4.20; N, 7.38.

Example 105

Preparation of
N-hydroxy-N-{4-[5-(4-{4-fluorophenylmethyl}phenoxy)-2-furyl]-3-butyn-2-yl}urea The title compound was prepared according to the procedure of Example 57 using 4-fluorophenylmethylphenol instead of p-fluorophenol in step (a). m.p.: 145°–147° C. $^1$H NMR (300 MHz, DMSO-d6) δ TMS: 1.33 (d, J=7 Hz, 3H), 3.93 (s, 2H), 5.12 (q, J=7 Hz, 1H), 5.27 (d, J=4 Hz, 1H), 6.58 (bs, 2H), 6.74 (d, J=3 Hz, 1H), 7.03 (m, 2H), 7.12 (m, 2H), 7.26 (m, 4H), 9.37 (s, 1H). MS (DCI-NH$_3$) m/e, 412 (M+NH$_4$)$^+$, 395 (M+1)$^+$, 334, 319. Anal. Calcd. for C$_{22}$H$_{19}$FN$_2$O$_4$: C, 67.00; H, 4.86; N, 7.10. Found: C, 66.81; H, 4.90; N, 7.04.

Example 106

Preparation of
N-hydroxy-N-[4-(5-phenyl-2-furyl)-3-butyn-2-yl]urea

The title compound was prepared according to the procedure of Example 57 using 5-phenylfurfural instead of 5-(4-fluorophenoxy)furfural in step (b). m.p.: 163°–164° C. $^1$H NMR (300 MHz, DMSO-d6) δ TMS: 1.39 (d, J=7 Hz, 3H), 5.29 (q, J=7 Hz, 1H), 6.60 (bs, 2H), 6.86 (d, J=4 Hz, 1H), 7.02 (d, J=4 Hz, 1H), 7.33 (m, 1H), 7.44 (m, 2H), 7.73 (m, 2H), 9.43 (s, 1H). MS (DCI-NH$_3$) m/e, 288 (M+NH$_4$)$^+$, 271 (M+1)$^+$, 228, 195. Anal. Calcd. for C$_{15}$H$_{14}$N$_2$O$_3$: C, 66.66; H, 5.22; N, 10.36. Found: C, 66.22; H, 5.27; N, 10.28.

Example 107

Preparation of
N-hydroxy-N-[4-(5-{fur-2-yl}-2-furyl)-3-butyn-2-yl]urea

The title compound was prepared according to the procedure of Example 106 using 5-(fur-2-yl)furfural instead of 5-phenylfurfural. m.p.: 154.5°–156° C. (dec). $^1$H NMR (300 MHz, DMSO-d6) δ TMS: 1.38 (d, J=7 Hz, 3H), 5.18 (q, J=7 Hz, 1H), 6.59 (bs, 2H), 6.62 (m, 1H), 6.72 (d, J=4 Hz, 1H), 6.80 (d, J=4 Hz, 1H), 6.85 (d, J=3Hz, 1H), 7.77 (m, 1H), 9.42 (s, 1H). MS (DCI-NH$_3$) m/e, 278 (M+NH$_4$)$^+$, 261 (M+1)$^+$, 185. Anal. Calcd. for C$_{13}$H$_{12}$N$_2$O$_4$: C, 60.00; H, 4.65; N, 10.76. Found: C, 59.86; H, 4.50; N, 10.59.

Example 108

Preparation of
N-hydroxy-N-[4-(5-{thien-2-yl}-2-thienyl)-3-butyn-2-yl]urea

The title compound was prepared according to the procedure of Example 106 using 5-(thien-2-yl)thiophene-2-carboxaldehyde instead of 5-phenyfurfural. m.p.: 146.5°–148° C. (dec). $^1$H NMR (300 MHz, DMSO-d6) δ TMS: 1.36 (d, J=7.5 Hz, 3H), 5.16 (q, J=7.5 Hz, 1H), 6.59 (bs, 2H), 7.10 (m, 1H), 7.21 (m, 2H), 7.36 (m, 1H), 7.56 (m, 1H), 9.39 (s, 1H). MS (DCI-NH$_3$) m/e, 310 (M+NH$_4$)$^+$, 293 (M+1)$^+$, 250, 217. Anal. Calcd. for C$_{13}$H$_{12}$N$_2$O$_2$S$_2$: C, 53.41; H, 4.14; N, 9.58. Found: C, 52.96; H, 4.13; N, 9.31.

Example 109

Preparation of
N-hydroxy-N-[4-(5-{(4-fluorophenoxy)fur-2-yl}-2-furyl)-3-butyn-2-yl] urea The title compound was prepared according to the procedure of Example 106 using 5-([4-fluorophenoxy]fur-2-yl)furfural instead of 5-phenylfurfural. m.p.: 169°–169.5° C. (dec). $^1$H NMR (300 MHz, DMSO-d6) δ TMS: 1.39 (d, J=7 Hz, 3H), 5.20 (q, J=7 Hz, 1H), 6.60 (bs, 2H), 6.90 (M, 3H), 7.09 (m, 1H), 7.30 (m, 2H), 7.84 (m, 2H), 9.43 (s, 1H). MS (DCI-NH$_3$) m/e, 372 (M+NH$_4$)$^+$, 355 (M+1)$^+$, 294, 279. Anal. Calcd. for C$_{19}$H$_{15}$FN$_2$O$_4$: C, 64.40; H, 4.27; N, 7.91. Found: C, 60.21; H, 3.90; N, 7.39.

Example 110

Preparation of
N-hydroxy-N-[4-(4-bromo-2-furyl)-3-butyn-2-yl]urea

The title compound was prepared according to the procedure of Example 57 using 4-bromofurfural instead of 5-(4-fluorophenoxy)furfural in step (b) and using lithium diisopropylamide in step (c) as described for example 94. m.p.: 100°–102° C. (dec). $^1$H NMR (300 MHz, DMSO-d6) δ TMS: 1.36 (d, J=7 Hz, 3H), 5.26 (q, J=7 Hz, 1H), 6.58 (bs, 2H), 6.96 (s, 1H), 7.93 (d, J=1 Hz, 1H), 9.41 (s, 1H). MS (DCI-NH$_3$) m/e, 290 (M+NH$_4$)$^+$, 273 (M+1)$^+$. Anal. Calcd. for C$_9$H$_9$BrN$_2$O$_3$: C, 39.58; H, 3.32; N, 10.26. Found: C, 38.08; H, 2.97; N, 9.82.

Example 111

Preparation of
N-hydroxy-N-[4-(3-thiophenoxy-2-furyl)-3-butyn-2-yl]urea

The rifle compound was prepared according to the procedure of Example 106 using 3-(thiophenoxy)furfural instead of 5-phenylfurfural. m.p.: 128°–129° C. (dec). $^1$H NMR (300 MHz, DMSO-d6) δ TMS: 1.36 (d, J=7 Hz, 3H), 5.16 (q, J=7 Hz, 1H), 6.59 (bs, 2H), 6.87 (d, J=1 Hz, 1H), 7.21 (m, 3H), 7.33 (m, 2H), 8.04 (d, J=1 Hz, 1H), 9.41 (s 1H). MS (DCI-NH$_3$) m/e, 320 (M+NH$_4$)$^+$, 303 (M+1)$^+$, 260, 229.

Example 112

Preparation of
N-hydroxy-N-[4-(2-thiophenoxy-2-furyl)-3-butyn-2-yl]urea

The title compound was prepared according to the procedure of Example 106 using 2-(thiophenoxy)furfural instead of 5-phenyfurfural. (oil). $^1$H NMR (300 MHz, DMSO-d6) δ TMS: 1.32 (d, J=7 Hz, 3H), 5.15 (q, J=7 Hz, 1H), 6.57 (bs, 2H), 6.59 (d, J=3 Hz, 1H), 7.21–7.38 (m, 5H), 7.80 (d, J=3 Hz, 1H), 9.38 (s, 1H). MS (DCI-NH$_3$) m/e, 320 (M+NH$_4$)$^+$, 303 (M+1)$^+$, 227. Anal. Calcd. for C$_{15}$H$_{14}$N$_2$O$_3$S: C, 59.59; H, 4.67; N, 9.26. Found: C, 59.3; H, 4.88; N, 9.07.

Example 113

Preparation of
N-hydroxy-N-{4-[2-(4-fluorophenoxy)-2-furyl]-3-butyn-2-yl}urea

The title compound was prepared according to the procedure of Example 106 using -(4-fluorophenoxy)furfural instead of 5-phenyfurfural. m.p.: 115°–116° C. (dec). $^1$H NMR (300 MHz, DMSO-d6) δ TMS: 1.27 (d, J=7 Hz, 3H), 5.10 (q, J=7 Hz, 1H), 6.49 (d, J=3 Hz, 1H), 6.55 (bs, 2H), 7.09–7.25 (m, 4H), 7.64 (d, J=3 Hz, 1H), 9.34 (s, 1H). MS (DCI-NH$_3$) m/e, 322 (M+NH$_4$)$^+$, 305 (M+1)$^+$, 262, 229. Anal. Calcd. for C$_{15}$H$_{13}$FN$_2$O$_4$: C, 59.21; H, 4.31; N, 9.21. Found: C, 58.38; H, 4.32; N, 9.08.

Example 114

Preparation of
N-hydroxy-N-[4-(5-{2-phenylethynyl}fur-2-yl)-3-butyn-2-yl]urea

The title compound was prepared according to the procedure of Example 106 using 2-(2-phenylethynyl)furfural instead of 5-phenyfurfural. $^1$H NMR (300 MHz, DMSO-d6) δ TMS: 1.35 (d, J=7.5 Hz, 3H), 5.17 (q, J=7.5 Hz, 1H), 6.61 (bs, 2H), 6.86 (d, J=4 Hz, H), 6.96 (d, J=4 Hz, 1H), 7.46 (m, 3H), 7.58 (m, 2H), 9.43 (s, 1H). MS (DCI-NH$_3$) m/e, 312 (M+NH$_4$)$^+$, 295 (M+1)$^+$, 219. Anal. Calcd. for C$_{17}$H$_{14}$N$_2$O$_3$: C, 69.38; H, 4.76; N, 9.52, . Found: C, 67.48; H,4.58; N, 9.27.

Example 115

Preparation of
N-hydroxy-N-{4-[5-(2-methylthiophenoxy)-2-furyl]-3-butyn-2-yl}urea The title compound was prepared according to the procedure of Example 57 using 4-(methylmercapto)phenol instead of p-fluorophenol in step (a). m.p.: 140° C. $^1$H NMR (300 MHz, DMSO-d6) δ TMS: 1.33 (d, J=7 Hz, 3H), 2.47 (s, 3H), 5.13 (q, J=7 Hz, 1H), 5.73 (d, J=4 Hz, 1H), 6.56 (bs, 2H), 6.74 (d, J=4 Hz, 1H), 7.08 (m, 2H), 7.32 (m, 2H), 9.38 (s, 1H). MS (DCI-NH$_3$) m/e, 350 (M+NH$_4$)$^+$, 333 (M+1)$^+$, 290, 257. Anal. Calcd. for C$_{16}$H$_{16}$N$_2$O$_4$S: C, 57.81; H, 4.85; N, 8.43. Found: C, 57.53; H, 4.88; N, 8.34.

Example 116

Preparation of
N-hydroxy-N-{4-[5-(3-pyridyloxy)-2-furyl]-3-butyn-2-yl}urea

The title compound was prepared according to the procedure of Example 94 using 3-hyroxypyridine instead of 4-bromophenol in step (a). m.p.: 128° C. $^1$H NMR (300 MHz, DMSO-d6) δ TMS: 1.33 (d, J=7 Hz, 3H), 5.13 (q, J=7 Hz, 1H), 5.89 (d, J=4 Hz, 1H), 6.55 (bs, 2H), 6.77 (d, J=4 Hz, 1H), 7.47 (m, 1H), 7.61 (m, 1H), 8.45 (dd, J=1.5 Hz, 6 Hz, 1H), 8.49 (d, J=3 Hz, 1H), 9.39 (s, 1H). MS (DCI-NH$_3$) m/e, 288 (M+1)$^+$, 201,185. Anal. Calcd. for C$_{14}$H$_{13}$N$_3$O$_4$: C, 58.53; H, 4.56; N, 14.62. Found: C, 58.29; H, 4.49; N, 14.57.

Example 117

Preparation of
N-hydroxy-N-{4-[5-(5-chloro-3-pyridyloxy)-2-furyl]-3-butyn-2-yl}urea The title compound was prepared according to the procedure of Example 94 using 5-chloro-3-hydroxypyridine instead of 4-bromophenol in step (a). m.p.: 150° C. $^1$H NMR (300 MHz, DMSO-d6) δ TMS: 1.33 (d, J=7 Hz, 3H), 5.14 (q, J=7 Hz, 1H), 5.96 (d, J=5 Hz, 1H), 6.54 (bs, 2H), 6.77 (d, J=5 Hz, 1H), 7.88 (t, J=2 Hz, 1H), 8.47 (d, J=2 Hz, 1H), 8.53 (d, J=2 Hz, 1H), 9.37 (s, 1H). MS (DCI-NH$_3$) m/e, 322 (M+1)$^+$, 248, 114. Anal. Calcd. for C$_{14}$H$_{12}$ClN$_3$O$_4$: C, 52.26; H, 3.76; N, 13.06. Found: C, 51.71; H, 3.69; N, 12.83.

Example 118

Preparation of
N-hydroxy-N-{4-[5-(6-methyl-3-pyridyloxy)-2-furyl]-3-butyn-2-yl}urea The title compound was prepared according to the procedure of Example 94 using 6-methy-3-hydroxypyridine instead of 4-bromophenol in step (a). m.p.: 149° C. $^1$H NMR (300 MHz, DMSO-d6) δ TMS: 1.33 (d, J=7 Hz, 3H), 2.46 (s, 3H), 5.12 (q, J=7 Hz, 1H), 5.80 (d, J=4 Hz, 1H), 6.55 (bs, 2H), 6.75 (d, J=4 Hz, 1H), 7.32 (d, J=8Hz, 1H), 7.50 (dd, J=3 Hz, 8 Hz, 1H), 8.33 (d, J=3 Hz, 1H), 9.36 (s, 1H). MS (DCI-NH$_3$) m/e, 302 (M+1)$^+$, 259, 226. Anal. Calcd. for C$_{15}$H$_{15}$N$_3$O$_4$: C, 59.79; H, 5.02; N, 13.94. Found: C, 57.56; H, 4.58; N, 13.37.

Example 119

Preparation of
N-hydroxy-N-{4-[5-(2-mercaptopyridyl)-2-furyl]-3-butyn-2-yl}urea

The title Compound was prepared according to the procedure of Example 94 using 2-mercaptopyridine instead of 4-bromophenol in step (a). m.p.: 145° C. $^1$H NMR (300 MHz, DMSO-d6) δ TMS: 1.36 (d, J=7 Hz, 3H), 5.17 (q, J=7 Hz, 1H), 6.60 (bs, 2H), 6.91 (d, J=4 Hz, 1H), 6.96 (m, 1H), 7.09 ( d, J=4 Hz, 1H), 7.22 (m, 1H), 7.73 (m, 1H), 8.42 (m, 1H), 9.41 (s, 1H). MS (DCI-NH$_3$) m/e, 321 (M+NH$_4$)$^+$, 304 (M+1)$^+$, 261. Anal. Calcd. for C$_{14}$H$_{13}$N$_3$O$_3$S: C, 55.43; H, 4.31; N, 13.85. Found: C, 55.44; H, 4.36; N, 14.55.

Example 120

Preparation of N-hydroxy-N-[4-(5-n-butoxyfur-2-yl)-3-butyn-2-yl]urea

The title compound was prepared according to the procedure of Example 106 using 5-n-butoxyfurfural instead of 5-phenyfurfural. m.p.: 132° C. (dec). $^1$H NMR (300 MHz, DMSO-d6) δ TMS: 0.91 (t, J=7.5 Hz, 3H), 1.33 (d, J=7 Hz, 3H), 1.37 (m, 2H), 1.67 (m, 2H), 4.06 (t, J=7 Hz, 2H), 5.11 (q, J=7 Hz, 1H), 5.38 (d, J=3Hz, 1H), 6.54 (bs, 2H), 6.62 (d, J=3 Hz, 1H), 9.34 (s, 1H). MS (DCI-NH$_3$) m/e, 267 (M+1)$^+$, 191, 150.

Example 121

Preparation of N-hydroxy-N-[4-(5-methoxyfur-2-yl)-3-butyn-2-yl]urea

The title compound was prepared according to the procedure of Example 106 using 5-(methoxy)furfural instead of 5-phenyfurfural. m.p.: 131° C. $^1$H NMR (300 MHz, DMSO-d6) δ TMS: 1.33 (d, J=7 Hz, 3H), 3.83 (s, 3H), 5.11 (q, J=7 Hz, 1H), 5.39 (d, J=4 Hz, 1H), 6.55 (bs, 2H), 6.63 (d, J=4 Hz, 1H), 9.34 (s, 1H). MS (DCI-NH$_3$) m/e, 242 (M+NH$_4$)$^+$, 225 (M+1)$^+$, 149. Anal. Calcd. for C$_{10}$H$_{12}$N$_2$O$_4$: C, 53.55; H, 5.39; N, 12.49. Found: C, 53.31; H, 5.45; N, 12.48.

Example 122

Preparation of N-hydroxy-N-[4-(5-methyoxythien-2-yl)-3-butyn-2-yl]urea

The title compound was prepared according to the procedure of example 106 using 5-(methoxy)thiophene-2-carboxaldehyde instead of 5-phenyfurfural. m.p.: 132°–133° C. $^1$H NMR (300 MHz, DMSO-d6) δ TMS: 1.33 (d, J=7 Hz, 3H), 3.86 (s,3H), 5.10 (q, J=7 Hz, 1H), 6.23 ( d, J=5 Hz, 1H), 6.53 (bs, 2H), 6.92 ( d, J=5 Hz, 1H), 9.32 (s, 1H). MS (DCI-NH$_3$) m/e, 258 (M+NH$_4$)$^+$, 241 (M+1)$^+$, 198, 165. Anal. Calcd. for C$_{10}$H$_{12}$N$_2$O$_3$S: C, 49.98; H, 5.04; N, 11.66. Found: C, 50.14; H, 5.08; N, 11.71.

Example 123

Preparation of N-hydroxy-N-[4-(5-thiophenoxythien-2-yl)-3-butyn-2-yl]urea

The title compound was prepared according to the procedure of Example 106 using 5-(thiophenoxy)furfural instead of 5-phenyfurfural. m.p.: 144°–145° C. (dec). $^1$H NMR (300 MHz, DMSO-d6) δ TMS: 1.34 (d, J=7 Hz, 3H), 5.14 (q, J=7 Hz, 1H), 6.58 (bs, 2H), 7.30 (m, 7H), 9.40 (s, 1H). MS (DCI-NH$_3$) m/e, 319 (M+1)$^+$, 258, 243. Anal. Calcd. for C$_{15}$H$_{14}$N$_2$O$_2$S$_2$: C, 56.57; H, 4.42; N, 8.80. Found: C, 56.51; H, 4.39; N, 8.77.

Example 124

Preparation of N-hydroxy-N-{4-[5-(4-fluorothiophenoxy)-2-thionyl]-3-butyn-2-yl}urea The title compound was prepared according to the procedure of Example 106 using 5-(4-fluorothiophenoxy)furfural instead of 5-phenyfurfural. m.p.: 149°–150° C. $^1$H NMR (300 MHz, DMSO-d6) δ TMS: 1.34 (d, J=7 Hz, 3H), 5.14 (q, J=7 Hz, 1H), 6.58 (bs, 2H), 7.28 (m, 6H), 9.37 (s, 1H). MS (DCI-NH$_3$) m/e, 354 (M+NH$_4$)$^+$, 337 (M+1)$^-$, 276, 261. Anal. Calcd. for C$_{15}$H$_{13}$FN$_2$O$_2$S$_2$: C, 53.55; H, 3.89; N, 8.33. Found: C, 3.45, H, 3.87; N, 8.23.

Example 125

Preparation of N-hydroxy-N-{4-[5-(4-fluorophenoxy)-2-thienyl]-3-butyn-2-yl]urea The title compound was prepared according to the procedure of Example 106 using 5-(4-fluorophenoxyl)thiophene-2-carboxaldehyde instead of 5-phenyfurfural. m.p.: 149°–150° C. $^1$H NMR (300 MHz, DMSO-d6) δ TMS: 1.33 (d, J=7 Hz, 3H), 5.10 (q, J=7Hz, 1H), 6.54 (bs, 2H), 6.57 (d, J=1 Hz, 1H), 7.04 (d, J=5 Hz, 1H), 7.25 (m, 4H), 9.33 (s, 1H): MS (DCI-NH$_3$) m/e, 338(M+NH$_4$)$^+$, 321 (M+1)$^+$, 245. Anal. Calcd. for C$_{15}$H$_{13}$FN$_2$O$_3$S: C, 56.23; H, 4.09; N, 8.75. Found: C, 56.22; H, 4.14; N, 8.67.

Example 126

Preparation of N-hydroxy-N-{4-[5-(4-methoxyphenoxy)-2-thienyl]-3-butyn-2-yl}urea The title compound was prepared according to the procedure of Example 106 using 5-(4-methoxyphenoxyl)thiophene-2-carboxaldehyde instead of 5-phenyfurfuml. m.p.: 137°–138° C. $^1$H NMR (300 MHz, DMSO-d6) δ TMS: 1.33 (d, J=7 Hz, 3H), 3.77 (s, 3H), 5.10 (q, J=7 Hz, 1H), 6.46 (d, J=5 Hz, 1H), 6.54 (bs, 2H), 6.96 (m, 2H), 7.00 (d, J=5 Hz, 1H), 7.13 (m, 2H), 9.32 (s, 1H). MS (DCI-NH$_3$) m/e, 333 (M+1)$^+$, 290, 257. Anal. Calcd. for C$_{16}$H$_{16}$N$_2$O$_4$S: C, 57.81; H, 4.85; N, 8.43. Found: C, 57.67; H, 4.90; N, 8.15.

Example 127

Preparation of N-hydroxy-N-{4-[4-(4-fluorophenoxy)thien-2-yl]-3-butyn-2-yl}urea The title compound was prepared according to the procedure of Example 106 using 4-(4-fluorophenoxyl)thiophene-2-carboxaldehyde instead of 5-phenyfurfural. m.p.: 145° C. (dec). $^1$H NMR (300 MHz, DMSO-d6) δ TMS: 1.33 (d, J=7 Hz, 3H), 5.13 (q, J=7Hz, 1H), 6.58 (bs, 2H), 7.04 (m, 3H), 7.22 (m, 3H), 9.39 (s, 1H). MS (DCI-NH$_3$) m/e, 338 (M+NH$_4$)$^+$, 321 (M+1)$^+$.

Example 128

Preparation of N-hydroxy-N-{4-[5-bromo-2-thienyl]-3-butyn-2-yl} urea

The title compound was prepared according to the procedure of Example 110 using 5-bromothiophene-2-carboxaldehyde instead of 4-bromofurfural. m.p.: 142°–145° C. (dec). $^1$H NMR (300 MHz, DMSO-d6) δ TMS: 1.35 (d, J=7 Hz, 3H), 5.14 (q, J=7 Hz, 1H), 6.58 (bs, 2H), 7.11 (d, J=4 Hz, 1H), 7.19 (d, J=4 Hz, 1H), 9.39 (s, 1H). MS (DCO-NH$_3$) m/e, 306 (M+NH$_4$)$^+$, 389 (M+1)$^+$, 273, 230.

Example 129

Preparation of N-hydroxy-N-[4-(3-{2-phenylethynyl}phenyl)-3-butyn-2-yl]urea

The title compound was prepared according to the procedure of Example 106 using 3-(2-phenylethynyl)benzaldehyde instead of 5-phenylfurfural. $^1$H NMR (300 MHz, DMSO-d6) δ TMS: 1.37 (d, J=7 Hz, 3H), 5.15 (q, J=7 Hz, 1H), 6.57 (bs, 2H), 7.44 (m, 5H), 7.57 (m, 4H), 9.35 (s, 1H). MS (DCI-NH$_3$) m/e, 322 (M+NH$_4$)$^+$, 305 (M+1)$^+$, 246. Anal. Calcd. for C$_{19}$H$_{16}$N$_2$O$_2$: C, 75.00; H, 5.26; N, 9.21. Found: C, 74.16; H, 5.38; N, 9.14.

Example 130

Preparation of N-hydroxy-N-[4-(3-{2-thienyloxy}phenyl)-3-butyn-2-yl]urea

The title compound was prepared according to the procedure of Example 106 using 3-(2-thienyloxy)benzaldehyde instead of 5-phenylfurfural. m.p.: 110°–112° C. $^1$H NMR (300 MHz, DMSO-d6) δ TMS: 1.34 (d, J=7 Hz, 3H), 5.12 (q, J=7 Hz, 1H), 6.55 (bs, 2H), 6.73 (m, 1H), 6,91 (m, 1H), 7.02 (m, 1H), 7.10–7.19 (m, 3H), 7.38 (m, 1H), 9.34 (s, 1H). MS (DCI-NH$_3$) m/e, 320 (M+NH$_4$)$^+$, 303 (M+1)$^+$, 242. Anal. Calcd. for C$_{15}$H$_{14}$N$_2$O$_3$S: C, 59.59; H, 4.67; N, 9.26. Found: C, 59.39; H, 4.67; N, 9.20.

Example 131

Preparation of N-hydroxy-N-[4-(3-{3-thienyloxy}phenyl)-3-butyn-2-yl]urea

The title compound was prepared according to the procedure of Example 106 using 3-(3-thienyloxy)benzaldehyde instead Of 5-phenylfurfural. m.p.: 93°–95° C. $^1$H NMR (300 MHz, DMSO-d6) δ TMS: 1.34 (d, J=7 Hz, 3H), 5.11 (q, J=7 Hz, 1H), 6.56 (bs, 2H), 6.94 (m, 2H), 7.05 (m, 2H), 7.13 (m, 1H), 7.36 (t, J=8 Hz, 1H), 7.60 (m, 1H), 9.33 (s, 1H). MS (DCI-NH$_3$) m/e, 320 (M+NH$_4$)$^+$, 303 (M+1)$^+$, 242. Anal. Calcd. for C$_{15}$H$_{14}$N$_2$O$_3$S: C, 59.59; H, 4.67; N, 9.26. Found: C, 59.58; H, 4.63; N, 9.15.

Example 132

Preparation of N-hydroxy-N-[4-(3-{2-(2-pyridyl)ethenyl}phenyl)-3-butyn-2-yl]urea The title compound was prepared according to the procedure of Example 106 using 3-(2-[2-pyridyl]ethenyl)benzaldehyde instead of 5-phenylfurfural. m.p.: 122°–126° C. $^1$H NMR (300 MHz, DMSO-d6) δ TMS: 1.39 (d, J=7 Hz, 3H), 5.16 (q, J=7 Hz, 1H), 6.57 (bs, 2H), 7.24–7.44 (m, 4H), 7.53–7.72 (m, 4H), 7.80 (m, 1H), 8.58 (m, 1H), 9.36 (s, 1H). MS (DCI-NH$_3$) m/e, 308 (M+1)$^+$, 249. Anal. Calcd. for C$_{18}$H$_{17}$N$_3$O$_2$: C, 70.34; H, 5.57; N, 13.67. Found: C, 69.90; H, 5.60;.N, 13.60.

Example 133

Preparation of N-hydroxy-N-[4-(3-{2-furyl}phenyl)-3-butyn-2-yl]urea

The title compound was prepared according to the procedure of Example 106 using 3-(2-furyl)benzaldehyde instead of 5-phenylfurfural. m.p.: 157.5°–159° C. (dec). $^1$H NMR (300 MHz, DMSO-d6) δ TMS: 1.38 (d, J=7 Hz, 3H), 5.15 (q, J=7 Hz, 1H), 6.57 (bs, 2H), 6.61 (m, 1H), 7.05 (m, 1H), 7.30 (m, 1H), 7.42 (m, 1H), 7.70 (m, 2H), 7.77 (m, 1H), 9.47 (s, 1H). MS (DCI-NH$_3$) m/e, 288 (M+NH$_4$)$^+$, 271 (M+1)$^+$, 212. Anal. Calcd. for C$_{15}$H$_{14}$N$_2$O$_3$: C, 66.66; H, 5.22; N, 10.36. Found: C, 63.87; H, 5.13; N, 10.07.

Example 134

Preparation of N,hydroxy-N-[4-(3-{1-benzoxazolyoxy}phenyl)-3-butyn-2-yl]urea The title compound was prepared according to the procedure of Example 106 using 3-(1-benzoxazolyl)benzaldehyde instead of 5-phenylfurfural. m.p.: 136°–143° C. (dec). $^1$H NMR (300 MHz, DMSO-d6) δ TMS: 1.37 (d, J=7 Hz, 3H), 5.16 (q, J=7 Hz, 1H), 6.57 (bs, 2H), 7.26–7.43 (m, 3H), 7.49–7.69 (m, 5H), 9.37 (s, 1H). MS (DCI-NH$_3$) m/e, 355 (M+NH$_4$)$^+$, 338 (M+1)$^+$, 295,. Anal. Calcd. for C$_{18}$H$_{15}$N$_3$O$_4$: C, 64.09; H, 4.48; N, 12.46. Found: C, 64.10; H, 4.66; N, 12.30.

Example 135

Preparation of N-hydroxy-N-[4-(3-{3-pyridyloxy}-6-methoxyphenyl)-3-butyn-2-yl]urea The title compound was prepared according to the procedure of Example 110 using 3-(3-{3-pyridyloxy}-6-methoxy)benzaldehyde instead of 4-bromofurfural. m.p.: 153°–154° C. $^1$H NMR (300 MHz, DMSO-d6) δ TMS: 1.33 (d, J=7 Hz, 3H), 3.80 (s, 3H), 5.13 (q, J=7 Hz, 1H), 6.52 (bs, 2H), 7.08 (m, 3H), 7.38 (m, 2H), 8.32 (m, 2H), 9.28 (s, 1H). MS (DCI-NH$_3$) m/e, 328 (M+1)$^+$, 285, 269. Anal. Calcd. for C$_{17}$H$_{17}$N$_3$O$_4$: C, 62.37; H, 5.23; N, 12.84. Found: C, 62.04; H,5.30; N, 12.59.

Example 136

Preparation of N-hydroxy-N-[4-(3-{4-fluorophenoxy}-6-methoxyphenyl)-3-butyn-2yl]urea The title compound was prepared according to the procedure of Example 106 using 3-(4-fluorophenoxy)-6-methoxybenzaldehyde instead of 5-phenylfurfural. m.p.: 141°–142° C. $^1$H NMR (300 MHz, DMSO-d6) δ TMS: 1.34 (d, J=7 Hz, 3H), 3.80 (s, 3H), 5.12 (q, J=7 Hz, 1H), 6.54 (bs, 2H), 6.95 (m, 1H), 7.02 (m, 4H), 7.21 (m, 2H), 9.28 (s, 1H). MS (DCI-NH$_3$) m/e, 362 (M+NH$_4$)$^+$, 345(M+1)$^+$, 303, 284. Anal. Calcd. for C$_{18}$H$_{17}$FN$_2$O$_4$: C, 62.77; H, 4.97; N, 8.13. Found: C, 61.82; H, 4.92; N, 8.11.

Example 137

Preparation of N-hydroxy-N-[4-(3-{4-fluorophenoxy}-4-methoxyphenyl)-3-butyn-2-yl]urea The title compound was prepared according to the procedure of Example 106 using 3-(4-fluorophenoxy)-4-methoxybenzaldehyde instead of 5-phenyfurfural. m.p.: 139°–140° C. $^1$H NMR (300 MHz, DMSO-d6) δ TMS: 1.32 (d, J=7 Hz, 3H), 3.78 (s, 3H), 5.08 (q, J=7 Hz, 1H), 6.52 (bs, 2H), 6.93 (m, 3H), 7.18 (m, 4H), 9.28 (s, 1H). MS (DCI-NH$_3$) m/e, 362 (M+NH$_4$)$^+$, 345(M+1)$^+$, 269. Anal. Calcd. for C$_{18}$H$_{17}$FN$_2$O$_4$: C, 62.77; H, 4.97; N, 8.13. Found: C, 62.42; H, 4.62; N, 7.96.

Example 138

Preparation of N-hydroxy-N-[4-(5-{5-bromothien-2-yl}-2-thienyl)-3-butyn-2-yl]urea The title compound was prepared according to the procedure of Example 110 using 5-(5-bromothien-2-yl)thiophene-2-carboxaldehyde instead of 4-bromofurfural. m.p.: 152°–154° C. (dec). $^1$H NMR (300 MHz, DMSO-d6) δTMS: 1.36 (d, J=7 Hz, 3H), 5.16 (q, J=7 Hz, 1H), 6.57 (bs, 2H), 7.18–7.25 (m, 4H), 9.39 (s, 1H). MS (DCI-NH$_3$) m/e, 388 (M+NH$_4$)$^+$, 371 (M+$^1$)$^+$, 295. Anal. Calcd. for C$_{13}$H$_{11}$BrN$_2$O$_2$S$_2$: C, 42.06; H, 2.99; N, 7.55. Found: C, 42.83; H, 3.08; N, 7.59.

Example 139

Preparation of N-hydroxy-N-[4-(5-{thien-2-yl}-2-furyl)-3-butyn-2-yl]urea

The title compound was prepared according to the procedure of Example 106 using 5-(thien-2-yl)furfural instead of 5-phenyfurfural. m.p.: 124°–125° C. (dec). $^1$H NMR (300 MHz, DMSO-d6) δ TMS: 1.36 (d, J=7 Hz, 3H), 5.16 (q, J=7 Hz, 1H), 6.57 (bs, 2H), 6.61 (m, 1H), 6.85 (d, J=3 Hz, 1H), 7.23 (d, J=3 Hz, 1H), 7.28 (d, J=3 Hz, 1H), 7.73 (m, 1H), 9.39 (s, 1H). MS (DCI-NH$_3$) m/e, 294 (M+NH$_4$)$^+$, 277 (M+1)$^+$, 232, 216, 201.

Example 140

Preparation of N-hydroxy-N-4-(2-(2-pyridyloxy)phenyl)-3-butyn-2-yl]urea

A solution of 2-hydroxybenzaldehyde (10.00 g, 81.9 mmol), 2-bromopyridine (26.91 g, 170.3 mmol), potassium carbonate (17.54 g, 126.9 mmol), and copper (2.60 g, 40.95 mmol) in pyridine (80 mls) was refluxed for 3 days. The reaction was then cooled to r.t., filtered through Celite, diluted with ethylacetate (500 mls) and washed with water (3×300 mls). The organic was then dried with MgSO$_4$ and concentrated. The resulting residue was chromatographed (silica gel, 9:1 hexanes:ether) to afford 16.21 g (99%) of 2-(2-pyridyloxy)benzaldehyde as a yellow oil.

To a solution of carbon tetrabromide (54.09 g, 162.9 mmol), and zinc (10.97 g, 162.9 mmol) in CH$_2$Cl$_2$ (800 mls) was added triphenylphosphine (42.68 g, 162.9 mmol) and the mixture was allowed to stir for 18 hrs. 2-(2-Pyridyloxy)benzaldehyde (16.21 g, 81.5 mmol) was then added as a solution in CH$_2$Cl$_2$ (50 mls) and the reaction was stirred for 2 hrs. It was then poured into pentane (1.6 liters) with good stirring, then allowed to stand for 1 hr. The solution was decanted and concentrated. The residue left after decantation was taken up in 1N NaOH (500 mls) and filtered through Celite. It was then washed with CH$_2$Cl$_2$ (500 mls). This organic was dried with MgSO$_4$, concentrated and combined with the material obtained from the decanted solution to afford 29.01 g of 1,1-dibromo-2-(2-(2-pyridyloxy)phenyl)ethene as an off-white solid.

To a solution of 1,1-dibromo-1-(2-(2-pyridyloxy)phenyl)ethene, from above, in THF (350 mls) at –78° C., was added n-butyllithium (65.2 mls of a 2.5M solution in hexanes, 163 mmol) dropwise. Upon completion of addition, the reaction was stirred for 1 hr at –78° C. It was then quenched with aqu. sat'd NH$_4$Cl (500 mls) and allowed to warm to r.t. The THF was then stripped off in vacuo and the resulting aqueous solution was extracted with ethylacetate (3×500 mls). The organics were combined, dried with MgSO$_4$ and concentrated to afford 2-(2-pyridyloxy)phenylacetylene which was used as is.

To a solution of 2-(2-pyridyloxy)phenylacetylene,(8.58 g, 44.3 mmol from above) in THF (200 mls) at –78° C. was added n-butyllithium (18.6 mls of a 2.5M solution in hexanes, 46.5 mmol) dropwise. Upon completion of addition, the mixture was stirred for 30 mins. Acetaldehyde (2.34 g, 53.16 mmol) was added, the cooling bath was withdrawn and the reaction allowed to warm to r.t. It was then quenched with aqu. sat'd NH$_4$Cl (200 mls) and the THF stripped off in vacuo. The resulting aqueous solution was extracted with ethylacetate (3×200 mls). The organics were combined, dried with MgSO$_4$ and concentrated. The resulting residue was chromatographed (silica gel, ether:.hexanes, 1:1 ) to afford 6.43 g (61% over 3 steps) of 1-(2-(2-pyridyloxy)phenyl)butyn-3-ol as a yellow oil.

To a solution of 1-(2-(2-pyridyloxy)phenyl)butyn-3-ol (6.42 g, 26.9 mmol), triphenylphosphine (9.16 g, 34.9 mmol), and N,O-di-phenylcarbonate hydroxylamine (8.08 g, 29.59 mmol) in THF (100 mls) at 0° C. was added diethyl azodicarboxylate (5.62 g, 32.28 mmol) dropwise. Upon completion of addition, the reaction was stirred for 30 mins. It was then concentrated in vacuo. The resulting residue was chromatographed (silica gel, ether:hexanes, 2:3) to afford 1-(2-(2-pyridyloxy)phenyl)-3-(N-phenoxycarboxy-N-phenoxy carbonate)- 1-butyne.

A solution of 1-(2-(2-pyridyloxy)phenyl)-3-(N-phenoxycarboxy-N-phenoxycarbonate)-1-butyne from above in 3:2 MeOH:NH$_4$OH (125 m mls) was stirred for 3 days. It was then concentrated in vacuo. The resulting residue was chromatographed (silica gel, ether:methanol, 98:2) followed by crystallization in hot ethylacetate to afford the title compound. m.p.=165°–166° C. with decomposition; $^1$H NMR (300 MHz, DMSO-d$_6$): 1.03 (d, 3H, J=6.5 Hz), 4.91 (q, 1H, J=6.5 Hz), 6.47 (bs, 2H), 7.07 (m, 2H), 7.21 (m, 2H), 7.42 (m, 2H), 7.84 (m, 1H), 8.08 (m, 1H), 9.19 (s, 1H); MS (M+H)$^+$=298; Analysis calc'd for C$_{16}$H$_{15}$N$_3$O$_3$: C, 64.64, H, 5.09, N, 14.13; Found:. C, 64.57, H, 5.05, N, 14.16.

Example 141

Preparation of N-hydroxy-N-4-(3-(1-phenylethoxy)phenyl)-3-butyn-2-yl]urea

To a solution of 3-hydroxybenzaldehyde (5.28 g, 43.2 mmol) in DMSO (80 mls) was added potassium t-butoxide (5.58 g, 49.7 mmol) and the mixture was stirred for 20 mins. (1-Bromoethyl)benzene (10.00 g, 54 mmol) was then added dropwise and the reaction was stirred for 18 hrs. It was then diluted with brine (250 mls) and extracted with ethylacetate (3×250 mls). The organics were combined, dried with MgSO₄ and concentrated. The resulting residue was chromatographed (silica gel, hexanes:ether, 92.5:7.5) to afford 5.88 g (60%) of 3-(1-phenylethoxy)benzaldehyde as a pale yellow oil.

The desired material was prepared according to the procedure of Example 140 substituting 3-(1-phenylethoxy)benzaldehyde for 2-(2-pyridyloxy)benzaldehyde. m.p.= 97°–100° C.; ¹H NMR (300 MHz, DMSO-d₆): 1.33 (d, 3H, J=6.5 Hz), 1.53 (d, 3H, J=6.5 Hz), 5.10 (q, 1H, J=6.5 Hz), 5.54 (q, 1H, J=6.5 Hz), 6.55 (bs, 2H), 6.91 (m, 3H), 7.19 (t, 1H, J=8 Hz), 7.24 (m, 1H), 7.31–7.42 (m, 4H), 9.31 (s, 1H); MS (M+H)⁺=325; Analysis calc'd for $C_{19}H_{20}N_2O_3$: C, 70.35, H, 6.22, N, 8.64; Found: C, 70.33, H, 6.22, N, 8.61.

Example 142

Preparation of
N-hydroxy-N-4-(5-(4-fluorophenoxy)benzo[b]
fur-2-yl)-3-butyn-2-yl)urea To a solution of 4-bromophenol (43.25 g, 250 mmol) in DMSO (500 mls) was added potassium t-butoxide (32.26 g, 287.5 mmol) and the mixture was stirred for 20 mins. Allyl bromide (36.29 g, 300 mmol) was then added dropwise and the reaction was stirred for 1 hr. It was then diluted with brine (2 liters) and extracted with ethylacetate (3× 2 liters) The organics were combined, dried with MgSO₄ and concentrated. The crude residue was distilled (b.p.=157° C. at 30 mm Hg) to afford 42.25 g (79%) of 4-allyloxybromobenzene as a colorless oil.

A solution of 4-allyloxybromobenzene (42.24 g, 198.3 mmol), 4-fluorophenol (14.82 g, 132.2 mmol), potassium carbonate (27.41 g, 198.3 mmol) and copper (4.20 g, 66.1 mmol) in pyridine (200 mls) was refluxed for 2 days. It was then filtered through Celite and diluted with ethylacetate(500 mls). The organic was then washed with water (3× 200 mls), dried with MgSO₄ and concentrated. The resulting residue was chromatographed (silica gel, hexanes:ether, 99.75:0.25) to afford 15.85 g (49%) of 4-(4-fluorophenoxy)allyloxybenzene as a lemon yellow oil.

4-(4-Fluorophenoxy)allyloxybenzene (15.84 g, 64.9 mmol) was heated at 230° C. neat for 2 hrs. It was then cooled to r.t. and chromatographed (silica gel, hexanes:ether, 85:15) to afford 16.72 g of 2-allyl-4-(4-fluorophenoxy)phenol as a pale yellow oil which was used as is.

A solution of 2-allyl-4-(4-fluorophenoxy)phenol, from above, in saturated KOH/ethanol (65 mls) was refluxed for 18 hrs. It was then cooled to r.t. and acidified to pH2 by that addition of 10% HCl. The aqueous solution was then extracted with ethylacetate (3×200 mls). The organics were combined, dried with MgSO₄ and concentrated to afford 17.52 g of 2-(1-propenyl)-4-(4-fluorophenoxy)phenol as a brownish oil which was used as is.

Ozone was bubbled through a solution of 2-(1-propenyl)-4-(4fluorophenoxy)phenol, from above, in 1:1 CH₂Cl₂:MeOH (250 mls) at −78° C. until the solution turned light blue. Nitrogen was then bubbled through the solution to remove excess ozone. Dimethylsulfide (40.32 g, 649 mmol) was added dropwise, the cooling bath was removed and the reaction allowed to warm to r.t. and stir for 18 hrs. It was then concentrated and chromatographed (silica gel, hexanes :ether, 9:1 ) to afford 7.62 g (51% over 2 steps) of 2-hydroxy-5-(4-fluorophenoxy)benzaldehyde as a lemon yellow solid.

A solution of 2-hydroxy-5-(4-fluorophenoxy)benzaldehyde (7.41 g, 31.9 mmol), methyl bromoacetate (4.89 g, 31.9 mmol), and potassium carbonate (4.41 g, 31.9 mmol) in acetone ( 150 mls) was refluxed for 18 hrs. It was then cooled to r.t. and concentrated in vacuo. The residue was taken up in brine (100 mls) and extracted with ethylacetate (3×300 mls). The organics were combined, dried with MgSO₄ and concentrated. The resulting residue was taken up in methanol (100 mls) and sodium methoxide (1.72 g, 31.9 mmol) was added. The reaction was brought to reflux for 48 hrs. It was then cooled to r.t., the methanol was concentrated in vacuo, and the resulting residue was diluted with brine (100 mls). This aqueous solution was extracted with ethylacetate (3×100 mls). The organics were combined, dried with MgSO₄ and concentrated. The crude residue was chromatographed (silica gel, hexanes:ether, 85:15) to afford 3.32 g (36%)of methyl 5-(4-fluorophenoxy)benzofuryl-2-carboxylate as a white solid.

A solution of methyl 5-(4-fluorophenoxy)benzofuryl-2-carboxylate (3.32 g, 11.6 mmol) in 1:1 1N LiOH:THF (60 mls) was refluxed for 18 hrs. It was then cooled to r.t., diluted with water (40 mls) and washed with ether (2×100 ntis). The aqueous was then acidified to pH2 by the addition of conc. HCl. The resulting white precipitate was collected, washed with water, taken up in ethylacetate (100 mls), dried with MgSO₄ and concentrated to afford 2.98 g (94%) of 5-(4-fluorophenoxy)benzofuryl-2-carboxylic acid as a white solid.

To a solution of 5-(4-fluorophenoxy)benzofuryl-2-carboxylic acid (2.98 g, 11.0 mmol) in CH₂Cl₂ (50 mls) was added oxalyl chloride (1.67 g, 13.1 mmol) followed by one drop of N,N-dimethylformamide and the reaction was stirred for 1 hr. It was then is concentrated in vacuo. The resulting residue was taken up in CH₂Cl₂ (50 mls) and cooled to 0° C. N,O-Dimethylhydroxylamine hydrochloride (1.28 g, 13.12 mmol) was added followed by the dropwise addition of pyridine (2.09 g, 26.4 mmol). The cooling bath was withdrawn and the reaction allowed to warm to r.t. It was then diluted with brine (50 mls) and the layers were separated. The aqueous was extracted with CH₂Cl₂ (2×50 mls). The organics were combined, dried with MgSO₄ and concentrated. The crude residue was chromatographed (silica gel, CH₂Cl₂:ether, 97.5:2.5) to afford 3.22 g (93%)of N,O-dimethyl-5-(4-flurophenoxy)benzofuryl-2-carboxamide as a white solid.

To a solution of N,O-dimethyl-5-(4-fluorophenoxy)benzofuryl-2-carboxamide (3.22 g, 10.2 mmol) in THF (40 mls) at −78° C., was added diisobutylaluminum hydride (10.2 mls of a 1.0M solution in hexanes, 10.2 mmol) dropwise. Upon completion of addition, the reaction was warmed to 0° C. and allowed to stir for 30 mins. It was then quenched with 10% HCl (70 mls), the cooling bath was removed and the reaction allowed to warm to r.t. The mixture was then extracted with ethylacetate (3×70 mls). The organics were combined, dried with MgSO₄ and concentrated. The crude residue was chromatographed (silica gel, hexanes:ether, 85:15) to afford 2.23 g (85%) of 5-(4-fluorophenoxy)benzofuran-2-carboxaldehyde as a pale yellow solid.

The desired compound was prepared according to the procedure of Example 1 substituting 5-(4-fluorophenoxy)benzofuran-2-carboxaldehyde for 2-(2pyridyloxy)benzaldehyde. m.p.=140° C. (dec); ¹H NMR (300 MHz, DMSO-d₆): 1.40 (d, 3H, J=7 Hz), 5.21 (q, 1H, J=7 Hz), 6.62 (bs, 2H), 7.03–7.25 (m, 7H), 7.58 (d, 1H, J =9 Hz), 9.47 (s, 1H); MS (M+H)⁺=355; Analysis calc'd for $C_{19}H_{15}FN_2O_4 \cdot \frac{1}{4}H_2O$: 63.59, H, 4.35, N, 7.81; Found: C, 63.53, H, 4.16, N, 7.79.

Example 143

Preparation of N-hydroxy-N-4-(7-(4-fluorophenoxy)benzo[b]fur-2-yl)-3-butyn-2-yl)urea The desired compound was prepared according to the procedure of Example 142 substituting 2-bromophenol for 4-bromophenol. m.p.=154°–155° C.; $^1$H NMR (300 MHz, DMSO-$d_6$): 1.38 (d, 3H, J=7 Hz), 5.21 (q, 1H, J=7 Hz), 6.62 (bs, 2H), 6.95 (m, 1H), 7.08 (m, 2H), 7.25 (m, 4H), 7.44 (m, 1H), 9.47 (s, 1H); MS (M+H)$^+$=355; Analysis calc;d for $C_{19}H_{15}FN_2O_4 \cdot \frac{1}{4}H_2O$: C, 63.59, H, 4.35, N, 7.81; Found: C, 63.39, H, 4.12, N, 7.80.

Example 144

Preparation of N-hydroxy,N-4-(benzo[b]fur-2-yl-3-butyn-2-yl)urea

The desired compound was prepared according to the procedure of Example 140 substituting 2-benzofurancarboxaldehyde for 2-(2-pyridyloxy)benzaldehyde. m.p.= 150°–151° C.; $^1$H NMR (300 MHz, DMSO-$d_6$): 1.41 (d, 3H, J=7 Hz), 5.22 (q, 1H, J=7 Hz), 6.63 (bs, 2H), 7.21 (d, 1H, J=0.5 Hz), 7.28 (m, 2H), 7.38 (m, 1H), 7.55 (m, 1H), 7.64 (m, 1H), 9.47 (s, 1H); MS (M+H)$^+$=245; Analysis calc'd for $C_{13}H_{12}N_2O_3$: C, 63.92, H, 4.95, N, 11.47; Found: C, 64.07, H, 5.09, N, 11.43.

Example 145

Preparation of N-hydroxy-N-4-(3-(4-isoquinonyloxy)phenyl)-3-butyn-2-yl)urea

The desired compound was prepared according to the procedure of Example 140 subsituting 3-hydroxybenaldehyde for 2-hydroxybenzaldehyde, 4-bromoisoquinoline for 2-bromopyridine, and lithium diisopropylamide for n-butyllithium. m.p.=157°–158° C.; $^1$H NMR (300 MHz, DMSO-$d_6$): 1.32 (d, 3H, J=6.5 Hz), 5.09 (q, 1H, J=6.5 Hz), 6.53 (bs, 2H), 6.99 (m, 1H), 7.11 (m, 1H), 7.18 (m, 1H), 7.40 (t, 1H, J=8 Hz), 7.82 (m, 2H), 7.99 (m, 1H), 8.24 (m, 2H), 9.23 (s, 1H), 9.31 (s, 1H); MS (M+H)$^+$=348; Analysis calc'd for $C_{20}N_{17}N_3O_3$: C, 69.15, H, 4.93, N, 12.10; Found: C, 68.97, H, 4.98, N, 12.03.

Example 146

Preparation of N-hydroxy-N-4-(3-(2-quinonylmethoxy)phenyl)-3-butyn-2-yl)urea To a solution of 3-iodophenol (3.96 g, 18 mmol) and 2-(chloromethyl)quinoline hydrochloride (3.85 g, 18 mmol) in acetone (90 mls) was added powdered potassium carbonate (7.46 g, 54 mmol) and the reaction was refluxed for 72 hrs. It was then cooled to r.t., filtered through Gelire and concentrated. The crude residue was chromatographed (silica gel, dichloroethane:ether, 99:1 ) to afford 3.92 g of 3-(2-quinonylmethoxy) iodobenzene as a white solid.

A solution of 3-(2-quinonylmethoxy)iodobenzene (4.70 g, 13.0 mmol), 3-butyn-2ol (1.37 g, 19.5 mmol), wiethylamine (13.13 g, 130 mmol) and phenothiazine (a spatula tip) in N,N-dimethylformamide (20 mls) was degassed by bubbling nitrogen through the solution for 30 mins. Copper(I) iodide (25 mg, 0.13 mmol) was then added and the mixture was stirred for 1 hr., Bis (triphenylphosphine)palladium(II) chloride (182 mg, 0.26 mmol) was then added and the reaction was stirred for 18 hrs. It was then diluted with brine (100 mls) and extracted with ethylacetate (3×100 mls). The organics were combined, dried with MgSO$_4$ and concentrated. The resulting residue was is chromatographed (silica gel, ether:hexanes, 3:2) to afford 5.65 g of 1-(3-(2-quinonyl methoxy)phenyl)butyn-3-ol as an orange oil.

The desired material was prepared according to the procedure of Example 140 substituting 1-(3-(2-quinonylmethoxy)phenyl)butyn-3-to for 1-(2-(2-pyridyloxy) phenyl)butyn-3-ol. m.p.=176°–177° C.; $^1$H NMR (300 MHz, DMSO-$d_6$): 1,35 (d, 3H, J= 7 Hz), 5.12 (q, 1H, J=7 Hz), 5.39 (s, 2H), 6.55 (bs, 2H), 6.99 (m, 1H), 7.08 (m, 2H), 7.29 (t, 1H, J=8 Hz), 7.64 (m, 2H), 7.80 (m, 1H), 8.01 (m, 2H), 8.42 (m, 1H), 9.33 (s, 1H); MS (M+H)$^+$=362; Analysis calc'd for $C_{21}H_{19}N_3O_3$: C, 69.79, H, 5.30, N, 11.63; Found: C, 69.52, H, 5..34, N, 11.49.

Example 147

Preparation of N-hydroxy-N-4-(3-(2-quinonyloxy)phenyl)-3-butyn-2-yl)urea

A solution of 3-iodophenol (4.40 g, 20 mmol), 2-chloroquinoline (6.54 g, 40 mmol), potassium carbonate (4.28 g, 31 mmol) and copper (635 rag, 10 mmol) in pyridine (20 mls) was refluxed for 3 days. It was then filtered through Celite and diluted with ethylacetate (100 mls) The organic was then washed with water (3×75 mls), dried with MgSO$_4$ and concentrated. The crude residue was chromatographed (silica gel, hexanes:ether, 98:2) to afford 5.07 g (73%) of 3-(2-quinonyloxy)iodobenzene as a pale yellow solid.

The desired material was prepared according to the procedure of Example 146 substituting 3-(2-quinonyloxy)iodobenzene for 3-(2-quinonylmethoxy)iodobenzene m.p.= 130°–131° C.; $^1$H NMR (300 MHz, DMSO-$d_6$): 1.35 (d, 3H, J=7 Hz), 5.13 (q, 1H, J=7 Hz), 6.55 (bs, 2H), 7.28 (m, 4H), 7.49 (m, 2H), 7.66 (m, 2H), 7.96 (d, 1H, J=8 Hz), 8.43 (d, 1H, J=8.5 Hz), 9.34 (s, 1H); MS (M+H)$^+$=348; Analysis calc'd for $C_{20}H_{17}N_3O_3$: C, 69.15, H, 4.93, N, 12.10; Found: C, 69.03, H, 4.90, N, 12.01.

Example 148

Preparation of N-hydroxy-N-4-(3-pyrazinyloxy)phenyl)-3-butyn-2-yl)urea

The desired material was prepared according to the procedure of Example 147 substituting chloropyrazine for 2-chloroquinoline. m.p.=110°–112° C.; $^1$H NMR (300 MHz, DMSO-$d_6$): 1.35 (d, 3H, J=7 Hz), 5.13 (q, 1H, J=7 Hz), 6.55 (bs, 2H), 7.26 (m, 3H), 7.44 (m, 1H), 8.22 (dd, 1H, J=1.5 Hz, J=3 Hz), 8.39 (d, 1H, J=3 Hz), 8.56 (d, 1H, J=1.5 Hz), 9.34 (s, 1H); MS (M+H)$^+$=299; Analysis calc'd for $C_{15}H_{14}N_4O_3 \cdot \frac{1}{4}H_2$: C, 59.50, H, 4.83, N, 18.50; Found: C, 59.83, H, 4.63, N, 18.34.

Example 149

Preparation of N-hydroxy-N-4-(3-(pyrimid-2-yloxy)phenyl)-3-butyn-2-yl)urea

The desired material was prepared according to the procedure of Example 147 substituting 2-bromopyrimidine for 2-chloroquinoline. m.p.=154°–156° C.; $^1$H NMR (300 MHz, DMSO-$d_6$): 1.36 (d, 3H, J=7 Hz), 5.13 (q, 1H, J=7 Hz), 6.56 (bs, 2H), 7.22 (m, 2H), 7.28 (m, 2H), 7.43 (m, 1H), 8.66 (d, 2H, J=5.5 Hz), 9.34 (s, 1H); MS (M+H)$^+$=299; Analysis calc'd for $C_{15}H_{14}N_4O_3$: C, 60.39, H, 4.73, N, 18.78; Found: C, 60.08, H, 4.71, N, 18.53.

Example 150

Preparation of N-hydroxy-N-4-(2-(4-chlorothiophenoxy)phenyl)-3-butyn-2-yl)urea

The desired material was prepared according to the procedure of Example 140 substituting 2-(4-chlorothiophenoxy)benzaldehyde for 2-(2-pyridyloxy)benzaldehyde. m.p.=151.5°–153.5° C.; $^1$H NMR (300 MHz, DMSO-$d_6$):1.32 (d, 3H, J=7 Hz), 5.13 (q, 1H, J=7 Hz), 6.55 (bs, 2H), 7.01 (m, 1H), 7.28 (m, 2H), 7.46 (m, 5H), 9.32 (s, 1H); MS (M+H)$^+$=347; Analysis calc'd for $C_{17}H_{15}ClN_2O_2S$: C, 58.87, H, 4.36, N, 8.08; Found: C, 58.77, H, 4.52, N, 7.87.

Example 151

Preparation of N-hydroxy-N-3-(1-trans-(2-(3-pyridyloxyphenyl)cycloprop-2-yl-2propynyl)urea The desired material was prepared according to the procedure of Example 140 substituting trans-1-(3-pyridyloxy)phen-3-yl)cyclopropane-2-carboxaldehyde for 2-(2pyridyloxy)benzaldehyde and formaldehyde for acetaldehyde. m.p. = 145°–147° C.; $^1$H NMR (300 MHz, DMSO-$d_6$): 1.24 (m, 2H), 1.65 (m, 1H), 2.23 (m, 1H), 4.05 (d, 2H, J =2 Hz), 6.46 (bs, 2H), 6.84 (m, 1H), 6.89 (m, 1H), 6.95 (m, 1H), 7.30 (t, 1H, J=8.5 Hz), 7.41 (m, 2H), 8.36 (m, 2H), 9.45 (s, 1H); MS (M+H)$^+$=324; Analysis calc'd for $C_{18}H_{17}N_3O_3$: C, 66.86, H, 5.30, N, 13.00; Found: C, 66.52, H, 5.30, N, 12.76.

Example 152

Preparation of N-hydroxy-N-4-(1-trans-(4-methylphenoxy)phenyl)cycloprop-2-yl-3-butyn-2-yl)urea The desired material was prepared, as a mixture of diastereomers, according to the procedure of Example 140 substituting trans- 1-(4-methylphenoxy)phen-3-yl) cyclopropane-2-carboxaldehyde for 2-(2-pyridyloxy)benzaldehyde. m.p.=95°–100° C.; $^1$H NMR (300 MHz, DMSO-$d_6$): 1.19 (m, 2H), 1.23 (d, 3H, J = 7 Hz), 1.59 (m, 1H), 2.16 (m, 1H), 2.29 (s, 3H), 4.87 (m, 1H), 6.46 (bs, 2H), 6.72 (m, 1H), 6.77 (m, 1H), 6.87 (m, 3H), 7.18 (m, 2H), 7.23 (t, 1H, J=7.5 Hz), 9.17 and 9.18 (s, 1H); MS (M+H)$^+$=351; Analysis calc'd for $C_{21}H_{22}N_2O_3$: C, 71.98, H, 6.33, N, 8.00; Found: C, 71.63, H, 6.07, N, 7.94

Example 153

Preparation of N-hydroxy-N-3-(1-trans-(4-methylphenoxy)phenyl)cycloprop-2-yl-2propynyl)urea The desired material was prepared according to the procedure of Example 140 substituting trans- 1-(4-methylphenoxy)phen-3-yl)cyclopropane-2-carboxaldehyde for 2-(2pyridyloxy)benzaldehyde and formaldehyde for acetaldehyde. m.p.=145°–146° C.; $^1$H NMR (300 MHz, DMSO-$d_6$): 1.22 (m, 2H), 1.61 (m, 1H), 2.19 (m, 1H), 2.29 (s, 3H), 4.05 (d, 2H, J=2.5 Hz), 6.47 (bs, 2H), 6.72 (m, 1H), 6.78 (m, 1H), 6.82–6.92 (m, 3H), 7.18 (d, 2H, J=8.5 Hz), 7.23 (t, 1H, J=7.5 Hz), 9.45 (s, 1H); MS (M+H)$^+$=337; Analysis calc'd for $C_{20}H_{20}N_2O_3 \cdot \frac{1}{4}H_2O$: C, 70.46, H, 6.06, N, 8.22; Found: C, 70.77, H, 6.15, N, 8.26.

Example 154

Preparation of N-hydroxy-N-(4-cyclopropyl-3-butyn-2-yl)urea

The desired material was prepared according to the procedure of Example 140 substituting cyclopropanecarboxaldehyde for 2-(2-pyridyloxy)benzaldehyde. m.p.= 141.5°–143.0° C.; 1H NMR (300 MHz, DMSO-$d_6$): 0.52 (m, 2H), 0.72 (m, 2H), 1.20 (d, 3H, J= 6.5 Hz), 1.25 (m, 1H), 4.81 (m, 1H), 6.42 (bs, 2H), 9.12 (s, 1H); MS (M+H)$^+$=169; Analysis calc'd for $C_8H_{12}N_2O_2$: C, 57.12, H, 7.19, N, 16.66; Found: C, 56.89, H, 7.45, N, 16.53.

Example 155

Preparation of N-hydroxy-N-(4-cyclobutyl-3-butyn-2-yl)urea

To a solution of oxalyl chloride (11.86 g, 93.5 mmol) in $CH_2Cl_2$ (350 mls) at −78° C., was added dimethylsulfoxide (15.24 g, 195.12 mmol) dropwise and the mixture was stirred for 5 mins. A solution of cyclobutanemethanol (7.00 g, 81.3 mmol) in $CH_2Cl_2$ (50 mls) was then added dropwise. Upon completion of addition, the reaction is was stirred for 20 mins at −78° C. Triethylamine (41.06 g, 406.5 mmol) was then added dropwise, the cooling bath was removed and the reaction allowed to warm to r.t. and stir for 18 hrs. It was then diluted with water (350 mls) and the layers were separated. The aqueous was extracted with $CH_2Cl_2$ (2×350 mls). The organics were combined, dried with $MgSO_4$ and concentrated. The resulting residue was taken up in ether (250 mls) and the triethylamine hydrochloride was filtered off. The filtrated was concentrated to afford cyclobutanecarboxaldehyde which was used as is.

The desired material was prepared according to the procedure of Example 1 substituting cyclobutanecarboxaldehyde for 2-(2-pyridyloxy)benzaldehyde. m.p.=144°–145° C.; $^1$H NMR, (300 MHz, DMSO-$d_6$): 1.23 (d, 3H, J=7 Hz), 1.70–2.04 (m, 4H), 2.17 (m, 2H), 2.99 (m, 1H), 4.87 (m, 1H), 6.43 (bs, 2H), 9.14 (s, 1H); MS (M+H)$^+$=183;Anlaysis calc'd for $C_9H_{14}N_2O_2$: C, 59.32, H, 7.74, N, 15.38; Found: C, 59.31, H, 7.76, N, 15.38.

Example 156

Preparation of N-hydroxy-N-(4-cyclopentyl-3-butyn-2-yl)urea

The desired material was prepared according to the procedure of Example 155 substituting cyclopentanemethanol for cyclobutanemethanol. m.p.=140°–141° C.; $^1$H NMR (300 MHz, DMSO-$d_6$): 1.21 (d, 3H, J=6.5 Hz), 1.47 (m, 4H), 1.63 (m, 2H), 1.84 (m, 2H), 2.57 (m, 1H), 4.85 (m, 1H), 6.42 (bs, 2H), 9.11 (s, 1H); MS (M+H)$^+$=197; Analysis calc'd for $C_{10}H_{16}N_2O_2$: C, 61.20, H, 8.22, N, 14.28; Found: C, 61.30, H, 8.32, N, 14.27.

Example 157

Preparation of N-hydroxy-N-(4-trans-(2-cyclopropyl)cyclopropyl-3-butyn-2-yl)urea To a solution of N-methoxy-N-methyl diethylphosphonoacetamide (34.56 g, 144.5 mmol) in THF (200 mls) at −78° C., was added n-butyllithium (57.8 mls of a 2.5M solution in hexanes, 144.5 mmol) dropwise. Upon completion of addition, the mixture was stirred for 30 mins at -78° C. A solution of cyclopropanecarboxaldehyde (6.75 g, 96.3 mmol) in THF (50 mls) was then added dropwise. Upon completion of addition, the cooling bath was withdrawn and the reaction allowed to warm to r.t. It was then diluted with aqueous sat'd NH$_4$Cl (200 mls) and the THF was stripped off in vacuo. The aqueous residue was extracted with ethylacetate (3×200 mls). The organics were combined, dried with MgSO$_4$ and concentrated. The resulting residue was chromatographed (silica gel, ether:hexanes, 3:2) to afford 14.09 g (94%) of trans-N-methyl-N-methoxy-3-cyclopropylpropenamide as a colorless oil.

To a suspension of trimethylsulfoxonium iodide (21.99 g, 99.9 mmol) in dimethylsufloxide (300 mls) was added sodium hydride (3.00 g, of and 80% oil suspension, 99.9 mmol) and the mixture was stirred for 20 mins. A solution of trans-N-methoxy-N-methyl-3-cyclopropylpropenamide (14.08 g, 90.8 mmol) in dimethylsulfoxide (50 mls) was then added and the reaction was stirred for 2 hrs at r.t., then heated at 50° C. for 1 hr. It was then diluted with brine (600 mls) and extracted with ethylacetate (3×600 mls). The organics were combined, dried with MgSO$_4$ and concentrated. The resulting residue was chromatographed (silica gel, ether: hexanes, 3:2) to afford trans-2-cyclopropyl-1-N-methoxy-N-methylcyclopropylcarboxamide.

To a solution of trans-2-cyclopropyl-1-N-methoxy-N-methylcyclopropylcarboxamide (6.60 g, 39.1 mmol) in THF (150 mls) at 0° C., was added diisobutylaluminum hydriode (39.1 mls of a 1.0M solution in hexanes, 39.1 mmol) dropwise. Upon completion of addition, the reaction was stirred for 30 mins at 0° C. It was then quenched by the addition of 10% HCl (150 mls) and allowed to waarm to r.t. It was then extracted with ether (3×200 mls). The organics were combined, dried with MgSO$_4$ and concentrated to afford trans-2-cyclopropyl-1-cyclopropanecarboxaldehyde which was used as is.

The desired material was prepared according to the procedure of Example 140 substituting trans-2-cyclopropyl-1-cyclopropanecarboxaldehyde for 2-(2-pyridyloxy)benzaldehyde. m.p.=127°–129° C.; $^1$H NMR (300 MHz, DMSO-d$_6$); 0.00 (m, H), 0.27 (m, 2H), 0.50 (m, 1H), 0.75 (m, 1H), 0.96 (m, 2H), 1.13 (d, 3H, J=6.5 Hz), 4.75 (m, 1H), 6.37 (bs, 2H), 9.05 (s, 1H); MS (M+H)$^+$=209; Analysis calc'd for C$_{11}$H$_{16}$N$_2$O$_2$: C, 63.44, H, 7.75, N, 13.45; Found: C, 63.25, H, 7.73, N, 13.40.

The following examples of lipoxygenase inhibitors shown in Table 3 can be prepared according to the procedures described in example 57 part d and e for the conversion of the acetylene intermediate A to provide the desired acetylenic N-hydroxyurea product.

TABLE 3

| Example | Intermediate A | Product |
|---|---|---|
| 158 | 1-Octyne | N-Hydroxy-N-(3-decyn-2-yl)urea |
| 159 | 1-Octadecyne | N-Hydroxy-N-(3-dodecyn-2yl)urea |
| 160 | 2-Norbornylacetylene | N-Hydroxy-N-(4-norbornyl-3-butyn-2-yl)urea |
| 161 | 2-Hexadecenylacetylene | N-Hydroxy-N-(4-(2-hexadecenyl)-3-butyn-2-yl)urea |
| 162 | 3-Phenoxyphenylmethoxymethylacetylene | N-hydroxy-N-(4-(3-phenoxyphenylmethoxymethyl)-3-butyn-2-yl)ure |
| 163 | 3-Phenoxyphenylmethylthiomethylacetylene | N-hydroxy-N-(4-(3-phenoxyphenylmethylthiomethyl)-3-butyn-2-yl)urea |
| 164 | [N-(3-Phenoxyphenyl)-N-methyl]-aminomethylacetylene | N-hydroxy-N-[(4-(N-3-phenoxyphenyl-N-methyl)aminomethyl)-3-butyn-2-yl]urea |
| 165 | 4-Fluorophenylmethylaminomethylacetylene | N-hydroxy-N-[4-(4-fluorophenylmethylaminomethyl)-3-butyn-2-yl]urea |
| 166 | N-4-Fluorophenyl-N-methylaminomethylacetylene | N-hydroxy-N-[4-((N-4-fluorophenyl-N-methyl)-aminomethyl)-3-butyn-2-yl]urea |

The following examples of lipoxygenase inhibitors shown in Table 4 can be prepared according to the procedures described in example 57 by substituting p-fluorophenol with the requiste intermediate B to provide the desired acetylenic N-hydroxyurea product.

TABLE 4

| Example | Intermediate B | Product |
|---|---|---|
| 167 | 2-Hydroxy-6-methoxypyridine | N-Hydroxy-N-[4-(2-(6-methoxy-pyridyloxy)-2-furyl)-3-butyn-2-yl]urea |
| 168 | 2-Hydroxy-6-methylpyridine | N-Hydroxy-N-[4-(2-(6-methyl-pyridyloxy)-2-furyl)-3-butyn-2-yl]urea |
| 169 | 6-Chloro-2-hydroxypyridine | N-Hydroxy-N-[4-(2-(6-chloro-pyridyloxy)-2-furyl)-3-butyn-2-yl]urea |
| 170 | 2,6-Dimethyl-3-hydroxypyridine | N-Hydroxy-N-[4-(3-(2,6-dimethyl-pyridyloxy)-2-furyl)-3-butyn-2-yl]urea |
| 171 | 2,6-Dimethyl-4-hydroxypyridine | N-Hydroxy-N-[4-(4-(2,6-dimethyl-pyridyloxy)-2-furyl)-3-butyn-2-yl]urea |
| 172 | 2-Fluoro-4-hydroxypyridine | N-Hydroxy-N-[4-(4-(2-fluoro-pyridyloxy)-2-furyl)-3-butyn-2yl]urea |
| 173 | 2-Mercapto-6-methylpyridine | N-Hydroxy-N-[4-(2-(6-methyl-pyridylthiol)-2-furyl)-3-butyn-2-yl]urea |
| 174 | 2,6-Dimethyl-4-mercaptopyridine | N-Hydroxy-N-[4-(4-(2,6-dimethyl-pyridylthiol)-2-furyl)-3-butyn-2-yl]urea |
| 175 | 6-Fluoro-3-mercaptopyridine | N-Hydroxy-N-[4-(3-(6-fluoro-pyridylthiol)-2-furyl)-3-butyn-2-yl]urea |

The foregoing examples are illustrative of the present invention and are not to read as limiting the scope of the invention as it is defined by the appended claims.

We claim:

1. A compound having the structure

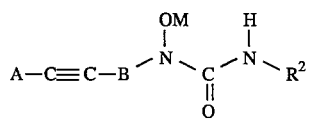

wherein

B is a valence bond or is a straight or branched divalent alkylene group of one to twelve carbon atoms, M represents hydrogen or a pharmaceutically acceptable cation, R$^2$ is selected from the group consisting of
hydrogen,
alkyl of from one to six carbon atoms,
hydroxyalkyl of from one to six carbon atoms, alkoxyalkyl in which the alkoxy portion and the alkyl portion each contain, independently, from one to six carbon atoms, alkanoyl of from two to eight carbon atoms, A is optionally substituted phenyl;

wherein the optional substituent on the phenyl group is phenoxy, optionally substituted with alkyl of from one to six carbon atoms, haloalkyl of from one to six carbon atoms, alkoxy of from one to six carbon atoms, hydroxy or halogen; and the pharmaceutically acceptable salts thereof.

2. A compound, or pharmaceutically acceptable salt thereof, as defined by claim 1 having the structure

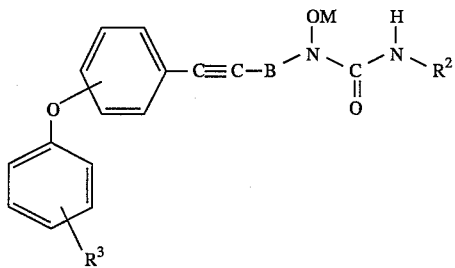

or a pharmaceutically acceptable salt thereof wherein

B is selected from the group consisting of a valence bond, —$CH_2$—, and a straight or branched divalent alkylene group of one to twelve carbon atoms;

M represents hydrogen, or a pharmaceutically acceptable cation;

$R^2$ is selected from the group consisting of
hydrogen,
alkyl of from one to six carbon atoms,
hydroxyalkyl of from one to six carbon atoms,
alkoxyalkyl in which the alkoxy portion and the alkyl portion independently, have from one to six carbon atoms,
alkanoyl of from two to eight carbon atoms, and $R^3$ is selected from the group consisting of
alkyl of from one to six carbon atoms,
haloalkyl of from one to six carbon atoms,
hydroxyalkyl of from one to six carbon atoms,
alkoxy of from one to twelve carbon atoms,
hydroxy,
halogen,
amino,
alkylamino of from one to six carbon atoms, and
dialkylamino in which the two alkyl groups independently have from one to six carbon atoms.

3. A compound, or pharmaceutically acceptable salt thereof, having the name N-hydroxy-N-(4-(3-(4-fluorophenoxy)phenyl)-3-butyn-2-yl)urea.

4. A compound, or pharmaceutically acceptable salt thereof, having the name (+)-N-hydroxy-N-(4-(3-(4-fluorophenoxy)phenyl)-3-butyn-2-yl)urea.

5. A compound, or pharmaceutically acceptable salt thereof, having the name (−)-N-hydroxy-N-(4-(3-(4-fluorophenoxy )phenyl)-3-butyn-2-yl)urea.

6. A pharmaceutical composition for inhibiting the biosynthesis of leukotrienes comprising a therapeutically effective amount of a compound as defined by claim 4 in combination with a pharmaceutically acceptable carrier.

7. A method of inhibiting the biosynthesis of leukotrienes comprising administering to a mammal in need of such treatment a therapeutically effective amount of a compound as defined by claim 4.

* * * * *

UNITED STATES PATENT AND TRADEMARK OFFICE
CERTIFICATE OF CORRECTION

PATENT NO. : 5,476,873  Page 1 of 9
DATED : December 19, 1995
INVENTOR(S) : Dee W. Brooks, et al.

It is certified that error appears in the above-indentified patent and that said Letters Patent is hereby corrected as shown below:

Column 1, Line 34, change "meals" to --mammals--.

Column 3, Line 49, change "diallcylaminocarbonyl" to --dialkylaminocarbonyl--

Column 3, Line 67, change "4-pyrictinyloxy" to --4-pyridinyloxy--.

Column 7, Line 28, change "hydrocaren" to --hydrocarbon--.

Column 8, Line 51, change "arylallcyl" to --arylalkyl--.

Column 8, Line 58, change "clearable" to --cleavable--.

Column 12, Line 53, change "burylthien" to --butylthien--.

Column 13, Line 47, change "rosylate" to --tosylate--.

UNITED STATES PATENT AND TRADEMARK OFFICE
CERTIFICATE OF CORRECTION

PATENT NO. : 5,476,873
DATED : December 19, 1995
INVENTOR(S) : Dee W. Brooks, et al.

It is certified that error appears in the above-indentified patent and that said Letters Patent is hereby corrected as shown below:

Column 15, Line 34, change "garage" to --gavage--.

Column 17, Line 39, change "hydroxylme" to --hydroxylamine--.

Column 17, Line 43, change "convened" to --converted--.

Column 19, Line 49, change "FTBHA" to --PTBHA--.

Column 21, Line 63, change "carder" to --carrier--.

Column 22, Line 1, change "hurnectants" to --humectants--.

Column 22, Line 9, change "tale" to --talc--.

Column 22, Line 11, change "capstries" to --capsules--.

Column 22, Line 49, change "bentonitc" to --bentonite--.

UNITED STATES PATENT AND TRADEMARK OFFICE
CERTIFICATE OF CORRECTION

PATENT NO. : 5,476,873  
DATED : December 19, 1995  
INVENTOR(S) : Dee W. Brooks, et al.

Page 3 of 9

It is certified that error appears in the above-indentified patent and that said Letters Patent is hereby corrected as shown below:

Column 24, Line 12, change "butyn" to
-- 3-butyn --.

Column 25, Line 23, change "(4benzyloxphenyl)" to
--(4-benzyloxyphenyl)--.

Column 25, Line 45, change "$_6$)," to
--d$_6$),--.

Column 27, Line 34, change "said" to
--satd.--.

Column 29, Line 66, change "6,93" to
--6.93--.

Column 30, Line 37, change "(dr," to
--(dt.--.

Column 31, Line 28, change "trirnethysilyl" to
--trimethylsilyl--.

Column 32, Line 60, change "tide" to
--title--.

Column 33, Line 60, change "pan" to
--para--.

UNITED STATES PATENT AND TRADEMARK OFFICE
CERTIFICATE OF CORRECTION

PATENT NO. : 5,476,873  Page 4 of 9
DATED : December 19, 1995
INVENTOR(S) : Dee W. Brooks, et al.

It is certified that error appears in the above-indentified patent and that said Letters Patent is hereby corrected as shown below:

Column 34, Line 36, change "$O_1$" to --$O_3$--.

Column 35, Line 39, delete --s--.

Column 35, Line 43, change "dr" to --dt--.

Column 35, Line 45, change "(25,M++H4) to --(25, M++NH4)--.

Column 35, Line 60, delete --Is--.

Column 36, Line 21, change "off" to --of--.

Column 36, Line 45, change "panformaldehyde" to --paraformaldehyde--.

Column 37, Line 15, delete --s--.

UNITED STATES PATENT AND TRADEMARK OFFICE
CERTIFICATE OF CORRECTION

PATENT NO. : 5,476,873  
DATED : December 19, 1995  
INVENTOR(S) : Dee W. Brooks, et al.

It is certified that error appears in the above-indentified patent and that said Letters Patent is hereby corrected as shown below:

Column 37, line 16, change "trinethylsilyl" to --trimethylsilyl--.

Column 37, Line 32, change "panformaldehyde" to --paraformaldehyde--.

Column 37, Line 32, delete --s--.

Column 38, Line 10, delete --s--.

Column 38, Line 12, change "dr" to --dt--.

Column 38, Line 26, after the word "using" insert --3--.

Column 38, Line 38, change "furyl[" to --furyl]--.

Column 39, Line 21, change "penme" to --pentane--.

Column 39, Line 26, change "43°" to --10°--.

Column 39, Line 48, delete --s--.

UNITED STATES PATENT AND TRADEMARK OFFICE
CERTIFICATE OF CORRECTION

PATENT NO. : 5,476,873
DATED : December 19, 1995
INVENTOR(S) : Dee W. Brooks, et al.

It is certified that error appears in the above-indentified patent and that said Letters Patent is hereby corrected as shown below:

Column 40, Line 29, change "TIF" to
--THF--.

Column 41, Line 23, change "5 TMS" to
--δTMS--.

Column 41, Line 35, change "1130" to
--100--.

Column 41, Line 65, change "15" to
--δ--.

Column 42, Line 43, change "dr" to
--dt--.

Column 42, Line 45, change "(M++H," to
--(M++H,--.

Column 44, Line 13, change "(M++NH$_{4,100}$)" to
--(M++NH$_4$,100)--.

Column 44, Line 32, change "(M++NH$_{4,65}$)" to
--(M++NH$_4$, 65)--.

Column 44, Line 66, change "(M+NH$_4$)+ to
--(M+NH$_4$)+--.

UNITED STATES PATENT AND TRADEMARK OFFICE
CERTIFICATE OF CORRECTION

PATENT NO. : 5,476,873
DATED : December 19, 1995
INVENTOR(S) : Dee W. Brooks, et al.

It is certified that error appears in the above-indentified patent and that said Letters Patent is hereby corrected as shown below:

Column 47, Line 56, delete

--as--.

Column 49, Line 5, change "difluorophenoxyl" to

--difluorophenoxy)--.

Column 49, Line 8, change ".was" to

--was--.

Column 49, Line 31, change "(M+1)-" to

--(M+1)+--.

Column 50, Line 14, change "(M+NHhd)+" to

--(M+NH4)+--.

Column 50, Line 40, change "tide" to

--title--.

Column 52, Line 21, change "cyanophenoxyy" to

--cyanophenoxy--.

Column 54, Line 60, change "rifle" to

--title--.

Column 55, Line 25, in front of "-(4-fluorophenoxy)" insert

--2--.

Column 55, Line 43, change "2-(2-phenylethynyl)" to

-- 5-(2-phenylethynyl)  --.

UNITED STATES PATENT AND TRADEMARK OFFICE
CERTIFICATE OF CORRECTION

PATENT NO. : 5,476,873  Page 8 of 9
DATED : December 19, 1995
INVENTOR(S) : Dee W. Brooks, et al.

It is certified that error appears in the above-indentified patent and that said Letters Patent is hereby corrected as shown below:

Column 57, Line 60, change "thionyl" to --thienyl--.

Column 57, Line 67, change "(M+1)-" to --(M+1)+--.

Column 58, Line 2, change "3.45" to --53.45--.

Column 58, Line 16, change "J=1 Hz" to --J=5 Hz--.

Column 58, Line 31, change "5-phenyfurfuml" to --5-phenyfurfural--.

Column 58, Line 66, change "(DCO-$NH_3$)" to --(DCI-$NH_3$)--.

Column 59, Line 28, change "6,91" to --6.91--.

Column 61, Line 28, change "(M+1)+" to --(M+1)+--.

Column 64, Line 7, change "(3x300 mls)" to --(3x100 mls)--.

Column 64, Line 23, change "ntis)." to --mls).--.

UNITED STATES PATENT AND TRADEMARK OFFICE
CERTIFICATE OF CORRECTION

PATENT NO. : 5,476,873
DATED : December 19, 1995
INVENTOR(S) : Dee W. Brooks, et al.

It is certified that error appears in the above-indentified patent and that said Letters Patent is hereby corrected as shown below:

Column 65, Line 57, change "Gelire" to --Celite--.

Column 65, Line 62, change "wiethylamine" to --triethylamine--.

Column 66, Line 10, change "-3-to" to -- -3-ol --.

Column 68, Lines 62-63, change "diethylphosphonoacetarnide" to --diethylphosphonoacetamide--.

Signed and Sealed this

Twenty-ninth Day of October 1996

*Attest:*

BRUCE LEHMAN

*Attesting Officer*   *Commissioner of Patents and Trademarks*